(12) United States Patent
Anèmian et al.

(10) Patent No.: US 10,490,747 B2
(45) Date of Patent: *Nov. 26, 2019

(54) FORMULATIONS AND ELECTRONIC DEVICES

(71) Applicant: Merck Patent GmbH, Darmstadt (DE)

(72) Inventors: Rémi Manouk Anèmian, Frankfurt am Main (DE); Susanne Heun, Bad Soden (DE); Thomas Eberle, Landau (DE); Philipp Stoessel, Frankfurt am Main (DE); Aurélie Ludemann, Franfurt am Main (DE); Dietmar Kunkel, Gernsheim (DE)

(73) Assignee: Merck Patent GmbH, Darmstadt (DE)

( * ) Notice: Subject to any disclaimer, the term of this patent is extended or adjusted under 35 U.S.C. 154(b) by 77 days.

This patent is subject to a terminal disclaimer.

(21) Appl. No.: 15/846,480

(22) Filed: Dec. 19, 2017

(65) Prior Publication Data

US 2018/0114912 A1 Apr. 26, 2018
US 2019/0207114 A9 Jul. 4, 2019

Related U.S. Application Data

(63) Continuation of application No. 14/837,724, filed on Aug. 27, 2015, now Pat. No. 9,882,135, which is a (Continued)

(30) Foreign Application Priority Data

May 3, 2010 (WO) .................. PCT/EP2010/002683
Aug. 18, 2010 (WO) .................. PCT/EP2010/005056
Sep. 15, 2010 (WO) .................. PCT/EP2010/005648

(51) Int. Cl.
*H01L 51/00* (2006.01)
*C07F 15/00* (2006.01)
(Continued)

(52) U.S. Cl.
CPC .......... *H01L 51/0037* (2013.01); *C07C 15/30* (2013.01); *C07C 15/38* (2013.01);
(Continued)

(58) Field of Classification Search
CPC ............... H01L 51/0054; H01L 51/005; H01L 51/0067; H01L 51/0072; H01L 51/0052; H01L 51/0085; H01L 51/00; H01L 51/30; H01L 51/46; H01L 51/54; H01L 51/0037; H01L 51/0058; H01L 51/5016; H01L 2251/308; C07F 15/00; C07F 5/025; C07F 7/0812; C07F 9/65683; C07F 9/65685; C07F 9/65848; C07F 19/00; C07F 15/0086; C07F 15/0033; C09D 139/04; H05B 33/14; C07C 2603/24; C07C 2603/42; C07C 15/30; C07C 15/38; Y02E 10/549; C09K 2211/185; C09K 2211/1096; C09K 2211/1092; C09K 2211/1088;
(Continued)

(56) References Cited

U.S. PATENT DOCUMENTS 6,770,396 B2 8/2004 Hatoh et al.
7,560,604 B2 7/2009 Kubota et al.
(Continued)

FOREIGN PATENT DOCUMENTS

CN 1492904 A 4/2004
CN 1678617 A 10/2005
(Continued)

OTHER PUBLICATIONS

U.S. Appl. No. 13/322,614.
(Continued)

*Primary Examiner* — Douglas J McGinty
(74) *Attorney, Agent, or Firm* — Drinker Biddle & Reath LLP

(57) ABSTRACT

A formulation comprising at least one solvent and at least two different functional compounds of formula (I)

$$A\text{-}[B]_k \quad (I)$$

wherein
A is a functional structural element, the structural element serving as host material, as a unit that has hole-injection and/or hole-transport properties, as a unit t at has electron-injection and/or electron-transport properties, as a unit which has light-emitting properties, or as a unit which improves the transfer from the singlet state to the triplet state of light-emitting compounds;
B is a solubility-promoting structural element; and
k is an integer in the range from 1 to 20;
the molecular weight of the functional compound is at least 550 g/mol, and the solubility-promoting structural element B conforms to the general formula (L-I)

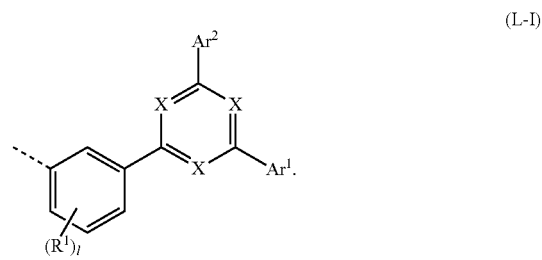

23 Claims, 1 Drawing Sheet

Related U.S. Application Data continuation of application No. 13/695,703, filed as application No. PCT/EP2010/007176 on Nov. 26, 2010, now Pat. No. 9,159,930.

(51) Int. Cl.
| | |
|---|---|
| C09K 11/06 | (2006.01) |
| H05B 33/14 | (2006.01) |
| C07F 19/00 | (2006.01) |
| C07C 15/30 | (2006.01) |
| C07C 15/38 | (2006.01) |
| C07F 5/02 | (2006.01) |
| C07F 7/08 | (2006.01) |
| C07F 9/6568 | (2006.01) |
| C07F 9/6584 | (2006.01) |
| C09D 139/04 | (2006.01) |
| H01L 51/50 | (2006.01) |

(52) U.S. Cl.
CPC ............ *C07F 5/025* (2013.01); *C07F 7/0812* (2013.01); *C07F 9/65683* (2013.01); *C07F 9/65685* (2013.01); *C07F 9/65848* (2013.01); *C07F 15/0033* (2013.01); *C07F 15/0086* (2013.01); *C07F 19/00* (2013.01); *C09D 139/04* (2013.01); *C09K 11/06* (2013.01); *H01L 51/0054* (2013.01); *H01L 51/0058* (2013.01); *H01L 51/0085* (2013.01); *H05B 33/14* (2013.01); *C07C 2603/24* (2017.05); *C07C 2603/42* (2017.05); *C09K 2211/1007* (2013.01); *C09K 2211/1011* (2013.01); *C09K 2211/1022* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/1096* (2013.01); *C09K 2211/185* (2013.01); *H01L 51/0052* (2013.01); *H01L 51/5016* (2013.01); *H01L 2251/308* (2013.01); *Y02E 10/549* (2013.01)

(58) Field of Classification Search
CPC .... C09K 2211/1059; C09K 2211/1044; C09K 2211/1029; C09K 2211/1022; C09K 2211/1011; C09K 2211/1007; C09K 11/06
USPC ................ 252/519.21, 519.2, 500; 438/99
See application file for complete search history.

(56) References Cited

U.S. PATENT DOCUMENTS

| | | | |
|---|---|---|---|
| 7,732,598 B2 | 6/2010 | Shin et al. | |
| 7,883,785 B2 | 2/2011 | Stossel et al. | |
| 8,022,617 B2 | 9/2011 | Iida et al. | |
| 8,314,549 B2 | 11/2012 | Burn et al. | |
| 9,159,930 B2 * | 10/2015 | Anemian | C09K 11/06 |
| 9,666,806 B2 | 5/2017 | Anemian et al. | |
| 9,735,385 B2 | 8/2017 | Kroeber et al. | |
| 9,882,135 B2 * | 1/2018 | Anemian | C09K 11/06 |
| 2004/0146743 A1 | 7/2004 | O'Dell et al. | |
| 2005/0249970 A1 | 11/2005 | Suzuri et al. | |
| 2006/0014046 A1 | 1/2006 | Wang et al. | |
| 2006/0127696 A1 | 6/2006 | Stossel et al. | |
| 2007/0009760 A1 | 1/2007 | Inoue et al. | |
| 2007/0013296 A1 | 1/2007 | Kubota et al. | |
| 2008/0009627 A1 | 1/2008 | Tsuboyama et al. | |
| 2008/0088230 A1 | 4/2008 | Suzuri et al. | |
| 2008/0113101 A1 | 5/2008 | Inoue et al. | |
| 2009/0066223 A1 | 3/2009 | Yabe et al. | |
| 2009/0140637 A1 | 6/2009 | Hosokawa et al. | |
| 2009/0191426 A2 | 7/2009 | Yabe et al. | |
| 2010/0090588 A1 | 4/2010 | Yokoyama et al. | |
| 2010/0219404 A1 | 9/2010 | Endo et al. | |
| 2011/0095282 A1 | 4/2011 | Pflumm et al. | |
| 2011/0140043 A1 | 6/2011 | Stoessel et al. | |
| 2012/0017556 A1 | 1/2012 | Reeves | |
| 2012/0175561 A1 | 7/2012 | Franz et al. | |
| 2012/0238105 A1 | 9/2012 | Anemian et al. | |
| 2017/0125676 A1 | 5/2017 | Anemian et al. | |

FOREIGN PATENT DOCUMENTS

| | | | | |
|---|---|---|---|---|
| CN | 101128560 | A | 2/2008 | |
| CN | 101177608 | A | 5/2008 | |
| CN | 101193842 | A | 6/2008 | |
| CN | 101268029 | A | 9/2008 | |
| CN | 101287713 | A | 10/2008 | |
| DE | 10238903 | A1 | 3/2004 | |
| EP | 2202818 | A4 | 11/2010 | |
| JP | 2002-193952 | A | 7/2002 | |
| JP | 2003-347056 | A | 12/2003 | |
| JP | 2005-340183 | A | 12/2005 | |
| JP | 2007-015993 | A | 1/2007 | |
| JP | 2007126443 | A | 5/2007 | |
| JP | 2007-223929 | A | 9/2007 | |
| JP | 2007-254312 | A | 10/2007 | |
| JP | 2007-261969 | A | 10/2007 | |
| JP | 2008127316 | A | 6/2008 | |
| JP | 2010185047 | A | 8/2010 | |
| KR | 20080028425 | A | 3/2008 | |
| KR | 20080061370 | A | 7/2008 | |
| KR | 20090047547 | A | 5/2009 | |
| WO | WO-2004/020504 | A1 | 3/2004 | |
| WO | WO-2004095889 | A1 | 11/2004 | |
| WO | WO-2005033118 | A1 | 4/2005 | |
| WO | WO-2006/097717 | A1 | 9/2006 | |
| WO | WO-2006/129107 | A1 | 12/2006 | |
| WO | WO-2007007463 | A1 | 1/2007 | |
| WO | WO-2008/025997 | A1 | 3/2008 | |
| WO | WO-2009/011272 | A1 | 1/2009 | |
| WO | WO-2009021107 | A1 | 2/2009 | |
| WO | WO-2009041635 | A1 | 4/2009 | |
| WO | WO-2010/036459 | A1 | 4/2010 | |
| WO | WO-2011032626 | A1 | 3/2011 | |
| WO | WO-2011032686 | A1 * | 3/2011 | ........... H01L 51/005 |

OTHER PUBLICATIONS

European Examination Report issued in corresponding EP Patent Application No. 10788016.3, dated Mar. 3, 2014, no English translation.

Chinese Office Action dated Aug. 12, 2014 for Chinese Patent Application No. 2910-80066572.

Japanese Office Action dated Oct. 21, 2014 for Japanese Patent Application No. 2013-508376.

English Translation of JP 2007-126443, May 24, 2007.

International Search Report for PCT/EP2010/007176, dated May 4, 2011.

Chinese Office Action for Chinese Application No. 201080041111.7 dated Jan. 4, 2016.

European Examination procedure for application No. 10757570.6, dated Feb. 27, 2015.

European Examination procedure for application No. 10757570.6, dated Nov. 13, 2013.

Kimura, M., et al., "Energy transfer within ruthenium-cored rigid metallodendrimers", Tetrahedron Letters, vol. 41, No. 35, (2000), pp. 6809-6813.

International Search Report (English translation) for PCT/EP2010/005648 dated Dec. 15, 2010.

International Preliminary Report on Patentability (in German) for PCT/EP2010/005648 dated Mar. 20, 2012.

(56) References Cited

OTHER PUBLICATIONS

Miller, T., et al., "Synthesis and characterization of a series of monodisperse 1,3,5-phenylene-based hydrocarbon dendrimers including $C_{276}H_{186}$ and their fluorinated analogs", Journal of the American Chemical Society, vol. 114, No. 3, (1992), pp. 1018-1025.

* cited by examiner

| | | |
|---|---|---|
| 3 nm / 100 nm | Cathode | Ba/Al |
| 80 nm | EML | Matrix + emitter |
| 20 nm | HIL | HIL-012 |
| 80 nm | Buffer layer | PEDOT |
| | ITO | |

FORMULATIONS AND ELECTRONIC DEVICES

RELATED APPLICATIONS

This application is a continuation of U.S. patent application Ser. No. 14/837,724, filed Aug. 27, 2015, which is a continuation application of U.S. patent application Ser. No. 13/695,703, filed Nov. 1, 2012, and claims benefit under 35 U.S.C. § 120. U.S. patent application Ser. No. 13/695,703 is a national stage application (under 35 U.S.C. § 371), and claims benefit under 35 U.S.C. § 119 of PCT/EP2010/007176, filed Nov. 26, 2010, which in turn claims benefit to PCT Application No. PCT/EP2010/002683, filed May 3, 2010, PCT Application No. PCT/EP2010/005056, filed Aug. 18, 2010, and PCT Application No. PCT/EP2010/005648, filed Sep. 15, 2010. Each of the applications listed are incorporated herein by reference.

The present invention relates to formulations for the production of electronic devices. The present invention furthermore relates to electronic devices and to processes for the production thereof.

BACKGROUND OF THE INVENTION

Electronic devices which comprise organic, organometallic and/or polymeric semiconductors are increasing in importance; they are employed in many commercial products for cost reasons and owing to their performance. Examples which may be mentioned here are organic-based charge-transport materials (for example triarylamine-based hole transporters) in photocopiers, organic or polymeric light-emitting diodes (OLEDs or PLEDs) in display devices, or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may achieve major importance in the future.

Irrespective of the particular application, many of these electronic devices have the following general layer structure, which can be adapted for the particular application:
(1) substrate,
(2) electrode, frequently metallic or inorganic, but also made from organic or polymeric conductive materials,
(3) charge-injection layer(s) or interlayer(s), for example for compensation of electrode unevenness ("planarisation layer"), frequently made from a conductive, doped polymer,
(4) organic semiconductors,
(5) optionally further charge-transport, charge-injection or charge-blocking layers,
(6) counterelectrode, materials as mentioned under (2),
(7) encapsulation.

The above arrangement represents the general structure of an organic electronic device, where various layers can be combined, resulting in the simplest case in an arrangement comprising two electrodes, between which an organic layer is located. In this case, the organic layer fulfils all functions, including the emission of light in the case of OLEDs. A system of this type is described, for example, in WO 90/13148 A1 based on poly-(p-phenylenes).

However, a problem which arises in a "three-layer system" of this type is the lack of control of charge separation or the lack of a way of optimising the properties of the individual constituents in different layers, as is achieved in a simple manner by a multilayered structure, for example, in the case of SMOLEDs ("small-molecule OLEDs").

A small-molecule OLED often comprises one or more organic hole-injection layers, hole-transport layers, emission layers, electron-transport layers and/or electron-injection layers and an anode and a cathode, where the entire system is usually located on a glass substrate. The advantage of a multilayered structure of this type consists in that the various functions of charge injection, charge transport and emission can be distributed over the various layers and the properties of the respective layers can thus be modified separately. This modification enables the performance of the electronic devices to be considerably improved.

A disadvantage of electronic devices which are based on the small molecules described above, i.e. non-polymeric compounds, is the production thereof. Non-polymeric compounds are usually converted into electronic devices by evaporation techniques. This represents a major cost disadvantage, in particular for large-area devices, since a multistep vacuum process in various chambers is very expensive and must be controlled very precisely. Less expensive and established coating methods from solution, such as, for example, ink-jet printing, airbrush methods, roll-to-roll processes, etc., would be a major advantage here. However, the above-described devices comprising small molecules generally cannot be produced in this way owing to the low solubility of the non-polymeric compounds in the usual solvents. Although the solubility of these compounds can be improved by modification, the electronic devices obtained exhibit, however, reduced performance and lifetime compared with the devices obtained by gas-phase deposition.

Thus, for example, WO 2009/021107 A1 and WO 2010/006680 A1 describe organic compounds which are suitable for the production of electronic devices, where these compounds can be processed both by gas-phase deposition and from solution. However, the electronic devices obtained by gas-phase deposition have a more favourable property profile.

Known electronic devices have a usable property profile. However, there is an ongoing necessity to improve the properties of these devices. These properties include, in particular, the lifetime of the electronic devices. A further problem is, in particular, the energy efficiency with which an electronic device achieves the specified object. In the case of organic light-emitting diodes, which may be based both on low-molecular-weight compounds and also on polymeric materials, the light yield, in particular, should be high, meaning that as little electrical power as possible has to be con-sumed in order to achieve a certain light flux. Furthermore, the lowest possible voltage should also be necessary in order to achieve a pre-specified luminous density.

A further object can be regarded as the provision of electronic devices having excellent performance as inexpensively as possible and in constant quality.

Furthermore, the electronic devices should be capable of being employed or adapted for many purposes. In particular, the performance of the electronic devices should be retained over a broad temperature range.

SUMMARY OF THE INVENTION

Surprisingly, it has been found that these and further objects, which are not mentioned explicitly, but can readily be derived or inferred from the connections discussed in the introduction herein, are achieved by formulations having all features of Patent Claim 1. Advantageous modifications of the formulations according to the invention are protected in the claims which are dependent on Claim 1.

The present invention accordingly relates to a formulation comprising at least one solvent and at least two different functional compounds of the general formula (I)

  (I)

where
A is a functional structural element,
B is a solubility-promoting structural element and
k is an integer in the range from 1 to 20,
the molecular weight of the functional compound is at least 550 g/mol and the solubility-promoting structural element B conforms to the general formula (L-I)

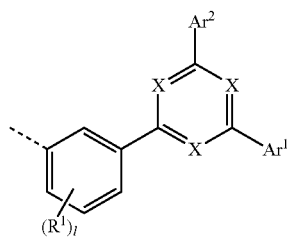  (L-I)

where
$Ar^1$, $Ar^2$ is each, independently of one another, an aryl or heteroaryl group, which may be substituted by one or more radicals R of any desired type,
X is in each case, independently of one another, N or $CR^2$, preferably CH,
$R^1$, $R^2$ is each, independently of one another, hydrogen, a straight-chain alkyl, alkoxy or thioalkoxy group having 1 to 40 C atoms or a branched or cyclic alkyl, alkoxy or thioalkoxy group having 3 to 40 C atoms or is a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—X, in which X represents a halogen atom), a formyl group (—C(=O)—H), an isocyano group, an isocyanate group, a thiocyanate group or a thioisocyanate group, a hydroxyl group, a nitro group, a $CF_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$ and/or $R^2$ may form a mono- or polycyclic, aliphatic or aromatic ring system with one another and/or with the ring to which the group $R^1$ is bonded; and
l is 0, 1, 2, 3 or 4;
where the dashed bond indicates the bond to the functional structural element.

Accordingly, a formulation according to the invention represents a mixture of at least two functional compounds of the formula (I) which are dissolved or dispersed in an organic solvent.

DETAILED DESCRIPTION OF THE INVENTION

A formulation according to the invention comprises at least one organic solvent. Suitable and preferred solvents are aliphatic, cycloaliphatic or aromatic hydrocarbons, amines, thiols, amides, nitriles, esters, ethers, polyethers, alcohols, diols and/or polyols.

The solvent preferably comprises at least one aromatic or heteroaromatic compound. The solvent particularly preferably comprises at least one aromatic hydrocarbon and/or halogenated aromatic compound, which particularly preferably contain(s) at least one alkyl group and/or cycloalkyl group having 1 to 8 carbon atoms, preferably having 1 to 6 carbon atoms. These include, in particular, toluene, dimethylbenzene (xylenes), trimethyl-benzenes, methylnaphthalenes, tetralin, cyclopentylbenzene and cyclo-hexylbenzene.

In accordance with a further embodiment of the present invention, use may be made of aromatic or heteroaromatic compounds which contain heteroatoms in the side group, in particular esters, ethers, nitriles and/or amides. The preferred compounds in this class include aromatic alkoxy compounds, such as, for example, 3-methylanisole, 2-isopropylanisole, 5-methoxy-indane, 2-ethoxynaphthalene, and aromatic esters, such as, for example, butyl benzoate and ethyl benzoate. Also suitable are heteroaromatic solvents containing an O, N or S atom in the aromatic ring, such as, for example, 2-methylindole and 6-methylquinoline.

The solvents employed can furthermore be heterocyclic compounds, such as, for example, 1-cyclohexyl-2-pyrrolidinone (N-cyclohexyl-pyrrolidinone).

Furthermore, alcohols represent a suitable class of solvents. The preferred alcohols include, in particular, alkylcyclohexanols, in particular methylated alicyclic alcohols (3- or 4-methylcyclohexanol or 2,5-dimethylcyclohexanol), naphthols, for example decahydro-2-naphthol or 1,2,3,4-tetrahydro-1-naphthol, terpenoids, such as, for example, α-terpineol, menthol or carveol, nonylphenol, 1-indanol and 2-indanol.

In addition, the solvents employed can be cycloalkanes, such as, for example, decalin.

The solvents can be employed individually or as a mixture of two, three or more compounds.

The preferred solvents include, inter alia, toluene, anisole, xylenes, methyl benzoate, dimethylanisoles, mesitylenes, tetralin, veratrol, tetrahydrofuran and chlorobenzene, and mixtures thereof. Particular preference is given to the use of aromatic solvents, in particular aromatic hydrocarbons. A formulation according to the invention can preferably comprise at least 50% by weight, particularly preferably at least 80% by weight and very particularly preferably at least 90% by weight, of aromatic solvent.

Surprising advantages can be achieved, in particular, by solvents whose Hansen solubility parameters are preferably in the following ranges:
$H_d$ (dispersion contribution) in the range from 17.0 to 23.2 $MPa^{0.5}$, particularly preferably in the range from 18.5 to 21.0 $MPa^{0.5}$;
$H_p$ (polar contribution) in the range from 0.2 to 12.5 $MPa^{0.5}$, particularly preferably in the range from 2.0 to 6.0 $MPa^{0.5}$, and
$H_h$ (hydrogen bonding contribution) in the range from 0.9 to 14.2 $MPa^{0.5}$, particularly preferably in the range from 2.0 to 6.0 $MPa^{0.5}$. The Hansen solubility parameters can be determined using the "Hansen Solubility Parameters in Practice (HSPiP)" computer program ($2^{nd}$ Edition), provided by Hansen and Abbot et al.

Preferred functional compounds of the formula (I) may contain two, three or more of the solubility-promoting structural elements B. Accordingly, the index k in formula (I) can preferably be an integer greater than or equal to 2, particularly preferably greater than or equal to 3.

Surprising advantages can be achieved, in particular, using functional compounds of the general formula (I) having a relatively high molecular weight. Thus, preferred functional compounds of the general formula (I) are distinguished by a molecular weight of at least 800 g/mol, particularly preferably at least 900 g/mol and very particularly preferably at least 950 g/mol.

Furthermore, preferred functional compounds of the formula (I) can have a molecular weight of at most 10,000 g/mol, particularly preferably at most 5000 g/mol and very particularly preferably at most 3000 g/mol.

Of particular interest are furthermore functional compounds which are distinguished by a high glass-transition temperature. In this connection, particular preference is given to functional compounds of the general formula (I) which have a glass-transition temperature of at least 70° C., particularly preferably at least 100° C., very particularly preferably at least 125° C. and especially preferably at least 150° C., determined in accordance with DIN 51005.

The functional structural element A of the functional compound of the formula (I) is not subject to any particular limitation, and consequently the present invention is suitable for converting known substances which are employed in electronic devices in order to achieve functional properties into a soluble form without thereby modifying the original electronic properties of the known substances in an unacceptable manner.

These are, inter alia, those as disclosed and extensively listed in WO 02/077060 A1 and in WO 2005/014689 A2. These are considered to be part of the present invention by way of reference. The functional structural elements A can originate, for example, from the following classes:

Group 1: units which are able to generate hole-injection and/or hole-transport properties;
Group 2: units which are able to generate electron-injection and/or electron-transport properties;
Group 3: units which have light-emitting properties;
Group 4: units which can serve as host materials or co-host materials;
Group 5: units which improve the transfer from the so-called singlet state to the triplet state.

Structural elements from group 1 which have hole-injection and/or hole-transport properties are, for example, triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives and further O-, S- or N-containing heterocycles having a high HOMO (HOMO=highest occupied molecular orbital).

As structural elements from group 1 which have hole-injection and/or hole-transport properties, particular mention may be made of phenylenediamine derivatives (U.S. Pat. No. 3,615,404), arylamine derivatives (U.S. Pat. No. 3,567,450), amino-substituted chalcone derivatives (U.S. Pat. No. 3,526,501), styrylanthracene derivatives (JP-A-56-46234), polycyclic aromatic compounds (EP 1009041), polyarylalkane derivatives (U.S. Pat. No. 3,615,402), fluorenone derivatives (JP-A-54-110837), hydrazone derivatives (U.S. Pat. No. 3,717,462), acylhydrazones, stilbene derivatives (JP-A-61-210363), silazane derivatives (U.S. Pat. No. 4,950,950), polysilanes (JP-A-2-204996), aniline copolymers (JP-A-2-282263), thiophene oligomers (JP Heisei 1 (1989) 211399), polythiophenes, poly(N-vinylcarbazole) (PVK), polypyrroles, polyanilines and other electrically conducting macromolecules, porphyrin compounds (JP-A-63-2956965, U.S. Pat. No. 4,720,432), aromatic dimethylidene-type compounds, carbazole compounds, such as, for example, CDBP, CBP, mCP, aromatic tertiary amine and styrylamine compounds (U.S. Pat. No. 4,127,412), such as, for example, triphenylamines of the benzidine type, triphenylamines of the styrylamine type and triphenylamines of the diamine type. It is also possible to use arylamine dendrimers (JP Heisei 8 (1996) 193191), monomeric triarylamines (U.S. Pat. No. 3,180,730), triarylamines containing one or more vinyl radicals and/or at least one functional group containing active hydrogen (U.S. Pat. Nos. 3,567,450 and 3,658,520), or tetraaryl-diamines (the two tertiary amine units are connected via an aryl group). More triarylamino groups may also be present in the molecule. Phthalocyanine derivatives, naphthalocyanine derivatives, butadiene derivatives and quinoline derivatives, such as, for example, dipyrazino[2,3-f:2',3'-h]quinoxalinehexacarbonitrile, are also suitable.

Preference is given to aromatic tertiary amines containing at least two tertiary amine units (US 2008/0102311 A1, U.S. Pat. Nos. 4,720,432 and 5,061,569), such as, for example, NPD (α-NPD=4,4'-bis[N-(1-naphthyl)-N-phenylamino]biphenyl) (U.S. Pat. No. 5,061,569), TPD 232 (=N,N'-bis-(N,N'-diphenyl-4-aminophenyl)-N,N-diphenyl-4,4'-diamino-1,1'-biphenyl) or MTDATA (MTDATA or m-MTDATA=4,4',4''-tris[3-methylphenyl)phenylamino]-triphenylamine) (JP-A-4-308688), TBDB (=N,N,N',N'-tetra(4-biphenyl)-diaminobiphenylene), TAPC(=1,1-bis(4-di-p-tolylaminophenyl)cyclo-hexane), TAPPP (=1,1-bis(4-di-p-tolylaminophenyl)-3-phenylpropane), BDTAPVB (=1,4-bis[2-[4-[N, N-di(p-tolyl)amino]phenyl]vinyl]benzene), TTB (=N,N,N',N'-tetra-p-tolyl-4,4'-diaminobiphenyl), TPD (=4,4'-bis[N-3-methylphenyl]-N-phenylamino)biphenyl), N, N, N',N'-tetraphenyl-4,4'''-diamino-1,1',4',1'',4'',1'''-quaterphenyl, likewise tertiary amines containing carbazole units, such as, for example, TCTA (=4-(9H-carbazol-9-yl)-N,N-bis[4-(9H-carbazol-9-yl)phenyl]benzenamine). Preference is likewise given to hexaazatriphenylene compounds in accordance with US 2007/0092755 A1 and phthalocyanine derivatives (for example H$_2$Pc, CuPc (=copper phthalocyanine), CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, GaPc-O-GaPc).

TPD 232

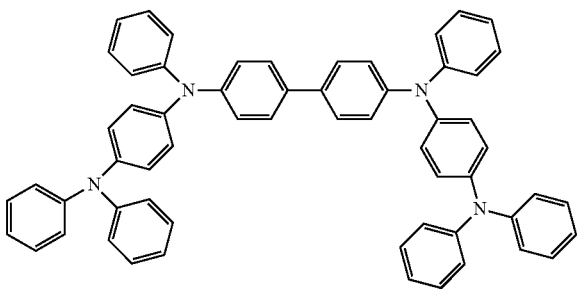

Particular preference is given to the following triarylamine compounds, which may also be substituted:
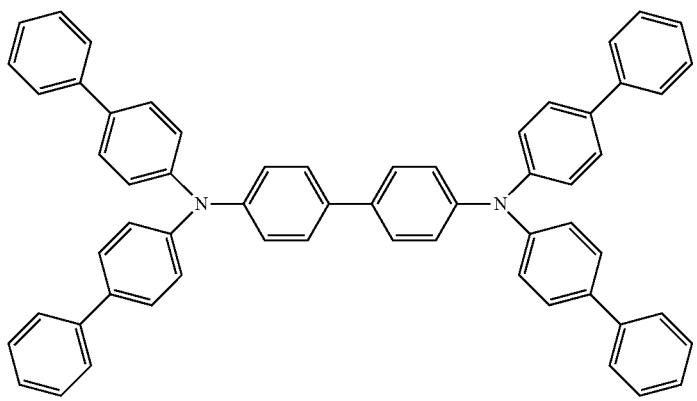
TBDB: EP 1162193 B1 and EP 650955 B1
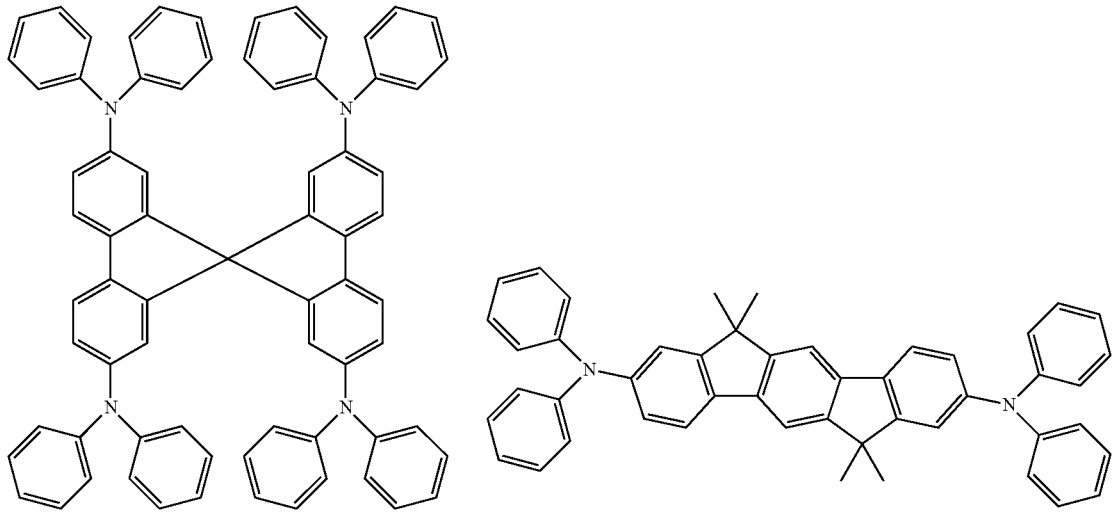
Synth. Metals 1197, 91 (1-3), 209 and DE 19646119 A1
WO 2006 122630 A1 and EP 1860097 A1
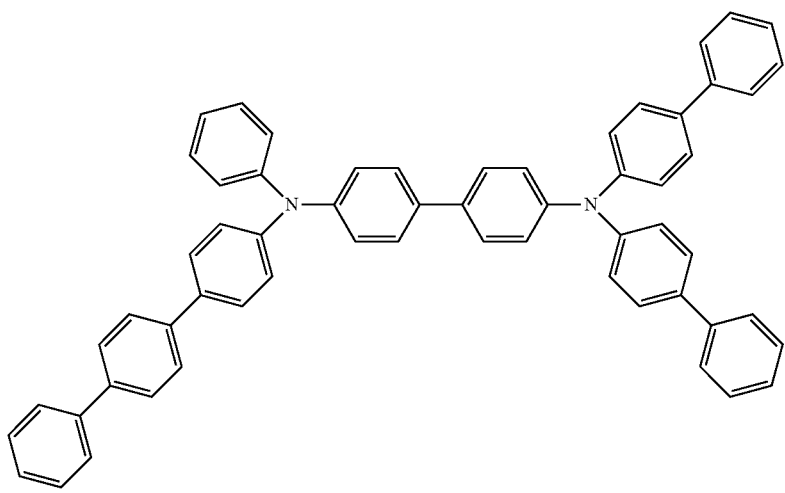
EP 1834945 A1

-continued
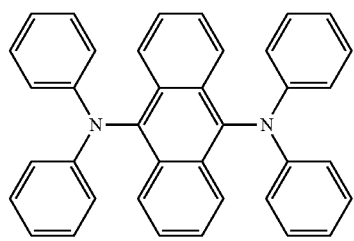
JP 08053397 A and U.S. Pat. No. 6,251,531 B1
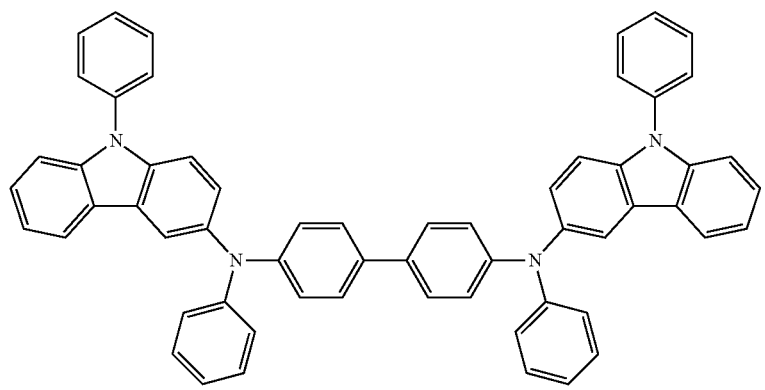
EP 1661888
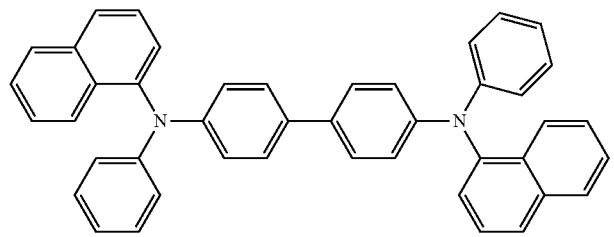
NPB = alpha-NPD
NPB = 4,4′-bis[N-(1-naphthy)-N-phenylamino]biphenyl
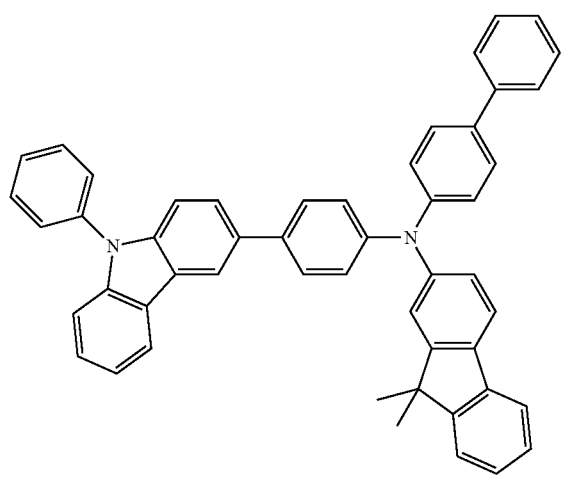
U.S. 2005/0221124, WO 09/041635

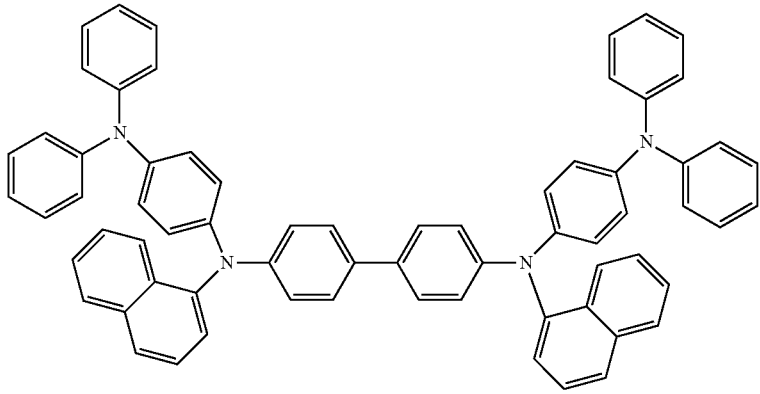

U.S. Pat. No. 7,399,537 B2, U.S. 2006 0061265 A1

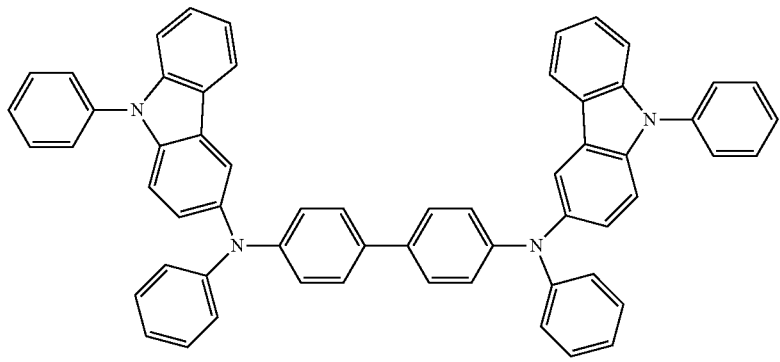

EP 1661888 B1

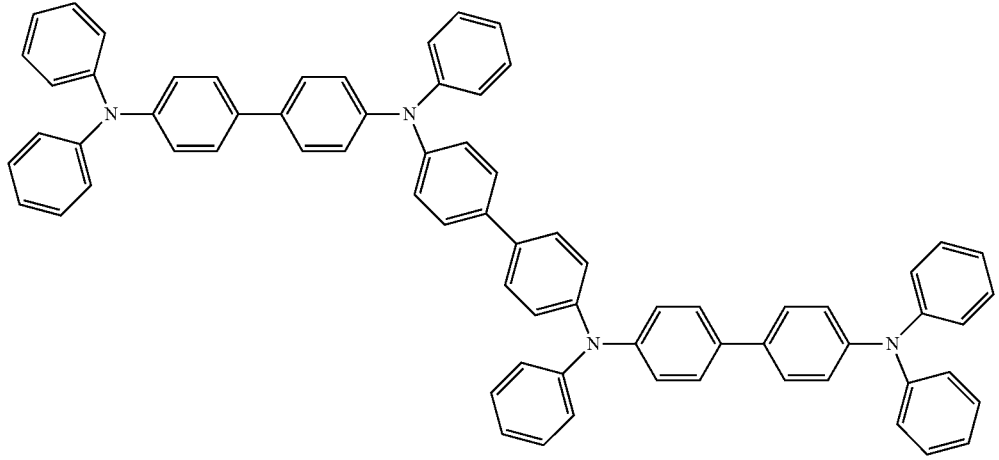

JP 08292586 A

Further structural elements which can be employed as hole-injection materials are described in EP 0891121 A1 and EP 1029909 A1, injection layers in general in US 2004/0174116 A1.

These arylamines and heterocycles which are generally employed as structural elements from group 1 preferably result in an HOMO in the polymer of greater than −5.8 eV (vs. vacuum level), particularly preferably greater than −5.5 eV.

Structural elements from group 2 which have electron-injection and/or electron-transport properties are, for example, pyridine, pyrimidine, pyridazine, pyrazine, oxadiazole, quinoline, quinoxaline, anthracene, benzanthracene, pyrene, perylene, benzimidazole, triazine, ketone, phosphine oxide and phenazine derivatives, but also triarylboranes and further O-, S- or N-containing heterocycles having a low LUMO (LUMO=lowest unoccupied molecular orbital).

Particularly suitable structural elements for electron-transporting and electron-injecting layers are metal chelates of 8-hydroxyquinoline (for example LiQ, $AlQ_3$, $GaQ_3$, $MgQ_2$, $ZnQ_2$, $InQ_3$, $ZrQ_4$), BAlQ, Ga oxinoid complexes, 4-azaphenanthren-5-ol-Be complexes (U.S. Pat. No. 5,529,853 A),

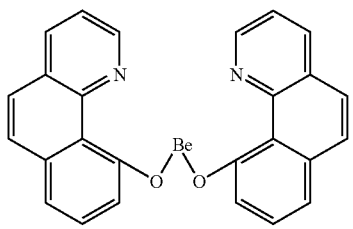

butadiene derivatives (U.S. Pat. No. 4,356,429), heterocyclic optical brighteners (U.S. Pat. No. 4,539,507), benzimidazole derivatives (US 2007/0273272 A1), such as, for example, TPBI (U.S. Pat. No. 5,766,779),

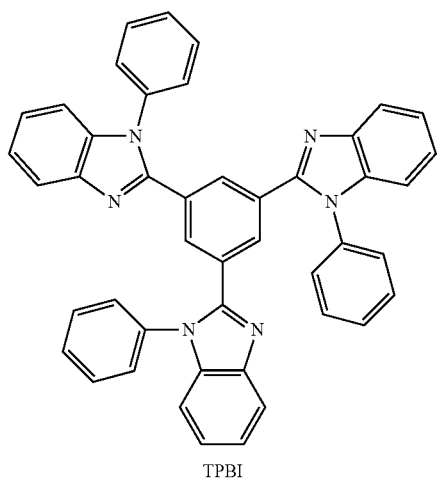

TPBI
2,2′,2″-(1,3,5-benzenetriyl)tris(1-phenyl-1H-benzimidazole)

1,3,5-triazines, for example spirobifluorenyltriazine derivatives (for example in accordance with DE 102008064200), pyrenes, anthracenes, tetracenes, fluorenes, spirofluorenes, dendrimers, tetracenes (for example rubrene derivatives), 1,10-phenanthroline derivatives (JP 2003-115387, JP 2004-311184, JP-2001-267080, WO 2002/043449), silacyclopentadiene derivatives (EP 1480280, EP 1478032, EP 1469533), borane derivatives, such as, for example, triarylborane derivatives containing Si,

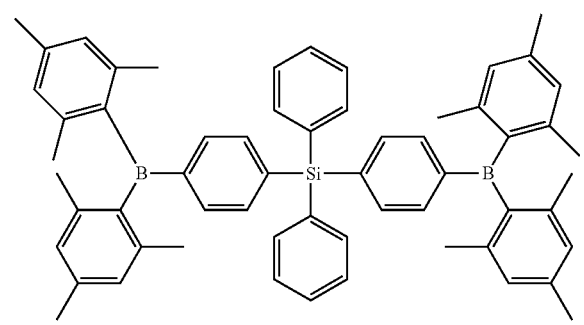

U.S. 2007/0087219 A1 pyridine derivatives (JP 2004-200162), phenanthrolines, especially 1,10-phenanthroline derivatives, such as, for example, BCP and Bphen, also several phenanthrolines connected via biphenyl or other aromatic groups (US-2007-0252517 A1) or phenanthrolines connected to anthracene (US 2007-0122656 A1).

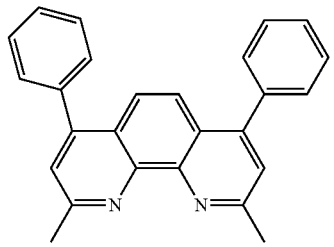

Bathocuproin

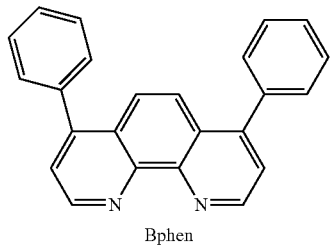

Bphen

Likewise suitable are heterocyclic organic compounds, such as, for example, thiopyran dioxides, oxazoles, triazoles, imidazoles or oxadiazoles. Examples of the use of five-membered rings containing N, such as, for example, oxazoles, thiazoles, oxadiazoles, thiadiazoles, triazoles, inter alia, see US 2008/0102311 A1. Preferred compounds are the following: triazoles, for example

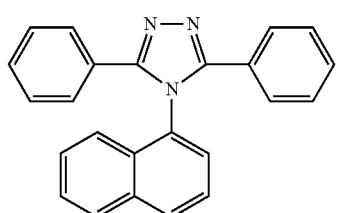

Y. A. Levin, M. S. Skorobogatova, Khimiya Geterotsiklicheskikh Soedinenii 1967 (2), 339-341.

1,3,4-oxadiazoles, for example

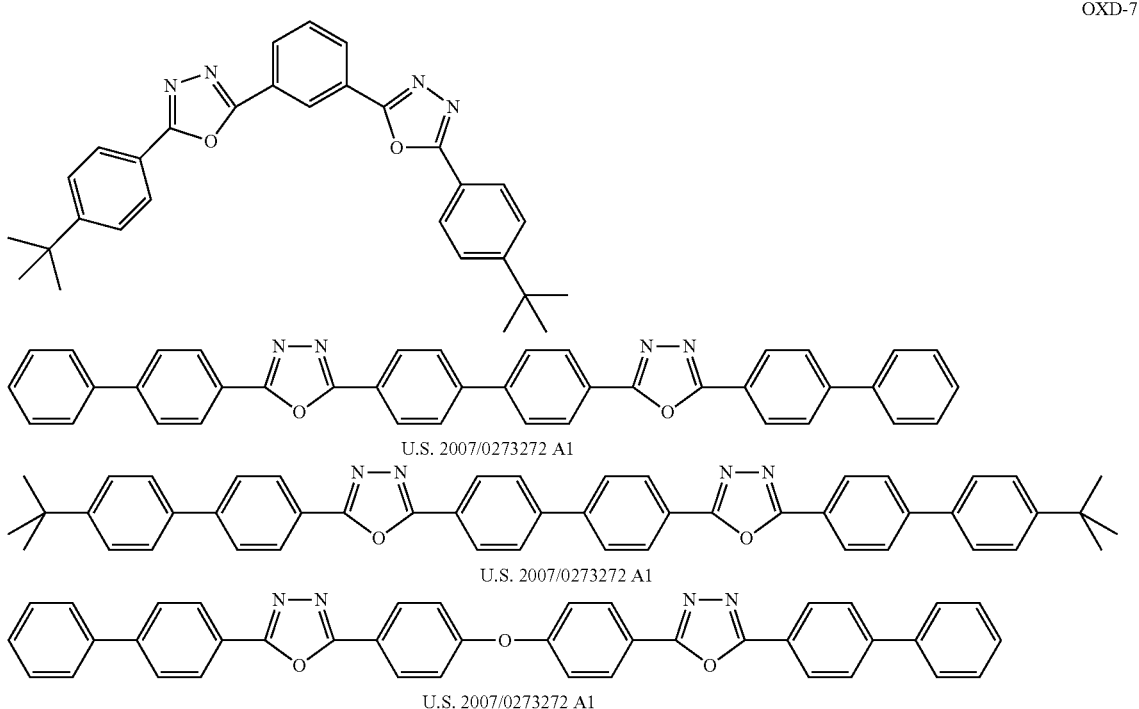

It is also possible to employ organic compounds, such as derivatives of fluorenone, fluorenylidenemethane, perylenetetracarbonic acid, anthraquinonedimethane, diphenoquinone, anthrone and anthraquinone-diethylenediamine.

Preference is given to 2,9,10-substituted anthracenes (with 1- or 2-naphthyl and 4- or 3-biphenyl) or molecules which contain two anthracene units (US2008/0193796 A1). Also very advantageous is the connection of 9,10-substituted anthracene units to benzimidazole derivatives.

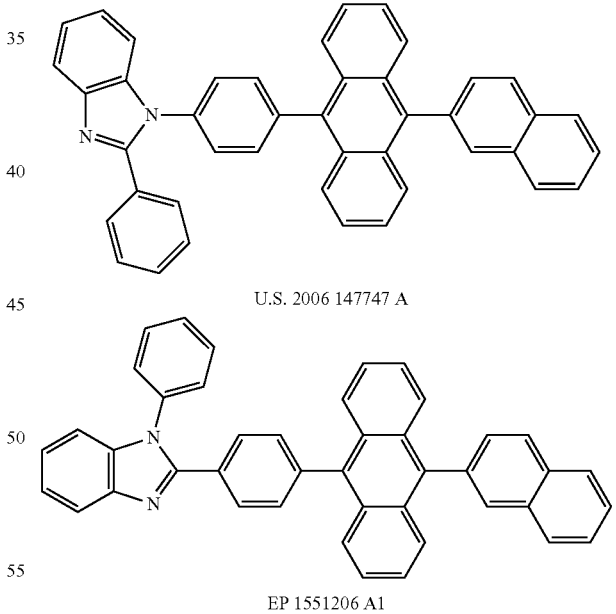

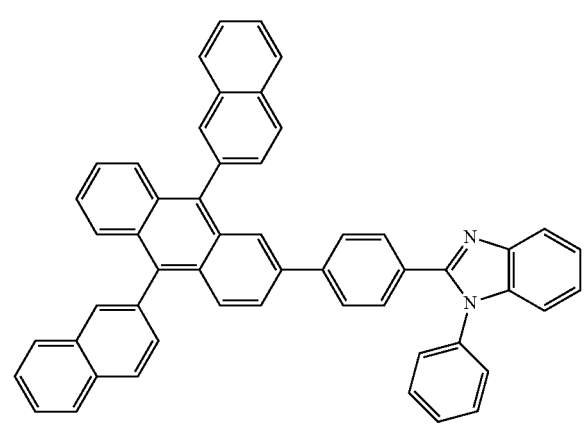

The structural elements from group 2 in a compound of the formula (I) to be employed in accordance with the invention preferably result in an LUMO of less than −2.5 eV (vs. vacuum level), particularly preferably less than −2.7 eV.

Structural elements from group 3 are those which are able to emit light. These include, inter alia, compounds containing stilbene, stilbenamine, styrylamine, coumarine, rubrene, rhodamine, thiazole, thiadiazole, cyanine, thiophene, paraphenylene, perylene, phatalocyanine, porphyrin, ketone, quinoline, imine, anthracene and/or pyrene structures. Particular preference is given to compounds which are able to emit light from the triplet state with high efficiency, even at room temperature, i.e. exhibit electro-phosphorescence instead of electrofluorescence, which frequently causes an increase in the energy efficiency. Suitable for this purpose are firstly compounds which contain heavy atoms having an atomic number of greater than 36. Preference is given to compounds which contain d- or f-transition metals which satisfy the above-mentioned condition. Particular preference is given here to corresponding structural elements which contain elements from group 8 to 10 (Ru, Os, Rh, Ir, Pd, Pt). Suitable functional structural elements A for the compounds of the formula (I) here are, for example, various complexes, as described, for example, in WO 02/068435 A1, WO 02/081488 A1, EP 1239526 A2 and WO 04/026886 A2.

Preferred structural elements which can serve as fluorescent emitters are described by way of example below. Preferred structural elements from group 3 are selected from the class of the monostyrylamines, the distyryl-amines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or an aromatic amine in the sense of the present invention is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracenamines, aromatic anthracene-diamines, aromatic pyrenamines, aromatic pyrenediamines, aromatic chrysenamines or aromatic chrysenediamines. An aromatic anthracen-amine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 2,6- or 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Further preferred structural elements from group 3 are selected from indenofluorenamines or indenofluorenediamines, for example in accordance with WO 06/122630, benzoindenofluorenamines or benzoindeno-fluorenediamines, for example in accordance with WO 08/006449, and dibenzoindenofluorenamines or dibenzoindenofluorenediamines, for example in accordance with WO 07/140847.

Examples of structural elements from group 3 from the class of the styrylamines are substituted or unsubstituted tristilbenamines or the dopants described in WO 06/000388, WO 06/058737, WO 06/000389, WO 07/065549 and WO 07/115610. Distyrylbenzene and distyrylbiphenyl derivatives are described in U.S. Pat. No. 5,121,029. Further styrylamines can be found in US 2007/0122656 A1.

Particularly preferred styrylamine structural elements from group 3 are:

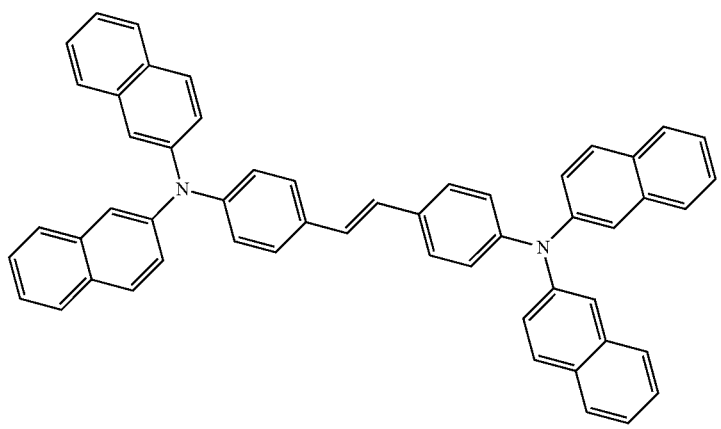

U.S. Pat. No. 7,250,532 B2

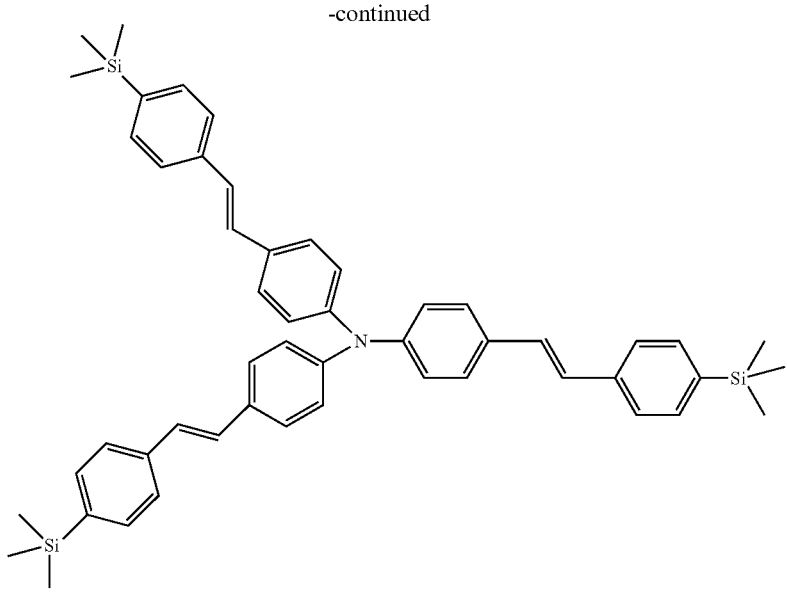
DE 10 2005 058557 A1
Particularly preferred triarylamine structural elements from group 3 are:
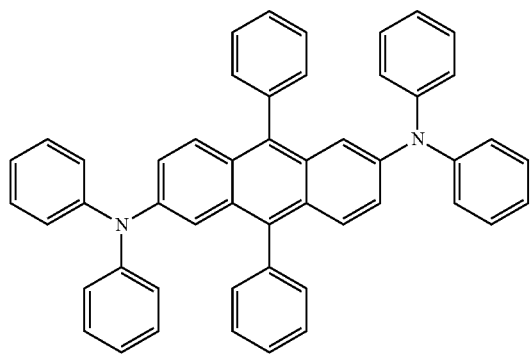
CN 1583691 A
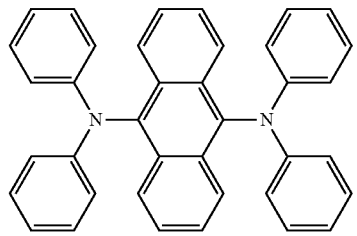
JP 08/053397 A and U.S. Pat. No. 6,251,531 B1, derivatives in EP 1957606 A1 and US 2008/0113101 A1.
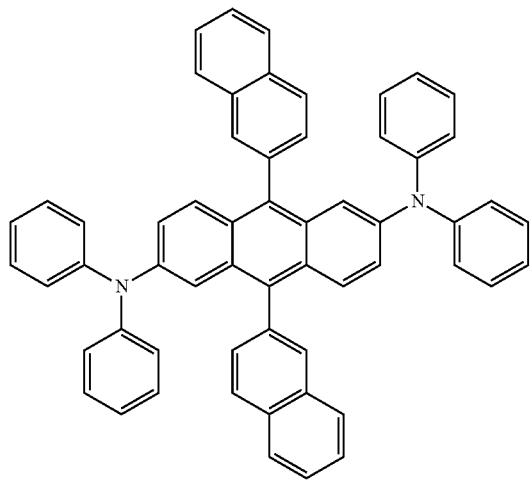
CN 1583691 A
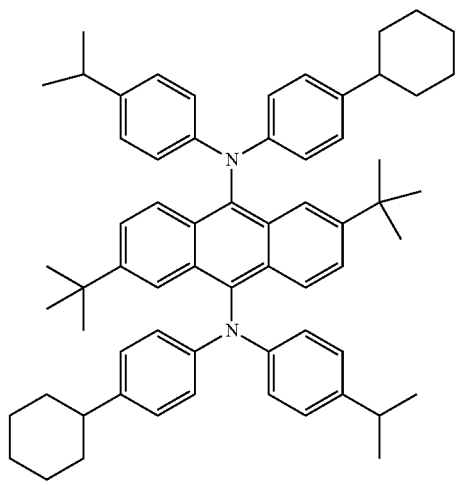
EP 1957606 A1

-continued

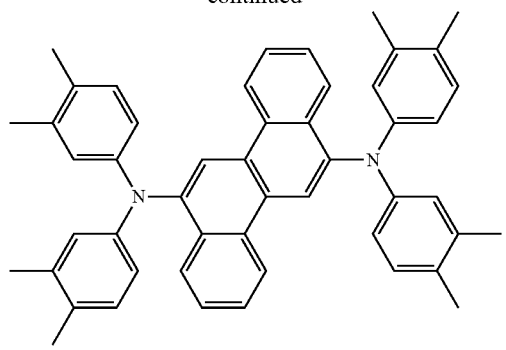

U.S. 2006/210830 A

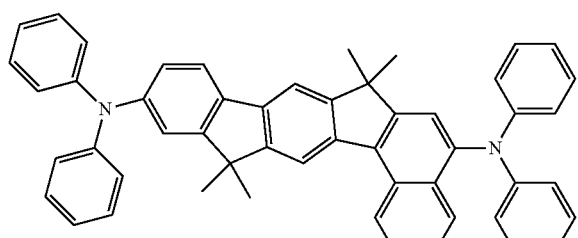

WO 08/006449

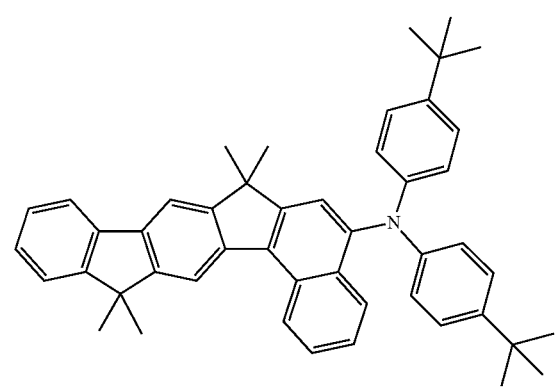

WO 08/006449

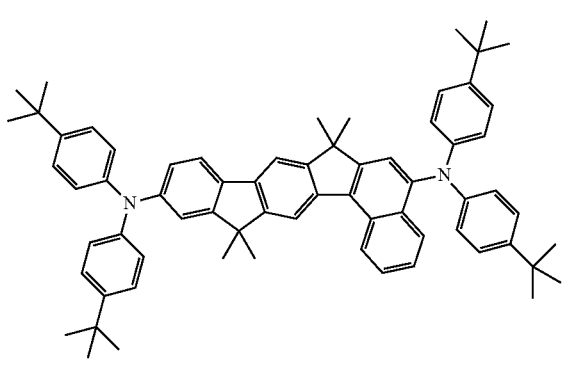

WO 08/006449

-continued

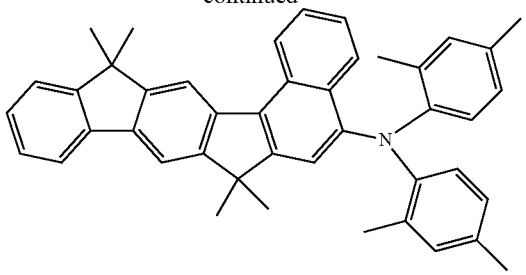

WO 08/006449

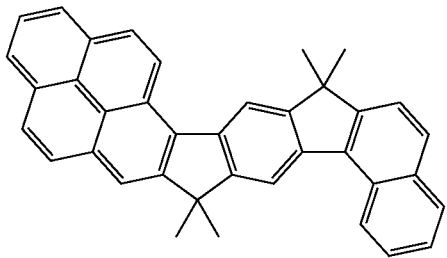

DE 102008035413

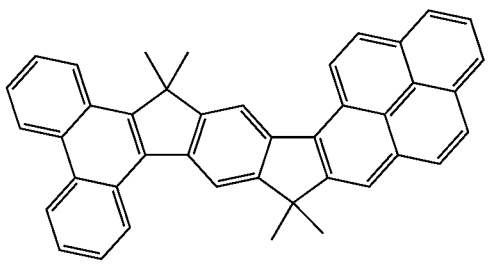

DE 102008035413

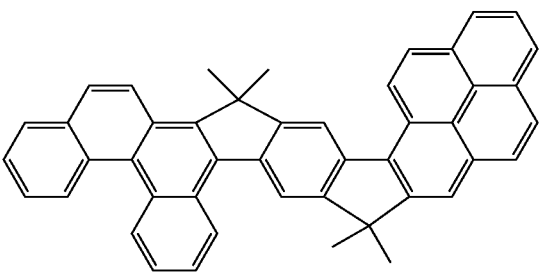

DE 102008035413

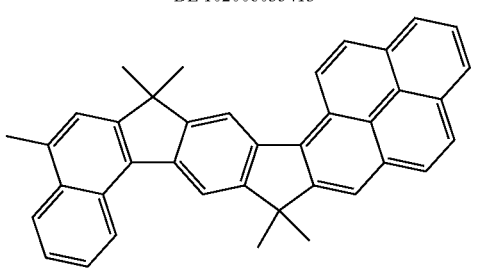

DE 102008035413

Further preferred structural elements from group 3 are selected from derivatives of naphthalene, anthracene, tetracene, benzanthracene, benzophenanthrene (DE 10 2009 005746), fluorene, fluoranthene, periflanthene, indenoperylene, phenanthrene, perylene (US 2007/0252517 A1), pyrene, chrysene, decacyclene, coronene, tetraphenylcyclopentadiene, pentaphenylcyclopentadiene, fluorene, spirofluorene, rubrene, coumarine (U.S. Pat. Nos. 4,769,292, 6,020,078, US 2007/0252517 A1), pyran, oxazole, benzoxazole, benzothiazole, benzimidazole, pyrazine, cinnamic acid esters, diketopyrrolopyrrole, acridone and quinacridone (US 2007/0252517 A1).

Of the anthracene compounds, particular preference is given to 9,10-substituted anthracenes, such as, for example, 9,10-diphenylanthracene and 9,10-bis(phenylethynyl)anthracene. 1,4-Bis(9'-ethynylanthracenyl)benzene is also a preferred dopant.

Preference is likewise given to derivatives of rubrene, coumarine, rhodamine, quinacridone, such as, for example, DMQA (=N,N'-dimethylquinacri-done), dicyanomethylenepyran, such as, for example, DCM (=4-(dicyano-ethylene)-6-(4-dimethylaminostyryl-2-methyl)-4H-pyran), thiopyran, polymethine, pyrylium and thiapyrylium salts, periflanthene and indenoperylene.

Blue fluorescent emitters are preferably polyaromatic compounds, such as, for example, 9,10-di(2-naphthylanthracene) and other anthracene derivatives, derivatives of tetracene, xanthene, perylene, such as, for example, 2,5,8,11-tetra-t-butylperylene, phenylene, for example 4,4'-bis(9-ethyl-3-carbazovinylene)-1,1'-biphenyl, fluorene, fluoranthene, arylpyrenes (US 2006/0222886 A1), arylenevinylenes (U.S. Pat. Nos. 5,121,029, 5,130,603), bis-(azinyl)imine-boron compounds (US 2007/0092753 A1), bis (azinyl)methene compounds and carbostyryl compounds.

Further preferred blue fluorescent emitters are described in C. H. Chen et al.: "Recent developments in organic electroluminescent materials" Macro-mol. Symp. 125, (1997) 1-48 and "Recent progress of molecular organic electroluminescent materials and devices" Mat. Sci. and Eng. R, 39 (2002), 143-222.

Further preferred blue-fluorescent emitters are the hydrocarbons disclosed in DE 102008035413.

Preferred structural elements from group 3 which can serve as phosphorescent emitters are depicted by way of example below.

Examples of phosphorescent emitters are revealed by WO 00/70655, WO 01/41512, WO 02/02714, WO 02/15645, EP 1191613, EP 1191612, EP 1191614 and WO 05/033244. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

Phosphorescent metal complexes preferably contain Ir, Ru, Pd, Pt, Os or Re.

Preferred ligands are 2-phenylpyridine derivatives, 7,8-benzoquinoline derivatives, 2-(2-thienyl)pyridine derivatives, 2-(1-naphthyl)pyridine derivatives, 1-phenylisoquinoline derivatives, 3-phenylisoquinoline derivatives or 2-phenylquinoline derivatives. All these compounds may be substituted, for example by fluoro, cyano and/or trifluoromethyl substituents for blue. Auxiliary ligands are preferably acetylacetonate or picolinic acid.

Particularly suitable are complexes of Pt or Pd with tetradentate ligands,

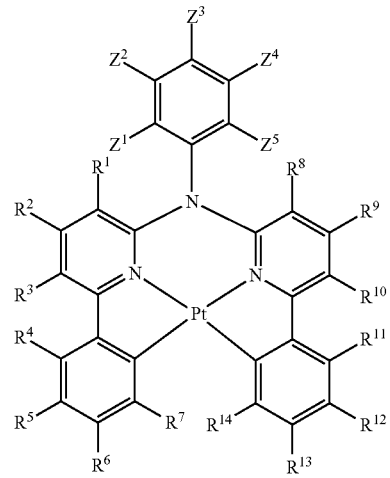

(US 2007/0087219 A1, where, for disclosure purposes, reference is made to this specification for an explanation of the substituents and indices in the above formula), Pt-porphyrin complexes having an enlarged ring system (US 2009/0061681 A1) and Ir complexes, for example 2,3,7,8, 12,13,17,18-octaethyl-21H, 23H-porphyrin-Pt(II), tetraphenyl-Pt(II) tetrabenzoporphyrin (US 2009/0061681 A1), cis-bis(2-phenylpyridinato-N,$C^{2'}$)Pt(II), cis-bis(2-(2'-thienyl) pyridinato-N,$C^{3'}$)Pt(II), cis-bis(2-(2'-thienyl)quinolinato-N, $C^{5'}$)Pt(I), (2-(4,6-difluorophenyl)pyridinato-N,$C^{2'}$)Pt(II) (acetylacetonate), or tris(2-phenylpyridinato-N,$C^{2'}$)Ir(II) (=Ir(ppy)$_3$, green), bis(2-phenylpyridinato-N,$C^2$)Ir(III) (acetylacetonate) (=Ir(ppy)$_2$ acetylacetonate, green, US 2001/0053462 A1, Baldo, Thompson et al. Nature 403, (2000), 750-753), bis(1-phenylisoquinolinato-N,$C^{2'}$)(2-phenylpyridinato-N,$C^{2'}$)iridium(II), bis(2-phenylpyridinato-N, $C^{2'}$)(1-phenylisoquinolinato-N,$C^{2'}$)iridium(III), bis(2-(2'-benzothienyl))pyridinato-N,$C^{3'}$)iridium(l II) (acetylacetonate), bis(2-(4',6'-difluorophenyl)pyridinato-N, $C^{2'}$)iridium(III) (piccolinate) (Flrpic, blue), bis(2-(4',6'-difluorophenyl)pyridinato-N,$C^{2'}$)Ir(III) (tetrakis(1-pyrazolyl) borate), tris(2-(biphenyl-3-yl)-4-tert-butylpyridine)iridium (III), (ppz)$_2$Ir(5phdpym) (US 2009/0061681 A1), (45ooppz)$_2$ Ir(5phdpym) (US 2009/0061681 A1), derivatives of 2-phenylpyridine-Ir complexes, such as, for example, PQIr (=iridium(III) bis(2-phenylquinolyl-N, $C^{2'}$) acetylacetonate), tris(2-phenyliso-quinolinato-N,C)Ir(III) (red), bis(2-(2'-benzo[4,5-a]thienyl)pyridinato-N,$C^3$)Ir (acetylacetonate) ([Btp$_2$Ir(acac)], red, Adachi et al. Appl. Phys. Lett. 78 (2001), 1622-1624).

Likewise suitable are complexes of trivalent lanthanides, such as, for example, Tb$^{3+}$ and Eu$^{3+}$ (J. Kido et al. Appl. Phys. Lett. 65 (1994), 2124, Kido et al. Chem. Lett. 657, 1990, US 2007/0252517 A1), or phosphorescent complexes of Pt(II), Ir(I), Rh(I) with maleonitrile dithiolate (Johnson et al., JACS 105, 1983, 1795), Re(I) tricarbonyl-diimine complexes (Wrighton, JACS 96, 1974, 998, inter alia), Os(II) complexes with cyano ligands and bipyridyl or phenanthroline ligands (Ma et al., Synth. Metals 94, 1998, 245).

Further phosphorescent emitters having tridentate ligands are described in U.S. Pat. No. 6,824,895 and U.S. Ser. No. 10/729,238. Red-emitting phosphorescent complexes are found in U.S. Pat. Nos. 6,835,469 and 6,830,828.

Particularly preferred structural elements which are used as phosphorescent dopants are:

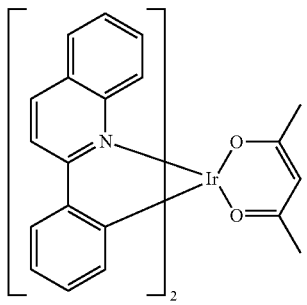

US 2001/0053462 A1 and *Inorg. Chem.* 2001, 40(7), 1704-1711, JACS 2001, 123(18), 4304-4312.

Derivatives are described in U.S. Pat. No. 7,378,162 B2, U.S. Pat. No. 6,835,469 B2 and JP 2003/253145 A.

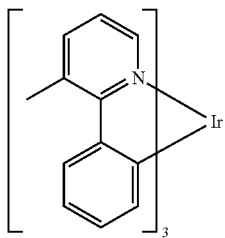

U.S. Pat. No. 7,238,437 B2

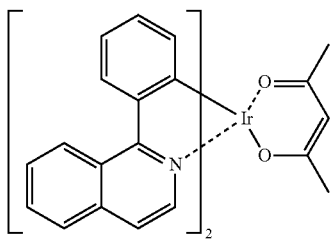

U.S. 2009/008607 A1

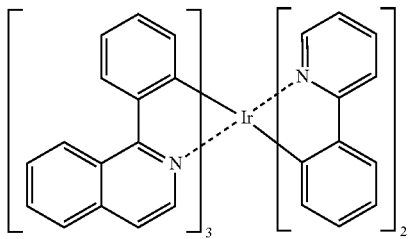

U.S. 2009/008607 A1

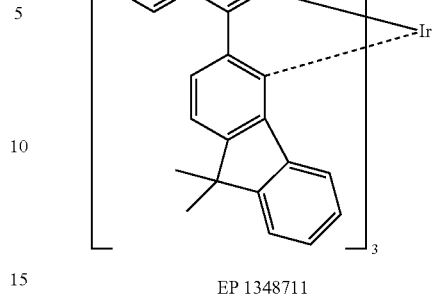

EP 1348711

Structural elements from group 4 which are employed as host materials, in particular together with emitting compounds, include materials from various classes of substance.

Preferred structural elements from group 4 which are employed, in particular, together with fluorescent dopants are selected from the classes of the oligoarylenes (for example 2,2',7,7'-tetraphenylspirobifluorene in accordance with EP 676461 or dinaphthylanthracene), in particular the oligoarylenes containing condensed aromatic groups, such as, for example, anthracene, benzanthracene, benzophenanthrene (DE 10 2009 005746, WO 09/069566), phenanthrene, tetracene, coronene, chrysene, fluorene, spirofluorene, perylene, phthaloperylene, naphthaloperylene, decacyclene, rubrene, the oligoarylenevinylenes (for example DPVBi=4, 4'-bis(2,2-diphenylethenyl)-1, 1'-biphenyl or spiro-DPVBi in accordance with EP 676461), the polypodal metal complexes (for example in accordance with WO 04/081017), in particular metal complexes of 8-hydroxyquinoline, for example AlQ$_3$ (=aluminium(III) tris(8-hydroxyquinoline)) or bis(2-methyl-8-quinolinolato)-4-(phenylphenolinolato) aluminium, also with imidazole chelate (US 2007/0092753 A1) and the quinoline-metal complexes, amino-quinoline-metal complexes, benzoquinoline-metal complexes, the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145239).

Particularly preferred structural elements from group 4 are selected from the classes of the oligoarylenes, comprising anthracene, benzanthracene and/or pyrene, or atropisomers of these compounds. An oligoarylene in the sense of the present invention is intended to be taken to mean a compound in which at least three aryl or arylene groups are bonded to one another.

Preferred host materials are selected, in particular, from compounds of the formula (H-1), $$Ar^3—(Ar^4)_p—Ar^5 \quad (H\text{-}1)$$

where $Ar^3$, $Ar^4$, $Ar^5$ is on each occurrence, identically or differently, an aryl or heteroaryl group having 5 to 30 aromatic ring atoms, which may be substituted by one or more radicals $R^1$, and $R^1$ has the same meaning as described above, and p represents an integer in the range from 1 to 5; the sum of the π electrons in $Ar^3$, $Ar^4$ and $Ar^5$ is at least 30 if p=1 and at least 36 if p=2 and at least 42 if p=3.

In the compounds of the formula (H-1), the group Ar⁴ particularly preferably stands for anthracene, which may be substituted by one or more radicals R¹, and the groups Ar³ and Ar⁵ are bonded in the 9- and 10-position. Very particularly preferably, at least one of the groups Ar³ and/or Ar⁵ is a condensed aryl group selected from 1- or 2-naphthyl, 2-, 3- or 9-phenanthrenyl or 2-, 3-, 4-, 5-, 6- or 7-benzanthracenyl, each of which may be substituted by one or more radicals R¹. Anthracene-based compounds are described in US 2007/0092753 A1 and US 2007/0252517 A1, for example 2-(4-methylphenyl)-9,10-di-(2-naphthyl)anthracene, 9-(2-naphthyl)-10-(1,1'-biphenyl)-anthracene and 9,10-bis[4-(2,2-diphenylethenyl)phenyl]anthracene, 9,10-diphenylanthracene, 9,10-bis(phenylethynyl)anthracene and 1,4-bis(9'-ethynylanthracenyl)benzene. Preference is also given to compounds containing two anthracene units (US 2008/0193796 A1), for example 10,10'-bis[1,1',4',1''']terphenyl-2-yl-9,9'-bisanthracenyl.

Further preferred compounds are derivatives of arylamine, styrylamine, fluorescein, diphenylbutadiene, tetraphenylbutadiene, cyclopentadienes, tetraphenylcyclopentadiene, pentaphenylcyclopentadiene, coumarine, oxadiazole, bisbenzoxazoline, oxazole, pyridine, pyrazine, imine, benzothiazole, benzoxazole, benzimidazole (US 2007/0092753 A1), for example 2,2',2''-(1,3,5-phenylene)tris[1-phenyl-1H-benzimidazole], aldazine, stilbene, styrylarylene derivatives, for example 9,10-bis[4-(2,2-diphenyl-ethenyl)phenyl]anthracene, and distyrylarylene derivatives (U.S. Pat. No. 5,121,029), diphenylethylene, vinylanthracene, diaminocarbazole, pyran, thiopyran, diketopyrrolopyrrole, polymethine, cinnamic acid esters and fluorescent dyes.

Particular preference is given to derivatives of arylamine and styrylamine, for example TNB (=4,4'-bis[N-(1-naphthyl)-N-(2-naphthyl)amino]biphenyl). Metal-oxinoid complexes, such as LiQ or AlQ₃, can be used as co-hosts.

Preferred compound with oligoarylene as matrix:

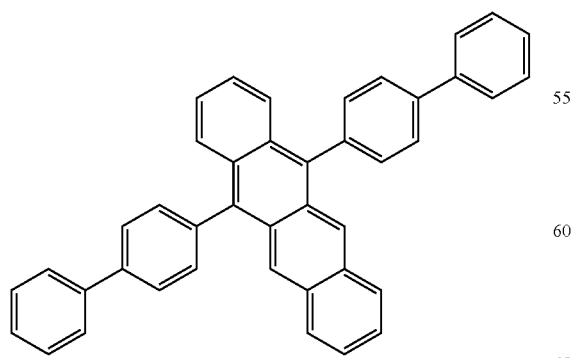

U.S. 2003/0027016 A1

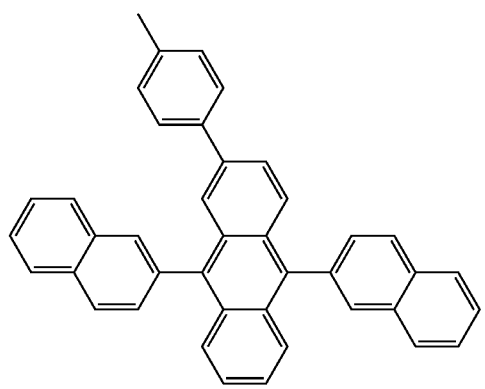

U.S. Pat. No. 7,326,371 B2

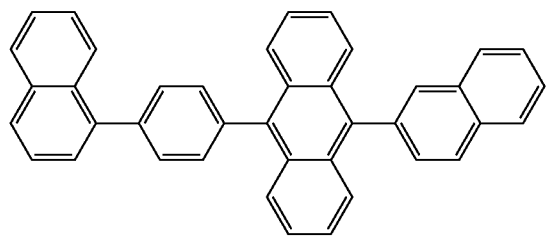

U.S. 2006/043858 A

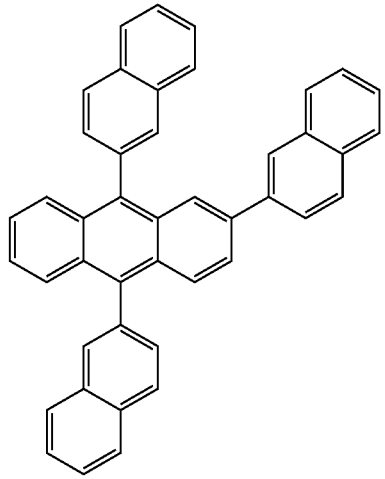

U.S. Pat. No. 7,326,371 B2

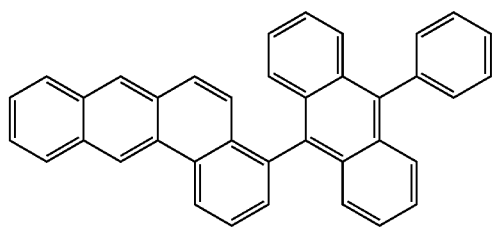

WO 08/145239

-continued

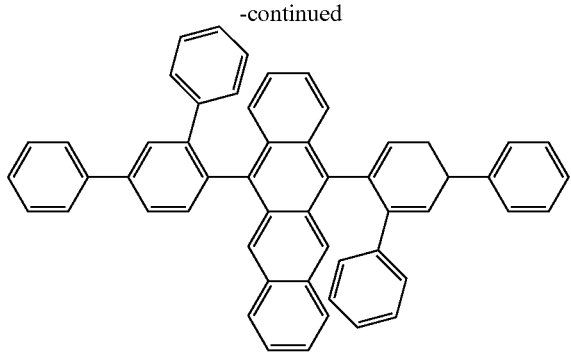

U.S. 2003/0027016 A1

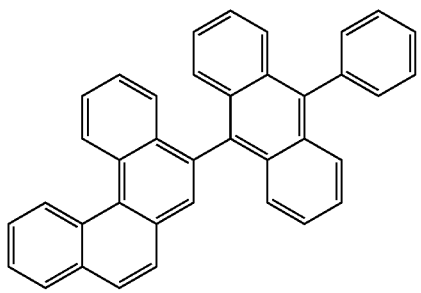

DE 102009005746

Furthermore, structural elements from group 4 include materials which are employed together with phosphorescent emitters. These structural elements include CBP (N,N-bis-carbazolylbiphenyl), carbazole derivatives (for example in accordance with WO 05/039246, US 2005/0069729, JP 2004/288381, EP 1205527 or WO 08/086851), azacarbazoles (for example in accordance with EP 1617710, EP 1617711, EP 1731584, JP 2005/347160), ketones (for example in accordance with WO 04/093207 or in accordance with DE 102008033943), phosphine oxides, sulfoxides and sulfones (for example in accordance with WO 05/003253), oligophenylenes, aromatic amines (for example in accordance with US 2005/0069729), bipolar matrix materials (for example in accordance with WO 07/137725), silanes (for example in accordance with WO 05/111172), 9,9-diarylfluorene derivatives (for example in accordance with DE 102008017591), azaboroles or boronic esters (for example in accordance with WO 06/117052), triazine derivatives (for example in accordance with DE 102008036982), indolocarbazole derivatives (for example in accordance with WO 07/063754 or WO 08/056746), indenocarbazole derivatives (for example in accordance with DE 102009023155 and DE 102009031021), diazaphosphole derivatives (for example in accordance with DE 102009022858), triazole derivatives, oxazoles and oxazole derivatives, imidazole derivatives, polyarylalkane derivatives, pyrazoline derivatives, pyrazolone derivatives, distyrylpyrazine derivatives, thiopyran dioxide derivatives, phenylenediamine derivatives, tertiary aromatic amines, styrylamines, amino-substituted chalcone derivatives, indoles, hydrazone derivatives, stilbene derivatives, silazane derivatives, aromatic dimethylidene compounds, carbodiimide derivatives, metal complexes of 8-hydroxyquinoline derivatives, such as, for example, $AlQ_3$, which may also contain triarylaminophenol ligands (US 2007/0134514 A1), metal complex/poly-silane compounds, and thiophene, benzothiophene and dibenzothiophene derivatives.

Examples of preferred carbazole structural elements are mCP (=1,3-N,N-dicarbazolylbenzene (=9,9'-(1,3-phenylene)bis-9H-carbazole)), CDBP (=9,9'-(2,2'-dimethyl[1,1'-biphenyl]-4,4'-diyl)bis-9H-carbazole), 1,3-bis(N,N'-dicarbazolyl)benzene (=1, 3-bis(carbazol-9-yl)benzene), PVK (polyvinyl-carbazole), 3,5-di(9H-carbazol-9-yl)biphenyl, and the compounds depicted below.

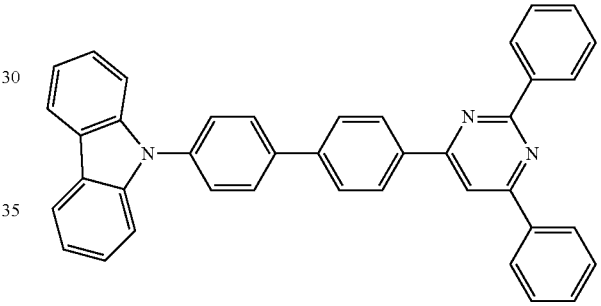

mCP

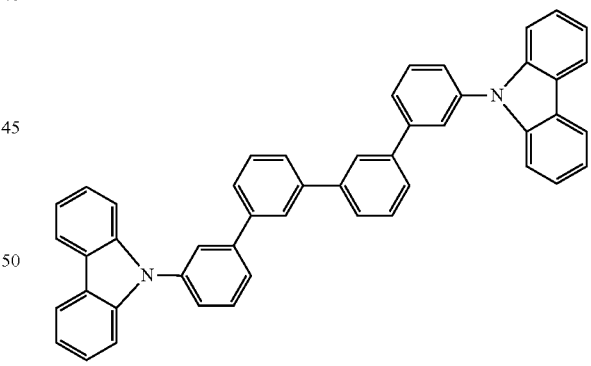

U.S. 2005/02499796 A1

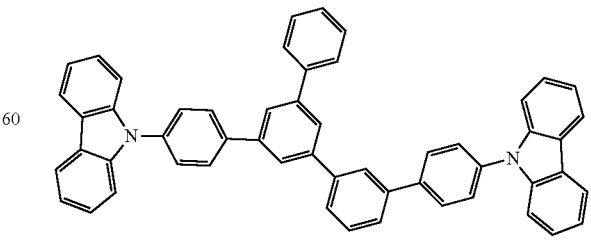

CMTTP

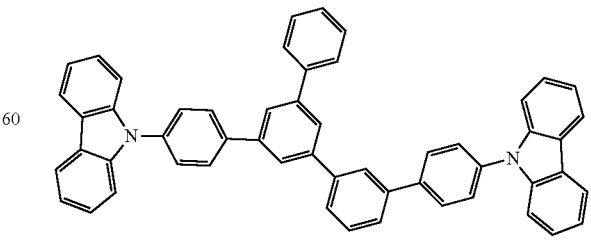

U.S. 2007/0128467 A1

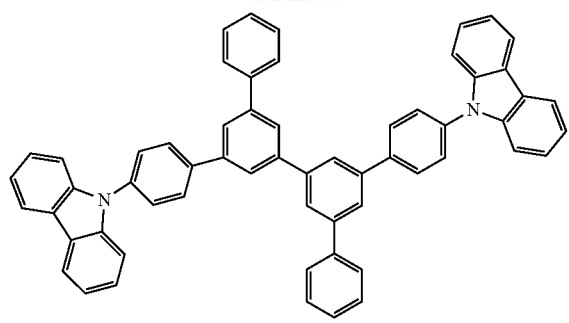
U.S. 2007/0128467 A1
Preferred Si tetraaryl compounds are, for example, (US 2004/0209115, US 2004/0209116)
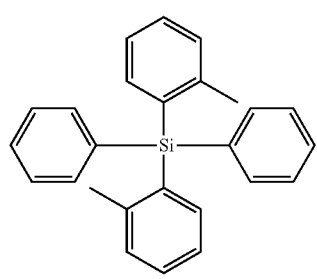
UGH1
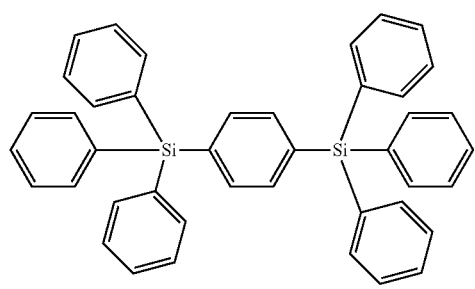
UGH2
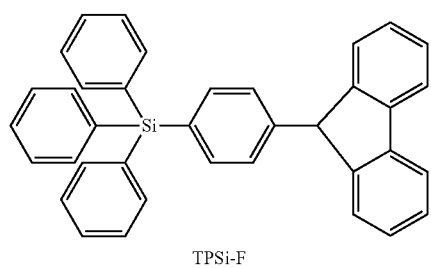
UGH4
TPSi-F
Triphenyl-[4-(9-phenyl-9H-fluoren-9-yl)phenyl]silane
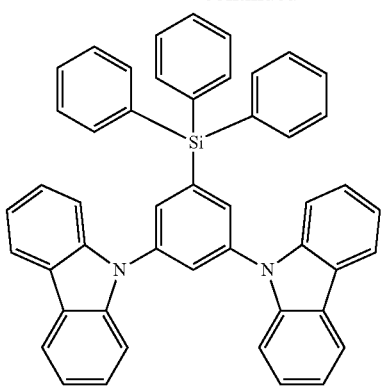
SimCP
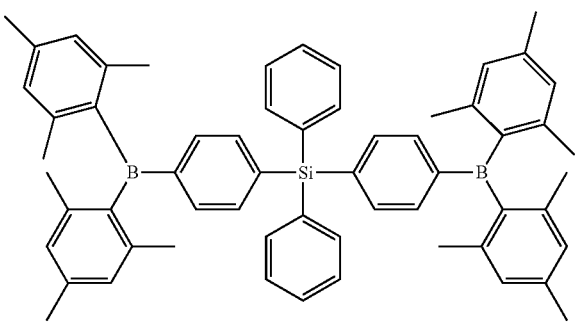
U.S. 2007/0087219 A1
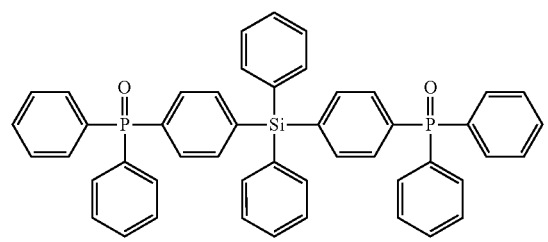
U.S. 2007/0087219 A1
H. Gilman, E. A. Zuech, Chemistry & Industry (London, United Kingdom), 1960, 120.

Particularly preferred structural elements from group 4 for the preparation of the matrix for phosphorescent dopants are:

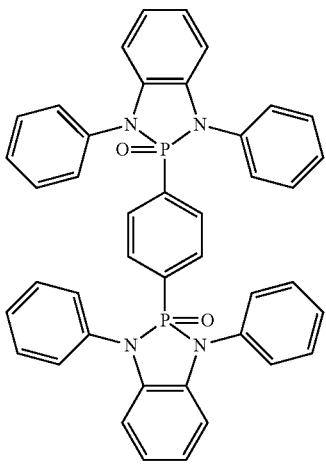

DE 102009022858

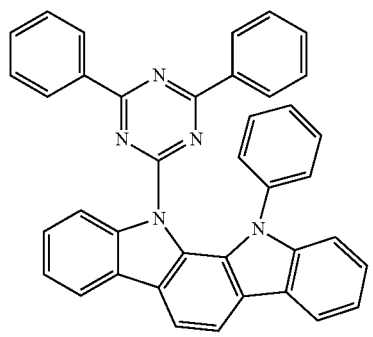

WO 07/063754 and WO 08/056746

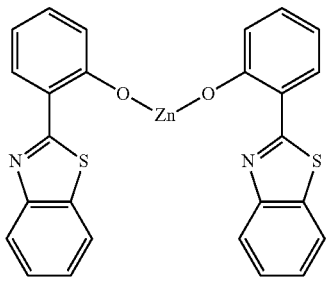

EP 652273 B1

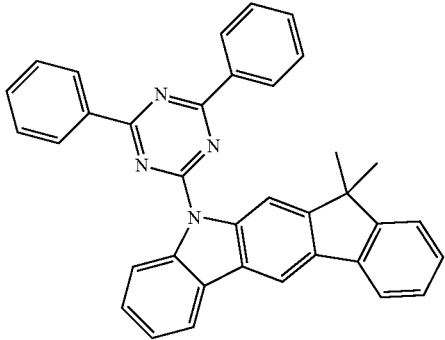

DE 102009023155

With respect to the functional compounds which can be employed in accordance with the invention and which can serve as host material, particular preference is given to substances whose functional structural element A has at least one nitrogen atom. These preferably include aromatic amines, triazine derivatives and carbazole derivatives. Thus, carbazole derivatives in particular exhibit surprisingly high efficiency. Triazine derivatives unexpectedly result in long lifetimes of the electronic devices comprising the said compounds.

Structural elements from group 5 are those which improve the transfer from the singlet state to the triplet state and which, employed in support of the functional structural elements from group 3, improve the phosphorescence properties of these structural elements. Suitable for this purpose are, in particular, carbazole and bridged carbazole dimer units, as described, for example, in WO 04/070772 A2 and WO 04/113468 A1. Also suitable for this purpose are ketones, phosphine oxides, sulfoxides, sulfones, silane derivatives and similar compounds, as described, for example, in WO 05/040302 A1.

The publications cited above for the description of the functional structural elements are incorporated into the present application by way of reference for disclosure purposes.

The functional structural elements A described above can preferably be connected to at least one solubility-promoting structural element B via an aromatic and/or heteroaromatic group. The bonding site is generally not important, meaning that one or more bonds to at least one of the solubility-promoting structural elements B described below are present, but are not depicted in the formulae shown above for reasons of clarity. According to a particular aspect, the functional structural elements A described above can be connected to one or more solubility-promoting structural elements B via a carbon atom of an aromatic or heteroaromatic ring system.

Besides at least one functional structural element A, a compound according to the invention contains at least one solubility-promoting structural element B of the formula (L-I)

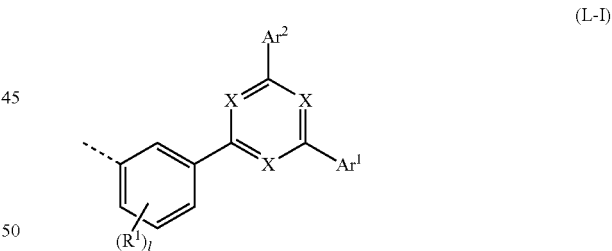

where

Ar$^1$, Ar$^2$ is each, independently of one another, an aryl or heteroaryl group, which may be substituted by one or more radicals R of any desired type, X is in each case, independently of one another, N or CR$^2$, preferably CH, R$^1$, R$^2$ is each, independently of one another, hydrogen, a straight-chain alkyl, alkenyl, alkoxy or thioalkoxy group having 1 or 2 to 40 C atoms respectively or a branched or cyclic alkyl, alkenyl, alkoxy or thioalkoxy group having 3 to 40 C atoms or is a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—

X, in which X represents a halogen atom), a formyl group (—C(=O)—H), an isocyano group, an isocyanate group, a thiocyanate group or a thioisocyanate group, a hydroxyl group, a nitro group, a $CF_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$ and/or $R^2$ may form a mono- or polycyclic, aliphatic or aromatic ring system with one another and/or with the ring to which the group $R^1$ is bonded; and l is 0, 1, 2, 3 or 4;

where the dashed bond indicates the bond to the functional structural element A.

The solubility-promoting structural element B can preferably conform to the general formula (L-II)

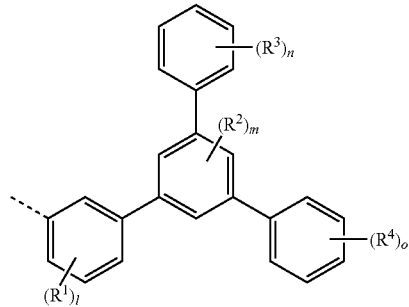
(L-II)

where $R^1$, $R^2$, $R^3$, $R^4$ is each, independently of one another, hydrogen, a straight-chain alkyl, alkenyl, alkoxy or thioalkoxy group having 1 or 2 to 40 C atoms respectively or a branched or cyclic alkyl, alkenyl, alkoxy or thioalkoxy group having 3 to 40 C atoms or is a silyl group or a substituted keto group having 1 to 40 C atoms, an alkoxycarbonyl group having 2 to 40 C atoms, an aryloxycarbonyl group having 7 to 40 C atoms, a formyl group (—C(=O)—H), a $CF_3$ group, Cl, Br, F, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where one or more of the groups $R^1$, $R^2$, $R^3$ and/or $R^4$ may form a mono- or polycyclic, aliphatic or aromatic ring system with one another and/or with the ring to which the group $R^1$ is bonded; and l is 0, 1, 2, 3 or 4, m is 0, 1, 2 or 3, and n, o is each, independently of one another, 0, 1, 2, 3, 4 or 5;

where the dashed bond indicates the bond to the functional structural element.

The radicals $R^1$, $R^2$, $R^3$, $R^4$ particularly preferably represent hydrogen (l, m, n and o=0), a straight-chain alkyl or alkoxy group having 1 to 20 C atoms or a branched alkyl or alkoxy group having 3 to 20 C atoms.

The particularly preferred solubility-promoting structural elements B include, inter alia, the structural elements of the following formulae:

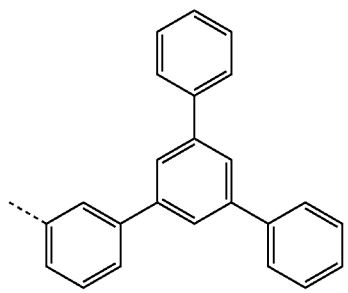
(L-IIa)

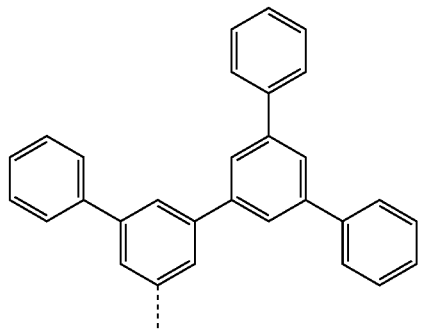
(L-IIb)

where the dashed bond indicates the bond to the functional structural element A.

Very particular preference is given to the following solubility-promoting structural elements B:

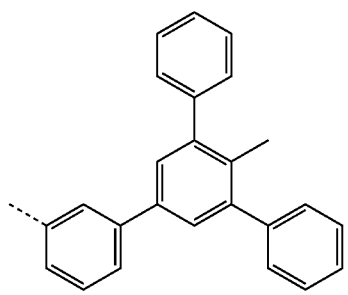
(L-IIa1)

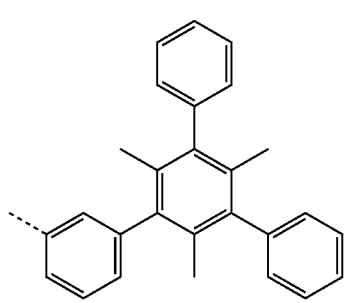
(L-IIa2)

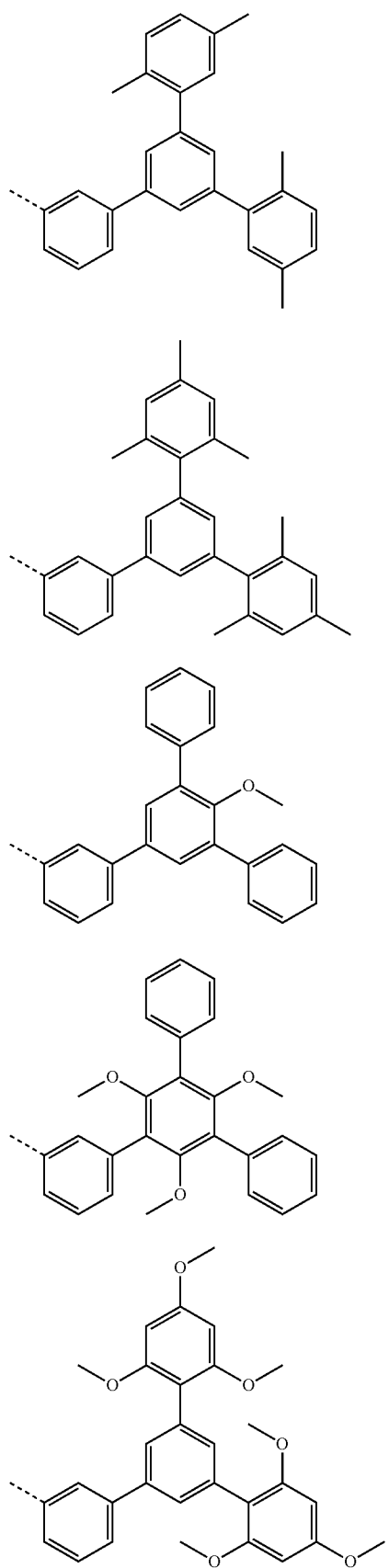
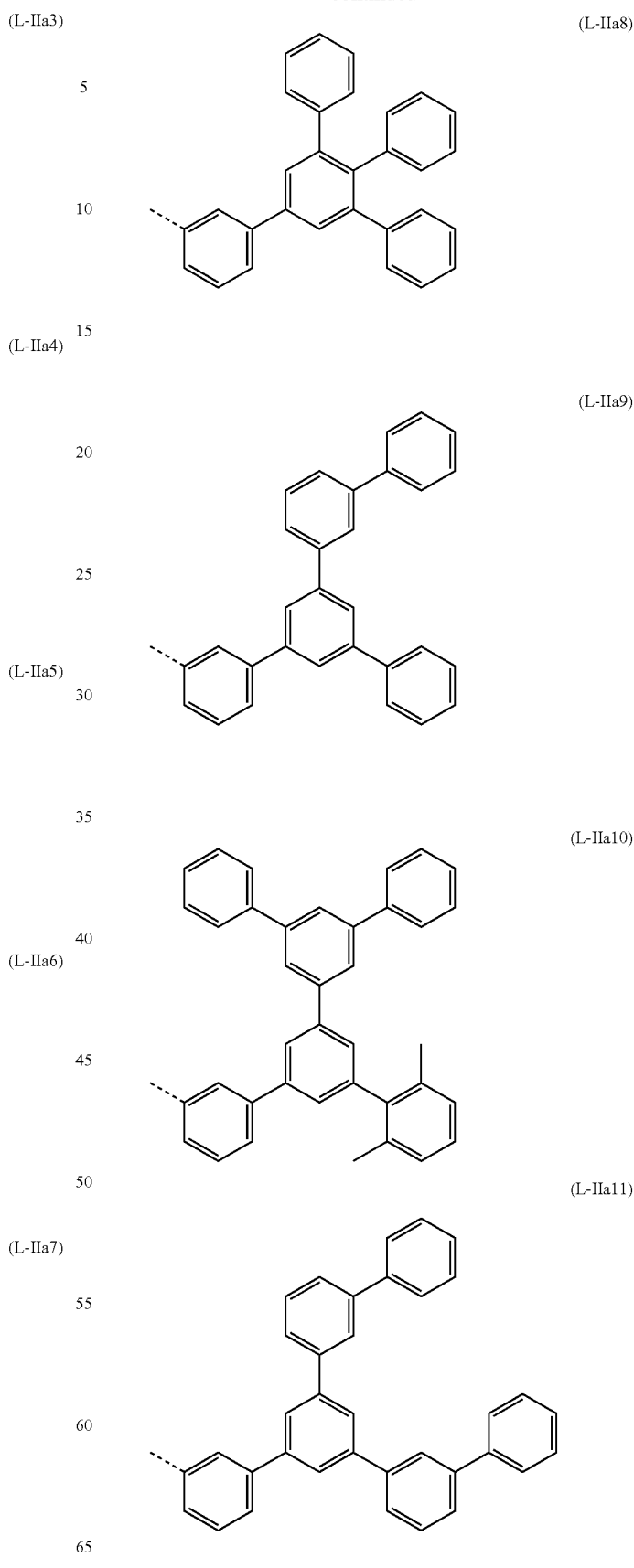

-continued

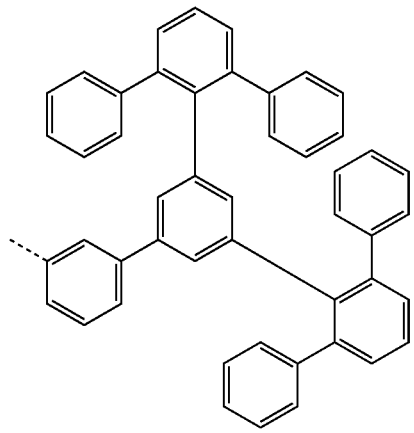
(L-IIa12)

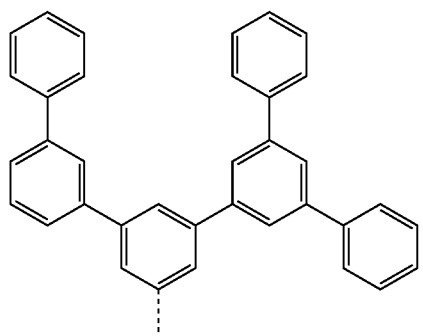
(L-IIb1)

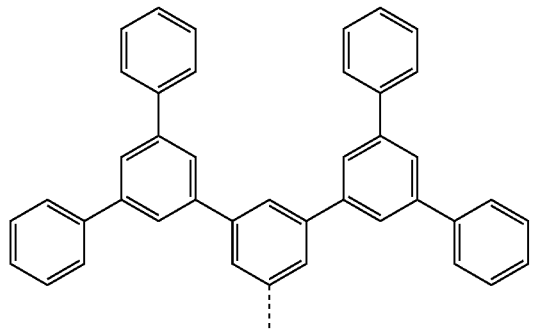
(L-IIb2)

where the dashed bond indicates the bond to the functional A structural element.

An aromatic or heteroaromatic ring system having 5 to 60 ring atoms, which may also in each case be substituted by any desired radicals R and which may be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothio-phene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phen-anthrimidazole, pyridimidazole, pyrazinimidazole, quinoxalinimidazole, oxazole, benzoxazole, naphthoxazole, anthroxazole, phenanthroxazole, isoxa-zole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetra-zole, 1,2,4,5-tetrazine, 1,2,3,4-tetrazine, 1,2,3,5-tetrazine, purine, pteridine, indolizine, benzothiadiazole, benzanthrene, benzanthracene, rubicene and triphenylene. For the purposes of the present invention, particular preference is given to fluorene, spirobifluorene, indenofluorene, anthracene, phenanthrene, dihydrophenanthrene and carbazole.

An aryl group in the sense of the present invention contains 5 to 60 C atoms; a heteroaryl group in the sense of the present invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, or a condensed aryl or heteroaryl group, for example naphthalene, anthracene, phenanthrene, quinoline, isoquinoline, benzothiophene, benzofuran and indole.

In the structural units of the general formulae (L-I) and (L-II), it is furthermore preferred for $R^1$ and $R^2$, and $R^1$, $R^2$, $R^3$ and $R^4$ respectively to be selected on each occurrence, independently of one another, from F, Cl, Br, I, $N(Ar)_2$, $N(R')_2$, CN, $NO_2$, $Si(R')_3$, $B(OR')_2$, C(=O)Ar, C(=O)R', P(=O)(Ar)$_2$, P(=O)(R')$_2$, S(=O)Ar, S(=O)R', S(=O)$_2$Ar, S(=O)$_2$R', —CR'=CR'Ar, $OSO_2R'$, a straight-chain alkyl, alkoxy or thioalkoxy group having 1 to 40 C atoms, preferably 1 to 20 C atoms, or a branched or cyclic alkyl, alkoxy or thioalkoxy group having 3 to 40 C atoms, preferably 3 to 20 C atoms, each of which may be substituted by one or more radicals R', where one or more non-adjacent $CH_2$ groups may be replaced by R'C=CR', C≡C, Si(R')$_2$, Ge(R')$_2$, Sn(R')$_2$, C=O, C=S, C=Se, C=NR', P(=O)(R'), SO, $SO_2$, NR', O, S or CONR' and where one or more H atoms may be replaced by F, Cl, Br, I, CN or $NO_2$, a crosslinkable group or an aromatic or heteroaromatic ring system having 5 to 60 ring atoms, which may in each case be substituted by one or more radicals R', or an aryloxy or heteroaryloxy group having 5 to 60 ring atoms, which may be substituted by one or more radicals R', or a combination of these systems, where two or more substituents R may also form a mono- or polycyclic, aliphatic or aromatic ring system with one another, where R' is in each case, independently of one another, H or an aliphatic or aromatic hydrocarbon radical having 1 to 20 C atoms, and Ar is an aryl or heteroaryl groups having 2 to 30 C atoms.

The structural units of the general formulae (L-I) and (L-II) may, as described above, contain one or more crosslinkable groups. "Crosslinkable group" means a functional group which is capable of reacting irreversibly. A crosslinked material, which is insoluble, is thereby formed. The crosslinking can usually be supported by heat or by UV, microwave, X-ray or electron radiation. Little by-product formation occurs during the crosslinking here. In addition, the crosslinkable groups which may be present in the functional compounds crosslink very easily, meaning that smaller amounts of energy are necessary for the crosslinking (for example <200° C. in the case of thermal crosslinking).

Examples of crosslinkable groups are units which contain a double bond, a triple bond, a precursor which is capable of in-situ formation of a double or triple bond, or a heterocyclic addition-polymerisable radical. Crosslinkable groups include, inter alia, vinyl, alkenyl, preferably ethenyl and propenyl, $C_{4-20}$-cycloalkenyl, azide, oxirane, oxetane, di(hydrocarbyl)amino, cyanate ester, hydroxyl, glycidyl ether, $C_{1-10}$-alkyl acrylate, $C_{1-10}$-alkyl methacrylate, alkenyloxy, preferably ethenyloxy, perfluoroalkenyloxy, preferably perfluoro-ethenyloxy, alkynyl, preferably ethynyl, maleimide, tri($C_{1-4}$)-alkylsiloxy and tri($C_{1-4}$)-alkylsilyl. Particular preference is given to vinyl and alkenyl.

For the purposes of the present invention, an alkyl group having 1 to 40 C atoms, in which, in addition, individual H atoms or $CH_2$ groups may be substituted by the above-mentioned groups or radicals R, is preferably taken to mean the radicals methyl, ethyl, n-propyl, i-propyl, cyclopropyl, n-butyl, i-butyl, s-butyl, t-butyl, cyclobutyl, 2-methylbutyl, n-pentyl, s-pentyl, cyclo-pentyl, n-hexyl, cyclohexyl, n-heptyl, cycloheptyl, n-octyl, cyclooctyl, 2-ethyl-hexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl and octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy or 2-methylbutoxy.

According to a particular aspect of the present invention, the weight ratio of structural element A to structural element B in formula (I) is preferably in the range from 2:1 to 1:20 and particularly preferably in the range from 1:1 to 1:3.

The functional compounds of the formula (I) present in the formulations according to the invention can be prepared using known methods, in which starting materials containing reactive groups are reacted. These reactive starting materials contain the above-described structural units of the above formulae and at least in each case one leaving group, such as, for example, bromine, iodine, boronic acid or boronic acid ester.

Suitable reactions for the formation of C—C links are known to the person skilled in the art and are described in the literature. Particularly suitable and preferred coupling reactions, all of which result in C—C links, are SUZUKI, YAMAMOTO, STILLE, HECK, NEGISHI, SONOGASHIRA and HIYAMA coupling reactions.

The particularly preferred functional compounds include compounds of the formulae (V-Ia), (V-Ib), (V-Ic) and (V-Id)

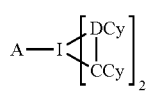

formula V-Ia

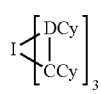

formula V-Ib

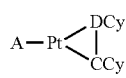

formula V-Ic

formula V-Id where the following applies to the symbols used:

DCy is, identically or differently on each occurrence, a cyclic group which contains at least one donor atom, preferably nitrogen, carbon in the form of a carbene, or phosphorus, via which the cyclic group is bonded to the metal, and which may in turn carry one or more substituents $R^{10}$; the groups DCy and CCy are connected to one another via a covalent bond;

CCy is, identically or differently on each occurrence, a cyclic group which contains a carbon atom via which the cyclic group is bonded to the metal and which may in turn carry one or more substituents $R^{10}$;

A is, identically or differently on each occurrence, a mono-anionic, bidentate-chelating ligand, preferably a diketonate ligand;

$R^{10}$ is on each occurrence, identically or differently, H, D, F, Cl, Br, I, CHO, C(=O)$Ar^3$, P(=O)($Ar^3$)$_2$, S(=O)$Ar^3$, S(=O)$_2Ar^3$, $CR^{11}$=$CR^{11}Ar^3$, CN, $NO_2$, Si($R^{11}$)$_3$, B(OR$^{11}$)$_2$, B($R^{11}$)$_2$, B(N($R^{11}$)$_2$)$_2$, OSO$_2R^{11}$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^{11}$, where one or more non-adjacent $CH_2$ groups may be replaced by $R^{11}C$=$CR^{11}$, C≡C, Si($R^{11}$)$_2$, Ge($R^{11}$)$_2$, Sn($R^{11}$)$_2$, C=O, C=S, C=Se, C=$NR^{11}$, P(=O)($R^{11}$), SO, $SO_2$, $NR^{11}$, O, S or $CONR^{11}$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^{11}$, or an aryloxy or heteroaryloxy group having 5 to 60 aromatic ring atoms, which may be substituted by one or more radicals $R^{11}$, or a combination of these systems; two or more adjacent substituents $R^{10}$ here may also form a mono- or polycyclic, aliphatic or aromatic ring system with one another;

$Ar^3$ is on each occurrence, identically or differently, an aromatic or heteroaromatic ring system having 5 to 40 aromatic ring atoms, which may be substituted by one or more radicals $R^{11}$;

$R^{11}$ is on each occurrence, identically or differently, H, D, CN or an aliphatic, aromatic and/or heteroaromatic hydrocarbon radical having 1 to 20 C atoms, in which, in addition, H atoms may be replaced by F; two or more adjacent substituents $R^{11}$ here may also form a mono- or polycyclic, aliphatic or aromatic ring system with one another, where at least one of the said radicals DCy, CCy and/or A contains at least one group of the formulae (L-I) and/or (L-II).

Due to formation of ring systems between a plurality of radicals $R^{10}$, a bridge may also be present between the groups DCy and CCy. Furthermore, due to formation of ring systems between a plurality of radicals $R^{10}$, a bridge may also be present between two or three ligands CCy-DCy or between one or two ligands CCy-DCy and the ligand A, giving a polydentate or polypodal ligand system respectively.

According to a further, particular embodiment of the present invention, soluble functional compounds, in particular polyacenes of the formula (V-II),

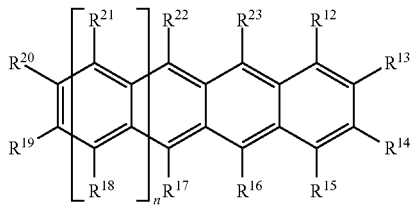

(V-II)

are employed, in which
the radicals $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ is each independently hydrogen, a straight-chain alkyl, alkoxy or thioalkoxy group having 1 to 40 C atoms or a branched or cyclic alkyl, alkoxy or thioalkoxy group having 3 to 40 C atoms or is a silyl group or a substituted keto group having 1 to 40 C atoms, an alkoxycarbonyl group having 2 to 40 C atoms, an aryloxycarbonyl group having 7 to 40 C atoms, a cyano group (—CN), a carbamoyl group (—C(=O)NH$_2$), a haloformyl group (—C(=O)—X, in which X represents a halogen atom), a formyl group (—C(=O)—H), an isocyano group, an isocyanate group, a thiocyanate group or a thioisocyanate group, an amino group, a hydroxyl group, a nitro group, a CF$_3$ group, Cl, Br, F, a crosslinkable group or a substituted or unsubstituted, aromatic or heteroaromatic ring system having 5 to 60 ring atoms, or an aryloxy or heteroaryloxy group having 5 to 60 ring atoms, or a combination of these systems, where one or more of the groups $R^{12}$, $R^{13}$, $R^{14}$, $R^{15}$, $R^{16}$, $R^{17}$, $R^{18}$, $R^{19}$, $R^{20}$, $R^{21}$, $R^{22}$ and/or $R^{23}$ may form a mono- or polycyclic, aliphatic or aromatic ring system with one another and/or with the ring to which the respective group is bonded; and in which each pair $R^{12}$ and $R^{13}$, $R^{13}$ and $R^{14}$, $R^{14}$ and $R^{15}$, $R^{18}$ and $R^{19}$, $R^{19}$ and $R^{20}$, $R^{20}$ and $R^{21}$ independently may optionally form a saturated or unsaturated C$_4$-C$_{40}$ ring, which may be interrupted by one or more oxygen and/or sulfur atoms or a group of the formula —N(R$^a$)—, in which R$^a$ represents a hydrogen atom or an optionally substituted hydrocarbon group, where the ring may optionally be substituted; and
in which one or more carbon atoms of the polyacene skeleton may optionally be substituted by one or more heteroatoms selected from N, P, As, O, S, Se and Te; and where one or more of the substituents $R^{12}$ to $R^{23}$ which are arranged at adjacent ring positions of the polyacene may together form a further saturated or unsaturated ring, which may be interrupted by one or more oxygen and/or sulfur atoms or a group of the formula —N(R$^a$)—, in which R$^a$ represents a hydrogen atom or an optionally substituted hydrocarbon group, or an aromatic ring system which is bonded to the polyacene; and
in which n is 0, 1, 2, 3 or 4, preferably 0, 1 or 2, particularly preferably 0 or 2;
where at least one of the radicals $R^{12}$, $R^{13}$, $R^{14}$, $R^{15}$, $R^{16}$, $R^{17}$, $R^{18}$, $R^{19}$, $R^{20}$, $R^{21}$, $R^2$ and/or $R^{23}$ includes at least one group of the formula (L-I) or (L-II).

If n in formula (V-II) is equal to 2, this compound is a pentacene compound. For n=0, the compound may be a "pseudopentacene compound".

According to a further embodiment, the present invention provides formulations comprising functional compounds of the general formulae (V-IIIa) and/or (V-IIIb)

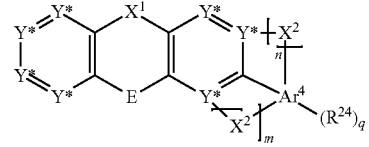

(V-IIIa)

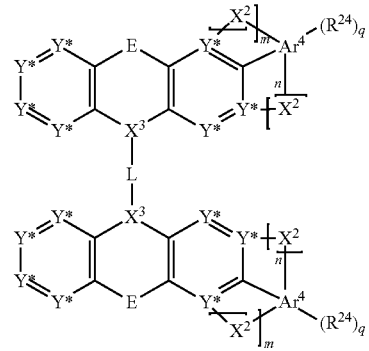

(V-IIIb)

where the following applies to the symbols and indices:
Y* is C if a group $X^2$ is bonded to the group Y or is on each occurrence, identically or differently, CR or N if no group $X^2$ is bonded to the group Y;
E is on each occurrence, identically or differently, a covalent single bond or a divalent bridge selected from N(R$^{25}$), B(R$^{25}$), C(R$^{25}$)$_2$, O, Si(R$^{25}$)$_2$, C=NR$^{25}$, C=C(R$^{25}$)$_2$, S, S=O, SO$_2$, P(R$^{25}$) and P(=O)R$^1$;
$X^1$ is on each occurrence, identically or differently, a divalent bridge selected from N(R$^{25}$), B(R$^{25}$), O, C(R$^{25}$)$_2$, Si(R$^{25}$)$_2$, C=NR$^{25}$, C=C(R$^{25}$)$_2$, S, S=O, SO$_2$, P(R$^{25}$) and P(=O)R$^{25}$;
$X^2$ is on each occurrence, identically or differently, a divalent bridge selected from N(R$^{25}$), B(R$^{25}$), C(R$^{25}$)$_2$, Si(R$^{25}$)$_2$, C=O, C=NR$^{25}$, C=C(R$^{25}$)$_2$, S, S=O, SO$_2$, CR$^{25}$—CR$^{25}$, P(R$^{25}$) and P(=O)R$^{25}$;
$X^3$ is on each occurrence, identically or differently, a divalent bridge selected from N, B, C(R$^1$), Si(R$^1$), P and P(=O);
L is a divalent, aromatic or heteroaromatic ring system having 5 to 40 aromatic ring atoms, which may be substituted by one or more radicals R$^1$;
n, m are 0 or 1, with the proviso that n+m=1 or 2;
q is 1, 2, 3, 4, 5 or 6;
$R^{24}$ is on each occurrence, identically or differently, H, D, F, Cl, Br, I, N(Ar)$_2$, C(=O)Ar, P(=O)Ar$_2$, S(=O)Ar, S(=O)$_2$Ar, CR$^{26}$=CR$^{26}$Ar, CN, NO$_2$, Si(R$^{26}$)$_3$, B(OR)$_2$, OSO$_2$R$^{26}$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals R$^{26}$, where one or more non-adjacent CH$_2$ groups may be replaced by R$^{26}$C=CR$^{26}$, C≡C, Si(R$^{26}$)$_2$, Ge(R$^{26}$)$_2$, Sn(R$^{26}$)$_2$, C=O, C=S, C=Se, C=NR$^{26}$, P(=O)(R$^{26}$), SO, SO$_2$, NR$^{26}$, O, S or CONR$^{26}$ and where one or more H atoms may be replaced by D, F, Cl, Br, I, CN or NO$_2$, a crosslinkable group or an aromatic or heteroaromatic group having 5 to 40 ring atoms, each of which may be substituted by one or more radicals R$^{26}$, or an aromatic or heteroaromatic ring system having 5 to 40 aromatic ring atoms, which may in each case be substituted by one or more radicals R$^{26}$, or an aryloxy or heteroaryloxy group having 5 to 40 aromatic ring atoms, which may be substituted by one or more radicals $R^{26}$, or a combination of these systems; two or more substituents $R^{24}$ here may also form a mono- or polycyclic, aliphatic, aromatic or heteroaromatic ring system with one another, together with the atoms to which they are bonded or, if they are bonded to Ar, with Ar;

$R^{25}$ is on each occurrence, identically or differently, H, D, F, Cl, Br, I, CN, $NO_2$, $CF_3$, $B(OR^{26})_2$, $Si(R^{26})_3$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^{28}$, where one or more non-adjacent $CH_2$ groups may be replaced by $-R^{26}C=CR^{26}-$, $-C\equiv C-$, $Si(R^{26})_2$, $Ge(R^{26})_2$, $Sn(R^{26})_2$, C=O, C=S, C=Se, $C=NR^{26}$, $-O-$, $-S-$, $-COO-$ or $-CONR^{26}-$ and where one or more H atoms may be replaced by D, F, Cl, Br, I, CN or $NO_2$, or arylamines, or substituted or unsubstituted carbazoles, each of which may be substituted by one or more radicals $R^{26}$, or an aryl or heteroaryl group having 5 to 40 ring atoms, which may be substituted by one or more aromatic or heteroaromatic or non-aromatic radicals $R^{27}$, or an aromatic or heteroaromatic ring system having 5 to 40 aromatic ring atoms, which may be substituted by one or more non-aromatic radicals $R^{26}$, or an aryloxy or heteroaryloxy group having 5 to 40 aromatic ring atoms, which may be substituted by one or more non-aromatic radicals $R^{27}$, or a combination of these systems; two or more substituents $R^{25}$ here, together with the atoms to which they are bonded, may also form a mono- or polycyclic, aliphatic, aromatic or heteroaromatic ring system with one another;

$R^{26}$ is on each occurrence, identically or differently, H, D or an aliphatic or aromatic hydrocarbon radical having 1 to 20 C atoms;

$Ar^4$ is on each occurrence, identically or differently, an aromatic or heteroaromatic ring system having 5 to 40 ring atoms, which may be substituted by one or more radicals $R^{25}$;

where at least one of the above-mentioned radicals includes a group of the formulae (L-I) and/or (L-II).

According to a further preferred embodiment of the present invention, preference is given to functional compound of the general formula (V-IVa) and/or formula (V-IVb):

formula (V-IVa)

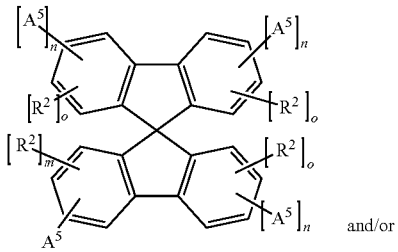

and/or formula (V-IVb)

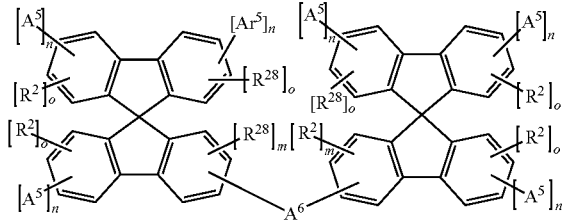

where the following applies to the symbols and indices:
$Ar^5$ is a group of the following formula (V-IVc):

formula (V-IVc)

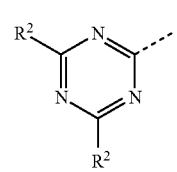

where the dashed bond indicates the bond to the spirobifluorene;
$Ar^6$ is a group of the following formula (V-IVd):

formula (V-IVd)

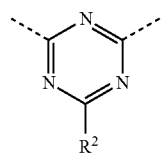

where the dashed bonds indicate the bonds to the spirobifluorene;
$R^{28}$, $R^{29}$ is on each occurrence, identically or differently, H, D, F, Cl, Br, I, CHO, $N(R^{30})_2$, $N(Ar^7)_2$, $B(Ar^7)_2$, $C(=O)Ar^7$, $P(=O)(Ar^7)_2$, $S(=O)Ar^7$, $S(=O)_2Ar^7$, $CR^{30}=CR^{30}Ar^7$, CN, $NO_2$, $Si(R^{30})_3$, $B(OR^{30})_2$, $B(R^{30})_2$, $B(N(R^{30})_2)_2$, $OSO_2R^{30}$, a straight-chain alkyl, alkenyl, alkynyl, alkoxy or thioalkoxy group having 1 or 2 to 40 C atoms respectively or a branched or cyclic alkyl, alkenyl, alkynyl, alkoxy or thioalkoxy group having 3 to 40 C atoms, each of which may be substituted by one or more radicals $R^{30}$, where one or more non-adjacent $CH_2$ groups may be replaced by $R^{30}C=CR^{30}$, $C\equiv C$, $Si(R^{30})_2$, $Ge(R^{30})_2$, $Sn(R^{30})_2$, C=O, C=S, C=Se, $C=NR^{30}$, $P(=O)(R^{30})$, SO, $SO_2$, $NR^{30}$, O, S or $CONR^{30}$ and where one or more H atoms may be replaced by D, F, Cl, Br, I, CN or $NO_2$, a crosslinkable group or an aromatic or heteroaromatic ring system having 5 to 60 aromatic ring atoms, which may in each case be substituted by one or more radicals $R^{30}$, or an aryloxy or heteroaryloxy group having 5 to 60 aromatic ring atoms, which may be substituted by one or more radicals $R^{30}$, or a combination of these systems; two or more adjacent substituents $R^{28}$ here may also form a mono- or polycyclic, aliphatic or aromatic ring system with one another;

$Ar^7$ is on each occurrence, identically or differently, an aromatic or heteroaromatic ring system having 5 to 30 aromatic ring atoms, which may be substituted by one or more radicals $R^{30}$; two radicals $Ar^7$ here which are bonded to the same nitrogen, phosphorus or boron atom may also be linked to one another by a single bond or a bridge selected from $B(R^{30})$, $C(R^{30})_2$, $Si(R^{30})_2$, C=O, C=NR$^{30}$, C=C(R$^{30}$)$_2$, O, S, S=O, SO$_2$, N(R$^{30}$), P(R$^{30}$) and P(=O)R$^{30}$;

$R^{30}$ is on each occurrence, identically or differently, H, D or an aliphatic, aromatic and/or heteroaromatic hydrocarbon radical having 1 to 20 C atoms, in which, in addition, H atoms may be replaced by D or F; two or more adjacent substituents $R^{30}$ here may also form a mono- or polycyclic, aliphatic or aromatic ring system with one another;

n is 0 or 1;

m is 0, 1, 2 or 3;

o is 0, 1, 2, 3 or 4 if n=0 in the same ring and is 0, 1, 2 or 3 if n=1 in the same ring.

In addition, preference is given to soluble functional compounds of the formula (V-V),

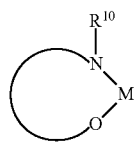

formula (V-V)

where $R^{10}$ has the same meaning as described above for the formulae (V-Ia), (V-Ib), (V-Ic) and (V-Id), the curved line represents two or three atoms and bonds which are necessary to make up a 5- or 6-membered ring with M, where these atoms may also be substituted by one or more radicals $R^{10}$, where at least one of the above-mentioned radicals includes a group of the formulae (L-I) and/or (L-II), and M represents an alkali metal selected from lithium, sodium, potassium, rubidium and caesium.

It is possible here for the complex of the formula (V-V) to be in monomeric form, as depicted above, or for it to be in the form of aggregates, for example comprising two alkali-metal ions and two ligands, four alkali-metal ions and four ligands, six alkali-metal ions and six ligands, or in the form of other aggregates.

Preferred compounds of the formula (V-V) are the compounds of the following formulae (V-V1) and (V-V2)

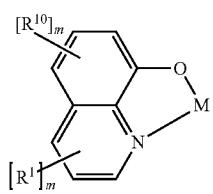

formula (V-V1)

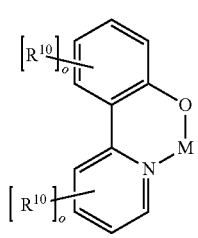

formula (V-V2)

where the symbols used have the same meaning as described above for the formulae (V-Ia), (V-Ib), (V-Ic) and (V-Id) and above for the formula (V-V), and m stands, identically or differently on each occurrence, for 0, 1, 2 or 3 and o stands, identically or differently on each occurrence, for 0, 1, 2, 3 or 4.

Further preferred organic alkali-metal compounds are the compounds of the following formula (V-V3):

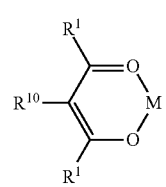

formula (V-V3)

where the symbols used have the same meaning as described above for the formulae (V-Ia), (V-Ib), (V-Ic) and (V-Id) and above for the formula (V-V), where at least one of the above-mentioned radicals includes a group of the formulae (L-I) and/or (L-II).

The alkali metal is preferably selected from lithium, sodium and potassium, particularly preferably from lithium and sodium, and is very particularly preferably lithium.

Particular preference is given to a compound of the formula (V-V1), in particular where M=lithium. Furthermore, the indices m are very particularly preferably =0. The compound is thus very particularly preferably unsubstituted lithium quinolinate.

According to a preferred embodiment of the present invention, preference is given to compounds of the general formula (V-VIa)

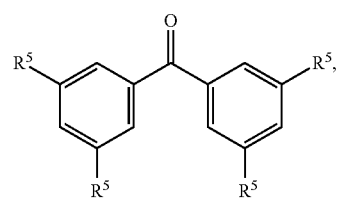

(V-VIa)

particularly preferably of the formula (V-VIb)

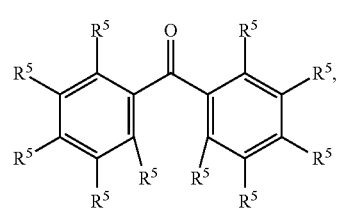

(V-VIb)

where the following applies to the symbols used:

$R^5$ is on each occurrence, identically or differently, hydrogen or an aromatic or heteroaromatic ring system having 5 to 60 aromatic ring atoms, which may be substituted by one or more radicals Re, or an N(Ar)$_2$, Si(Ar)$_3$, C(=O)Ar, OAr, ArSO, ArSO$_2$, P(Ar)$_2$, P(O)(Ar)$_2$ or B(Ar)$_2$ group;

$R^6$ is on each occurrence, identically or differently, H, D, F, Cl, Br, I, CHO, N(Ar)$_2$, C(=O)Ar, P(=O)(Ar)$_2$, S(=O) Ar, S(=O)$_2$Ar, CR$^7$=CR$^7$Ar, CN, NO$_2$, Si(R$^8$)$_3$, B(OR$^8$)$_2$, B(R$^8$)$_2$, B(N(R$^8$)$_2$)$_2$, OSO$_2$R$^8$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^8$, where one or more non-adjacent $CH_2$ groups may be replaced by $R^8C=CR^8$, $C\equiv C$, $SI(R^8)_2$, $Ge(R^8)_2$, $Sn(R^8)_2$, $C=O$, $C=S$, $C=Se$, $C=NR^8$, $P(=O)(R^8)$, SO, $SO_2$, $NR^8$, O, S or $CONR^8$ and where one or more H atoms may be replaced by F, Cl, Br, I, CN or $NO_2$, or an aromatic or heteroaromatic ring system having 5 to 60 aromatic ring atoms, which may in each case be substituted by one or more radicals $R^8$, or an aryloxy or heteroaryloxy group having 5 to 60 aromatic ring atoms, which may be substituted by one or more radicals $R^8$, or a combination of these systems;

$R^7$ is on each occurrence, identically or differently, H, D, F or a linear alkyl group having 1 to 20 C atoms or a branched or cyclic alkyl group having 3 to 20 C atoms; a plurality of radicals $R^7$ here may form a ring system with one another;

$R^8$ is on each occurrence, identically or differently, H, D or an aliphatic, aromatic and/or heteroaromatic hydrocarbon radical having 1 to 20 C atoms, in which, in addition, H atoms may be replaced by F; and Ar is on each occurrence, identically or differently, an aromatic or heteroaromatic ring system having 5 to 30 aromatic ring atoms, which may be substituted by one or more non-aromatic radicals $R^6$; two radicals Ar here which are bonded to the same nitrogen, phosphorus or boron atom may also be linked to one another by a single bond or a bridge selected from $B(R^8)$, $C(R^8)_2$, $Si(R^8)_2$, $C=O$, $C=NR^8$, $C=C(R^8)_2$, O, S, $S=O$, $SO_2$, $N(R^8)$, $P(R^8)$ and $P(=O)R^8$.

According to a particularly preferred embodiment, it is possible to employ compounds of the formula (V-VIc):

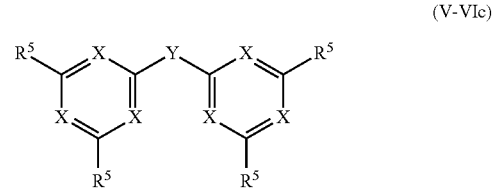

(V-VIc)

where the following applies to the symbols used:

Y is $C=O$ or $C(R^7)_2$;

X is on each occurrence, identically or differently, $CR^9$ or N;

$R^5$ has the meaning given above in relation to formula (V-VIa);

$R^7$ has the meaning given above in relation to formula (V-VIa);

$R^9$ is on each occurrence, identically or differently, H, D, F, CN, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^7$, where one or more non-adjacent $CH_2$ groups may be replaced by $R^7C=CR^7$, $C\equiv C$, O or S and where one or more H atoms may be replaced by F.

The functional compounds of the formula (I) which are particularly preferably to be employed include, inter alia,

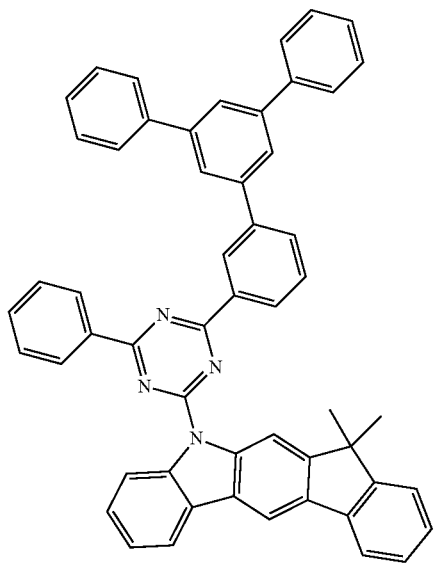

-continued
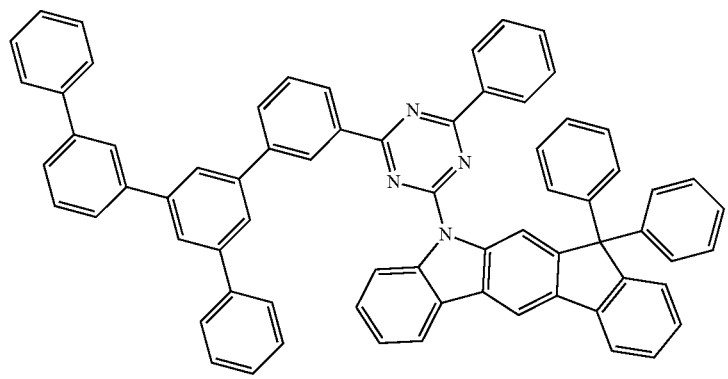
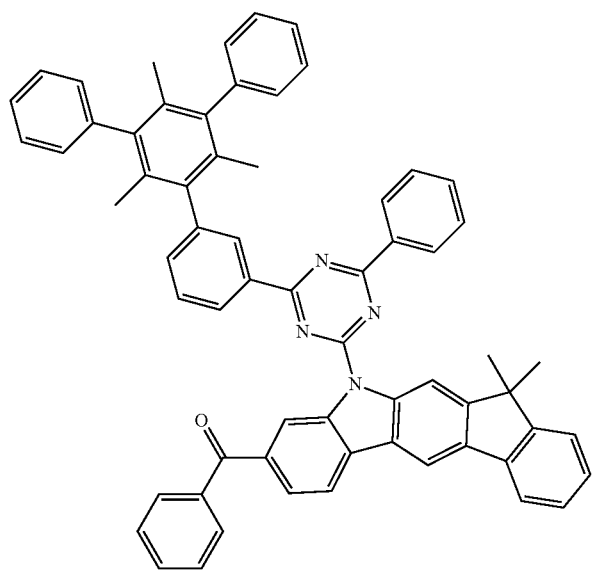
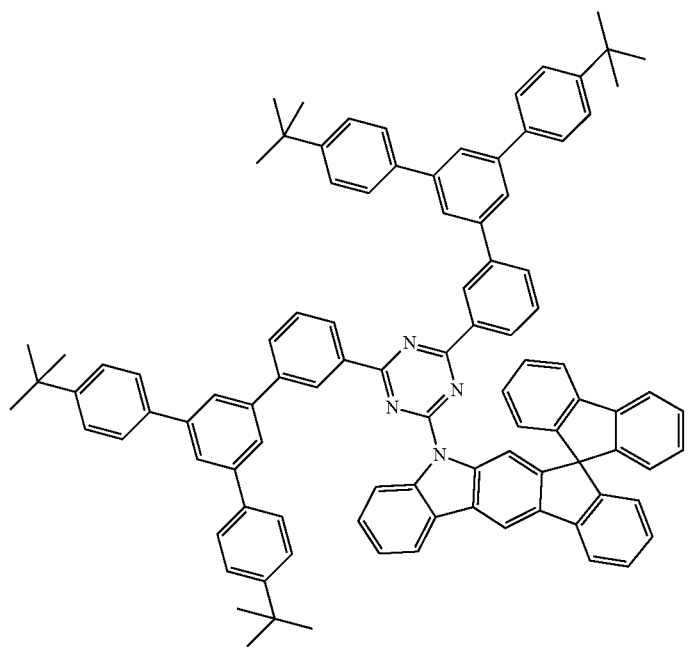

-continued
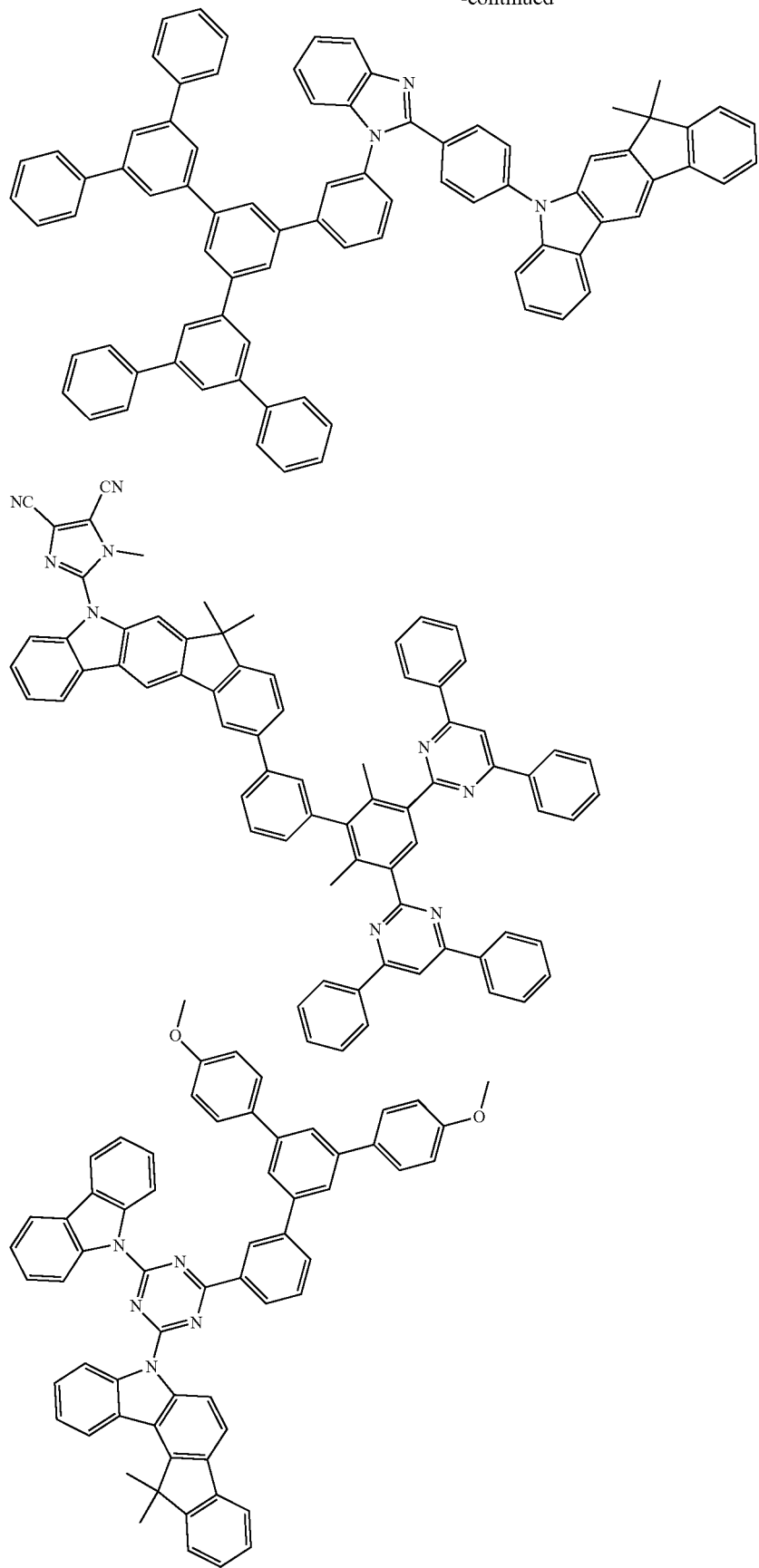

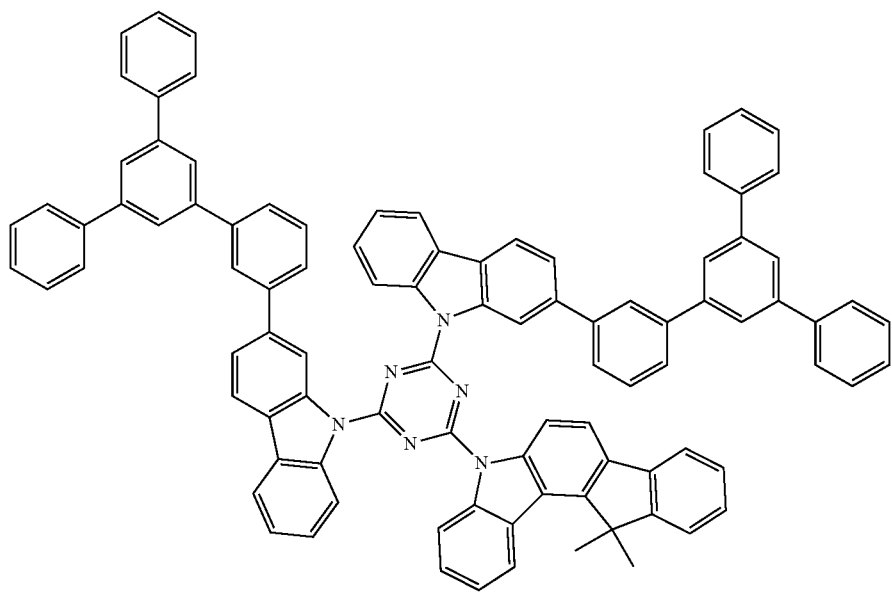
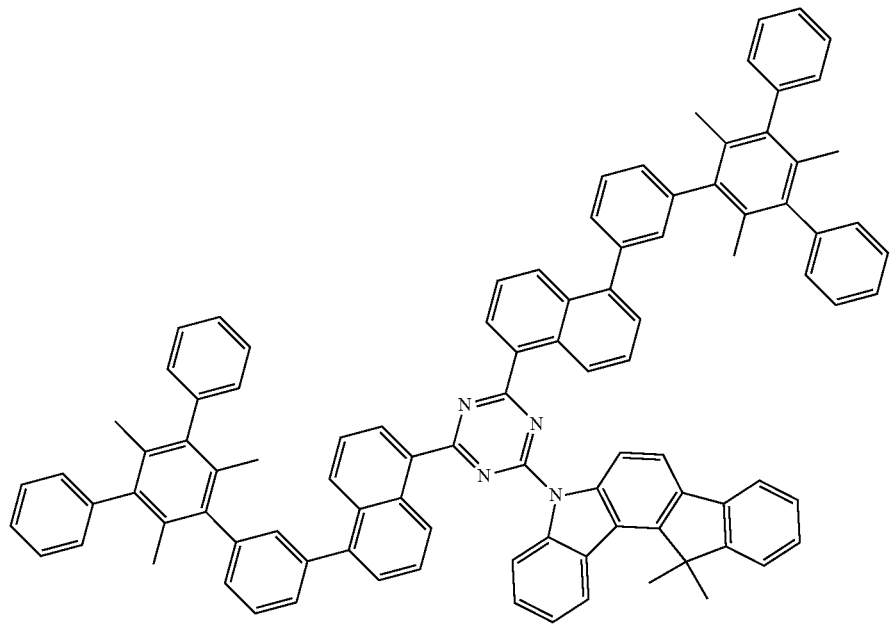
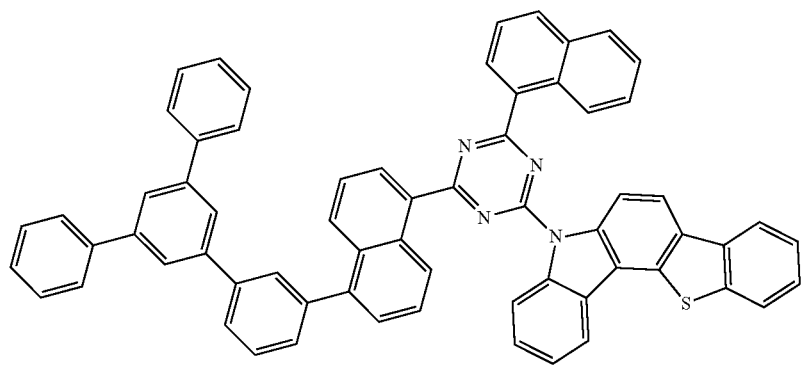

-continued
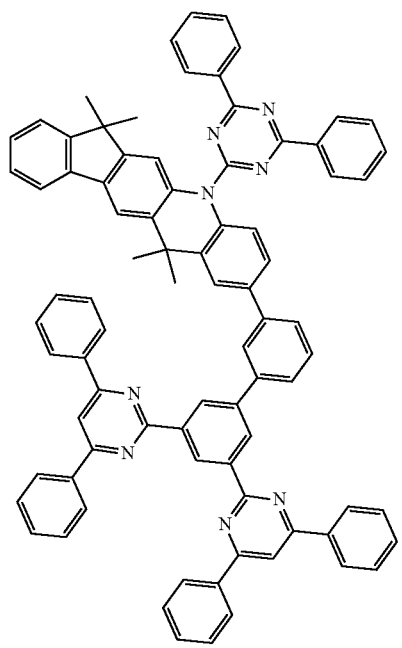
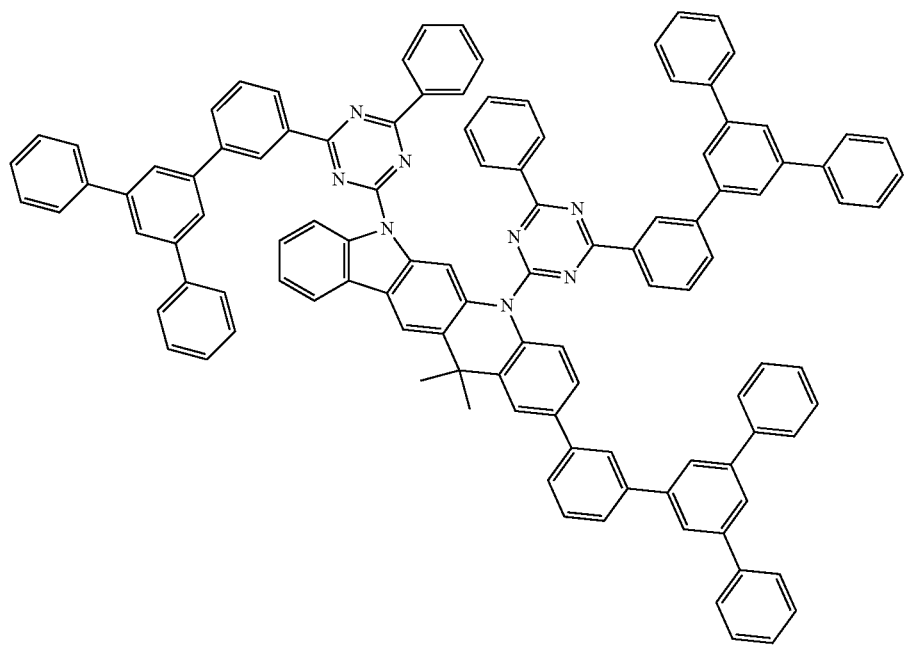

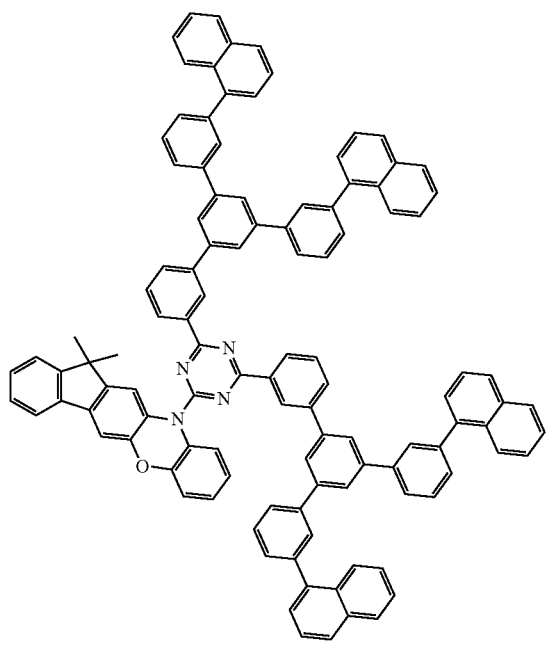
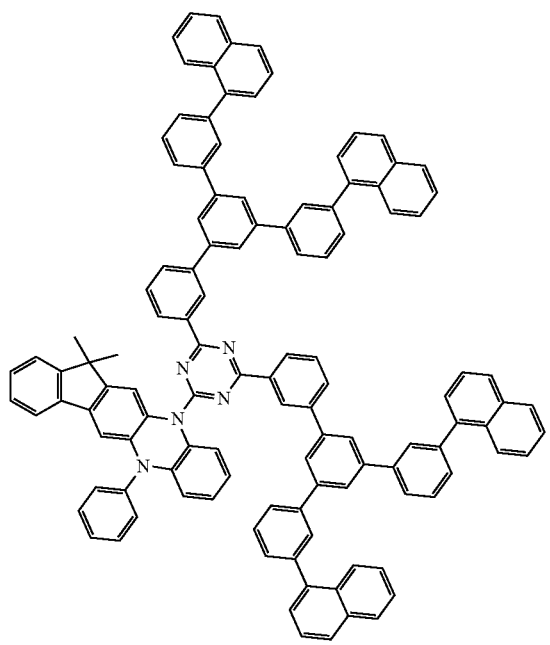

-continued
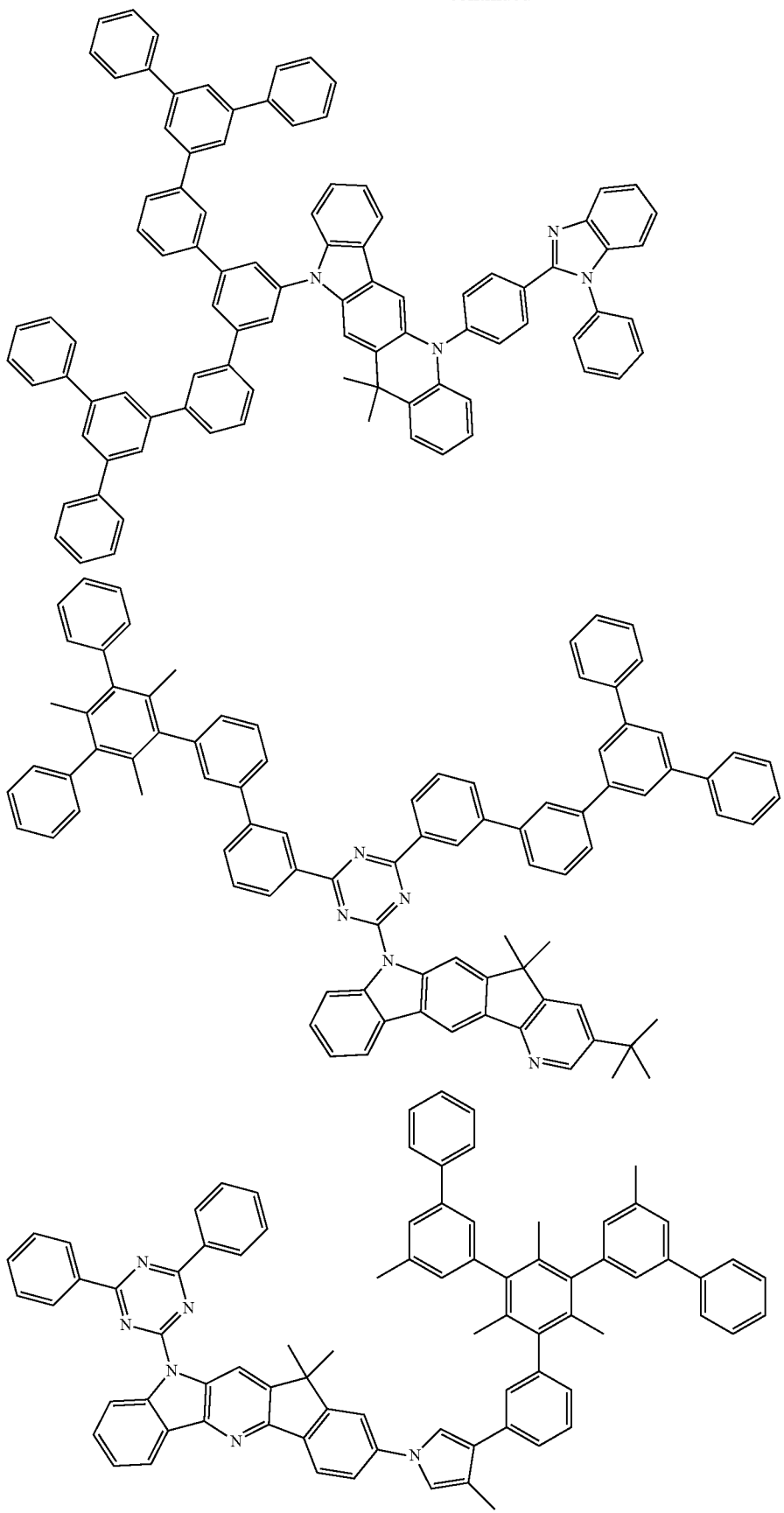

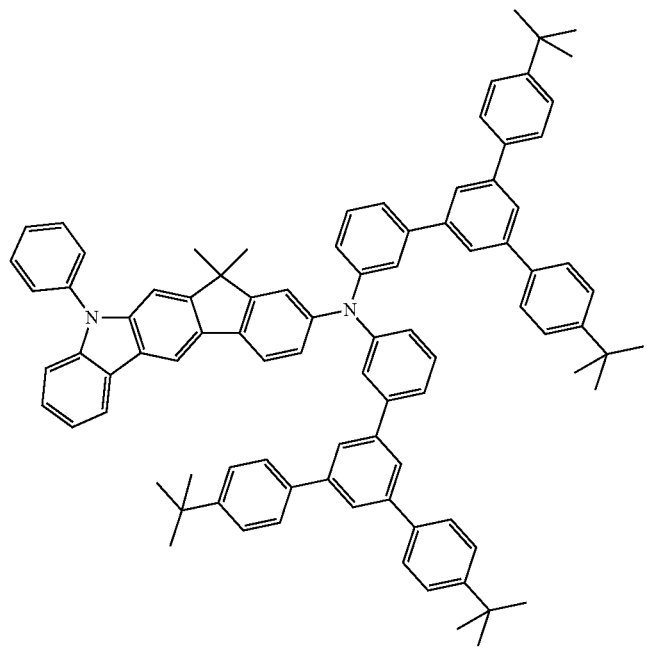
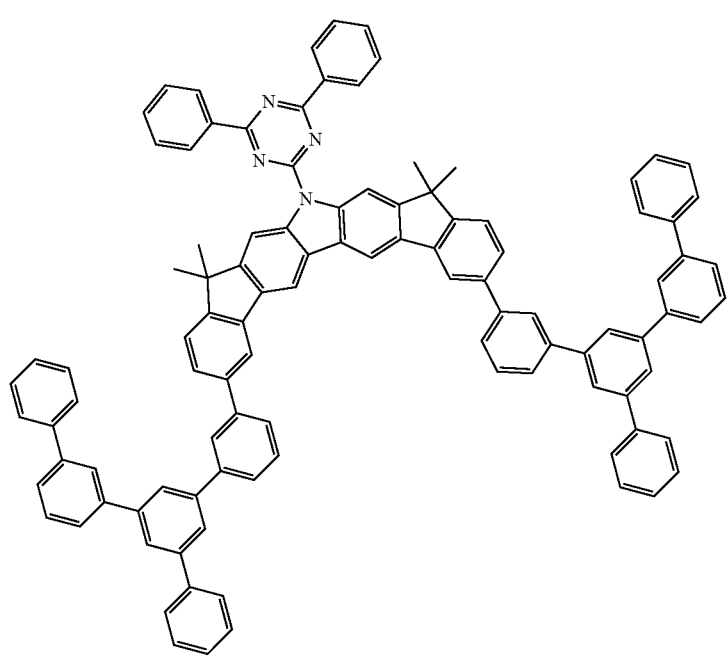

-continued
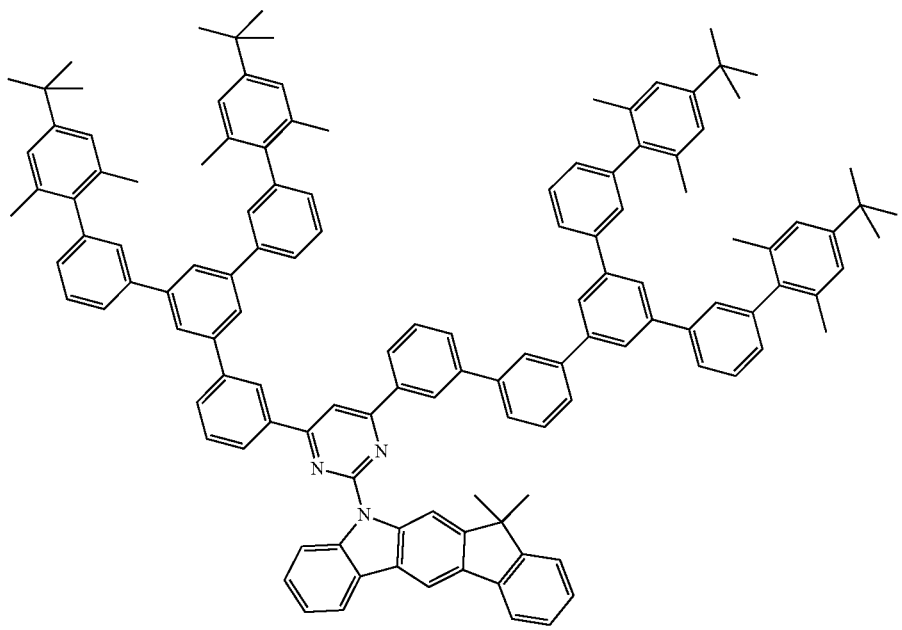
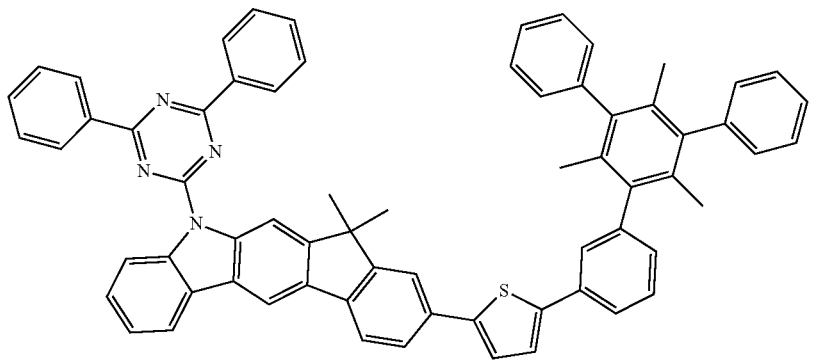
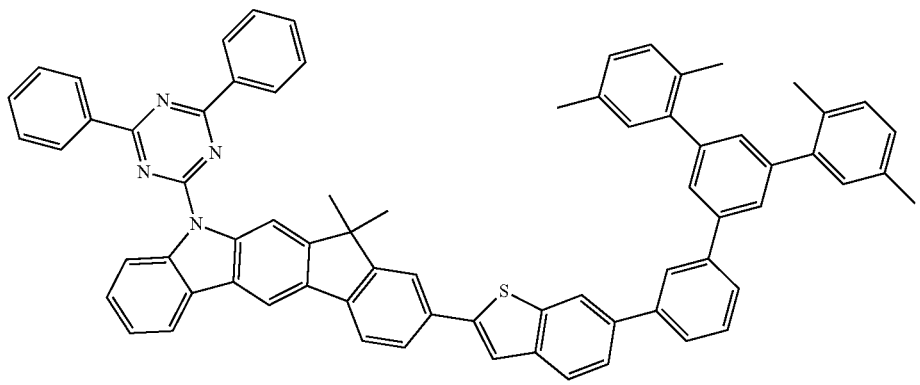

-continued
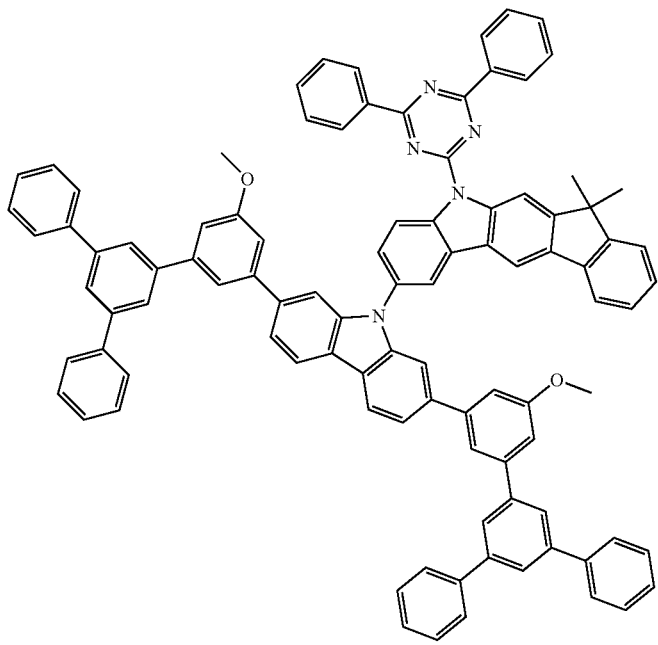
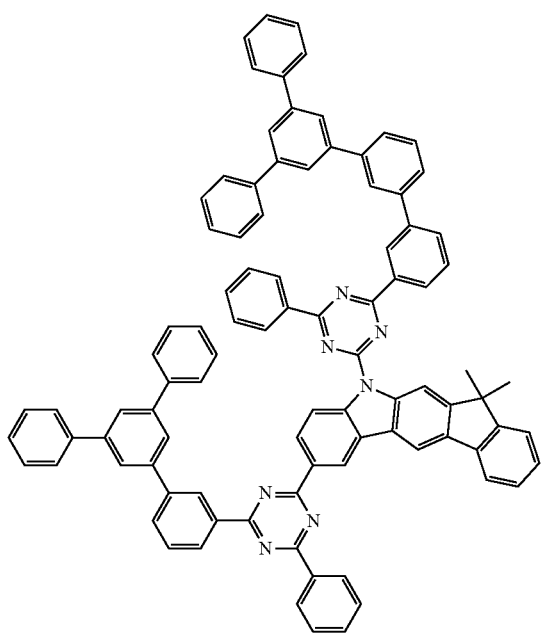

-continued
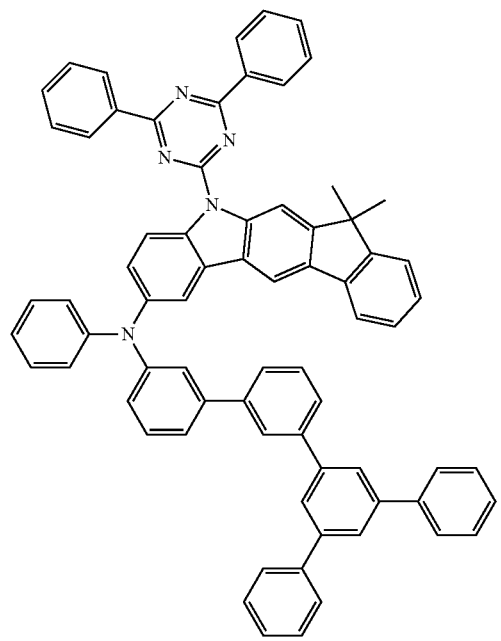
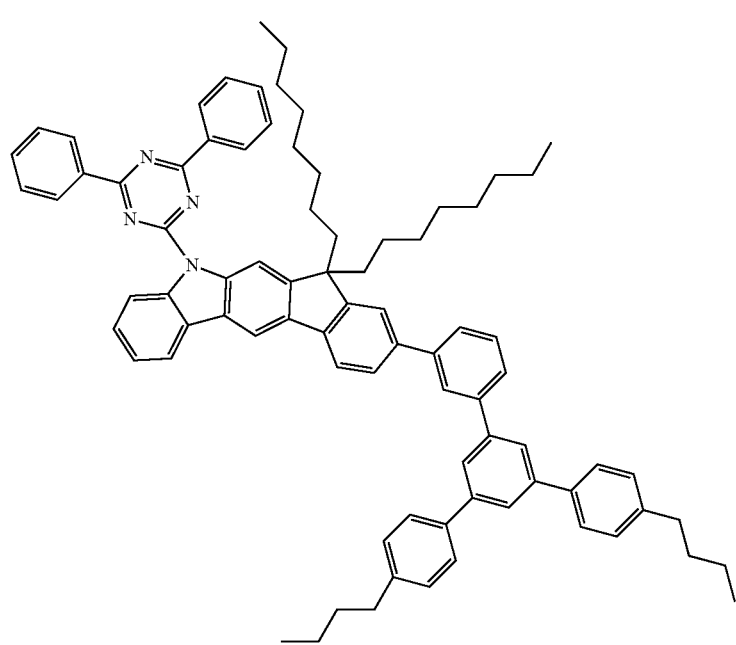

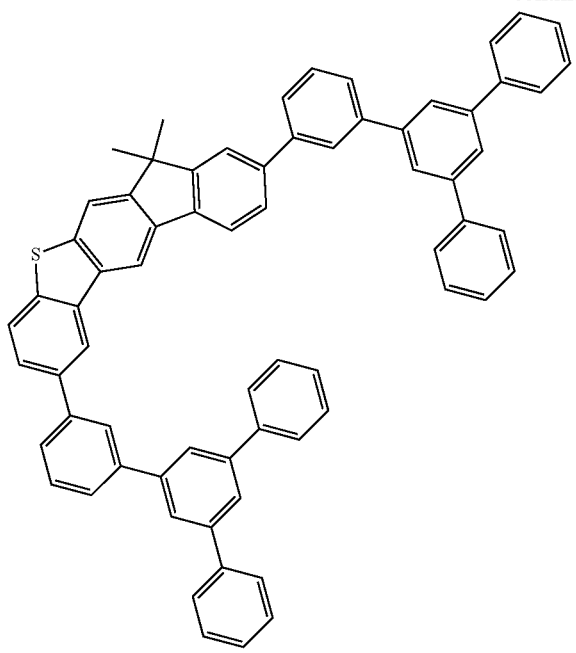
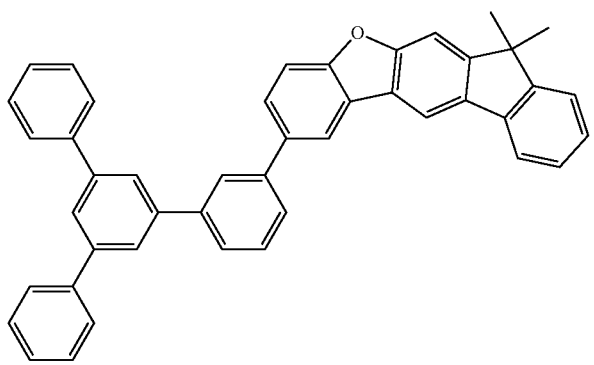
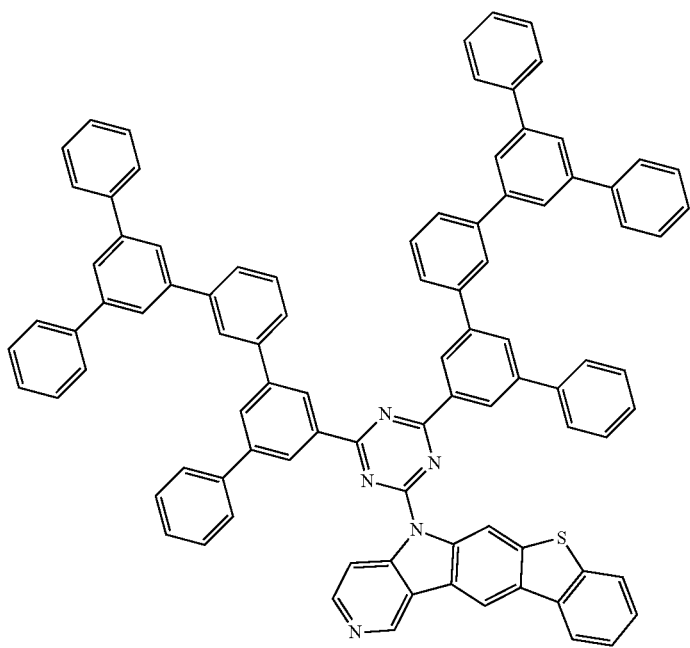

-continued
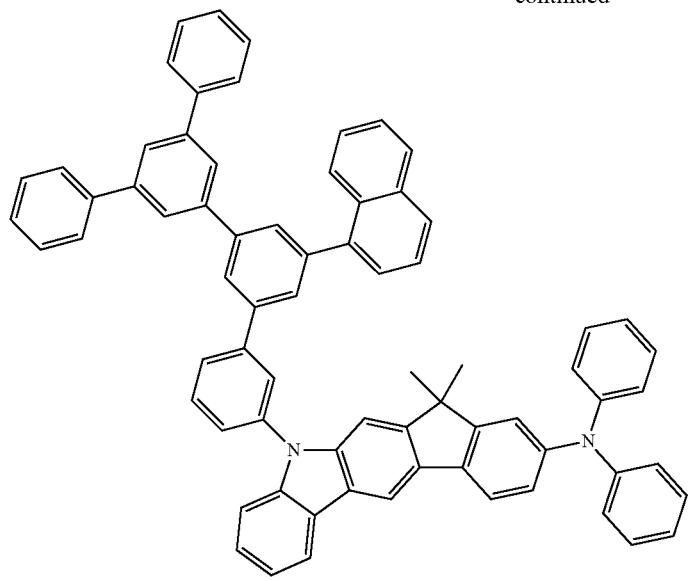
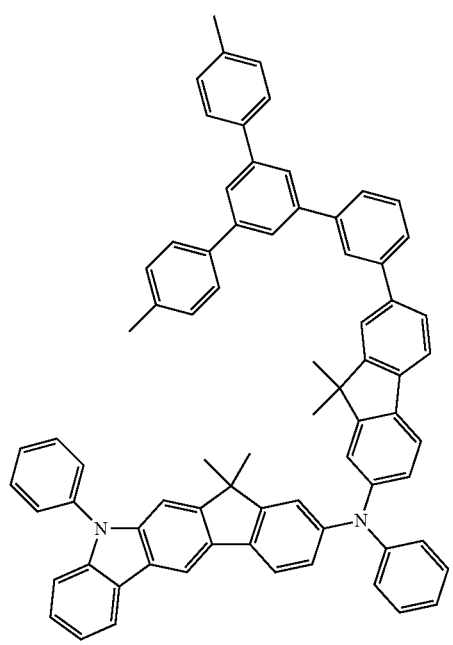
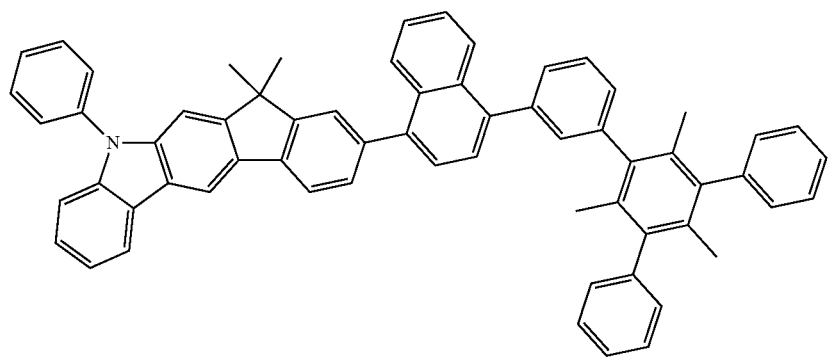

-continued
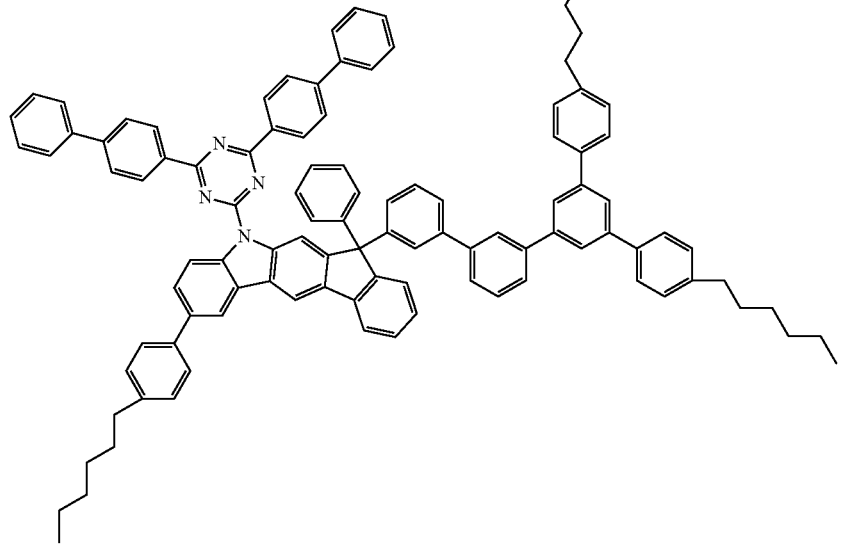
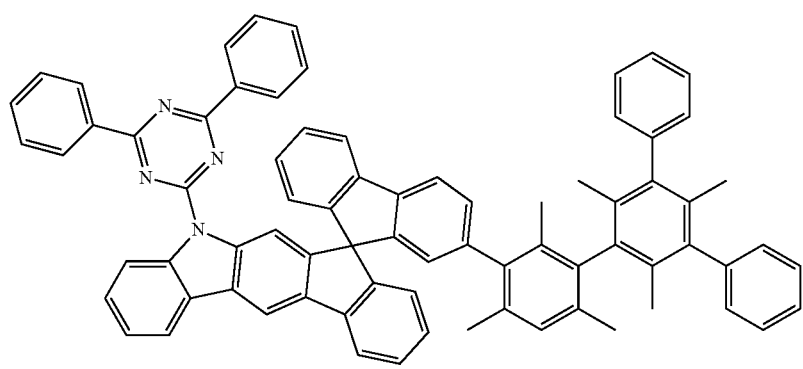
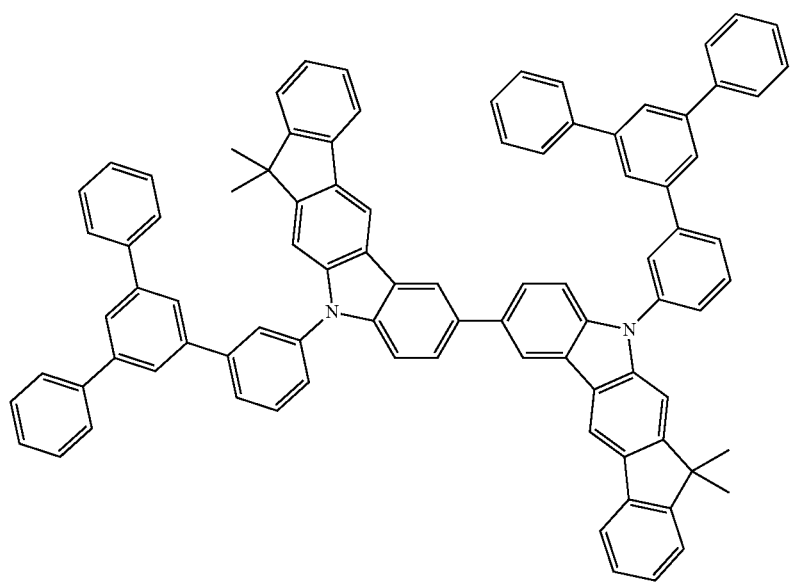

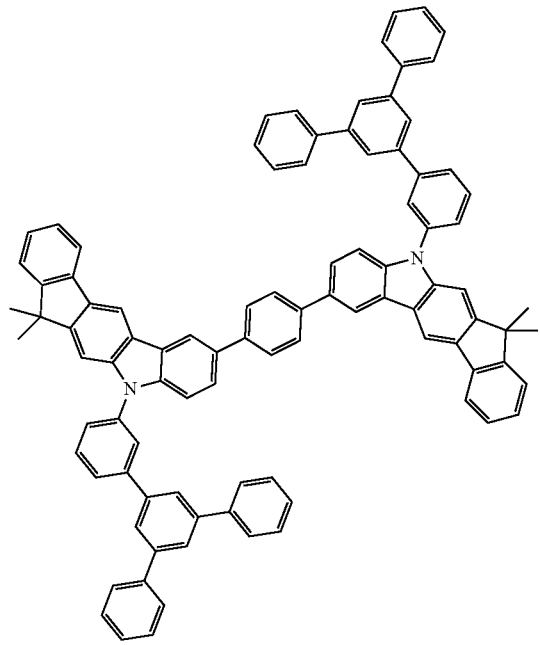
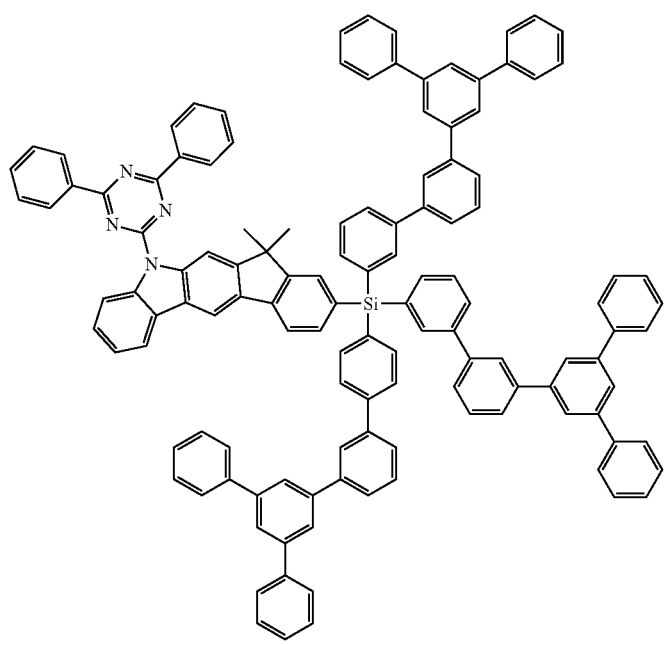

-continued
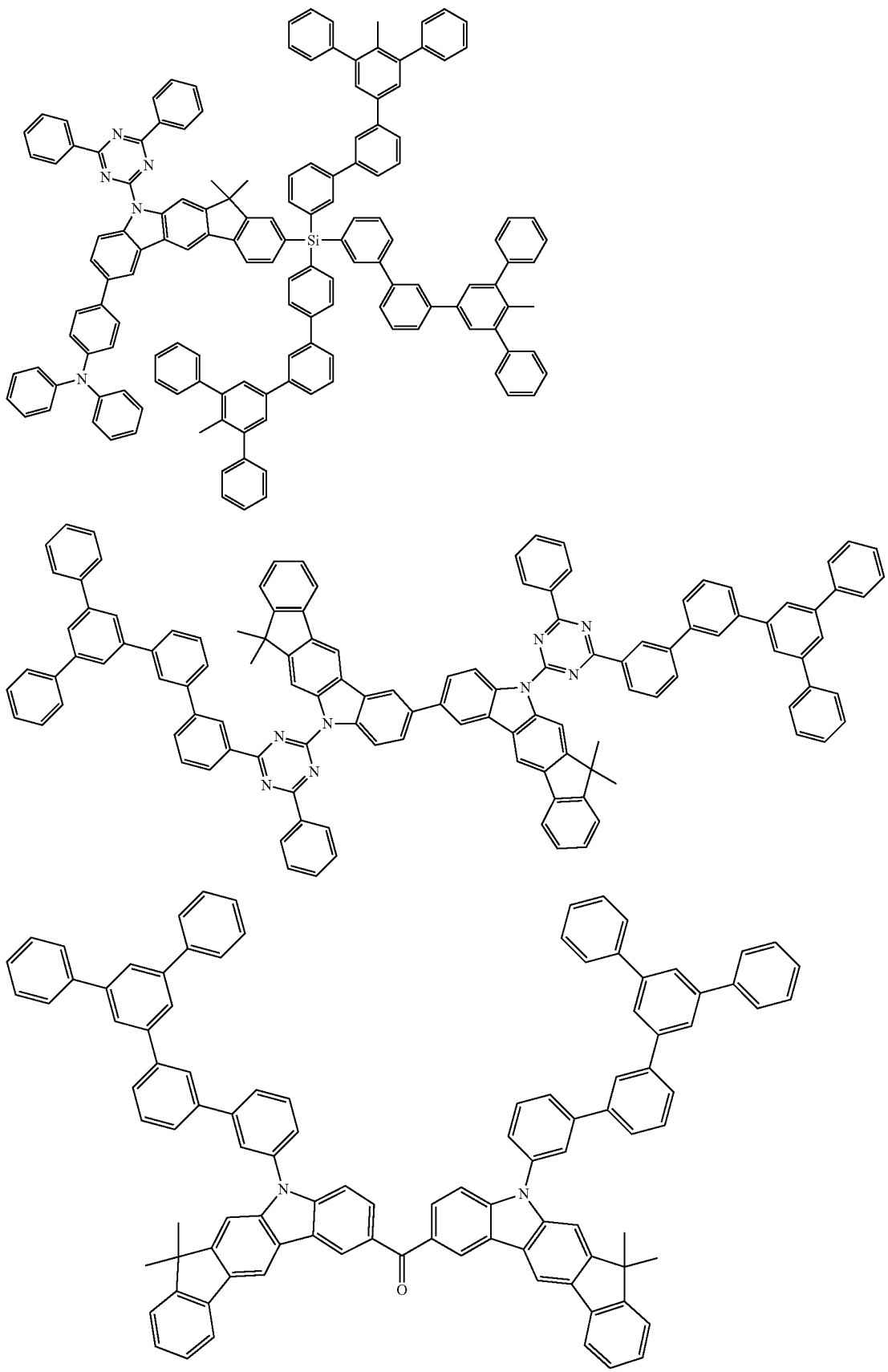

-continued
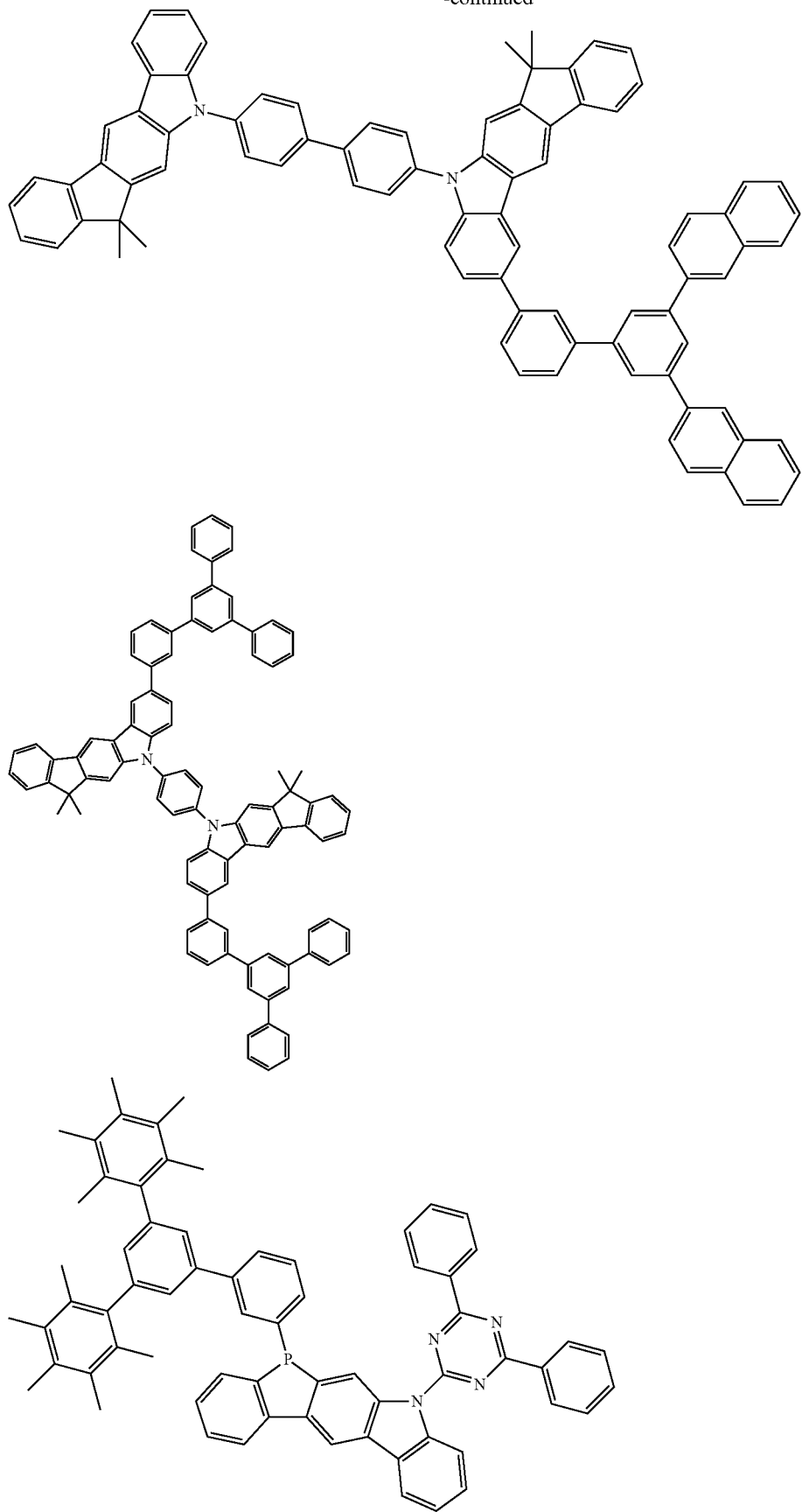

-continued
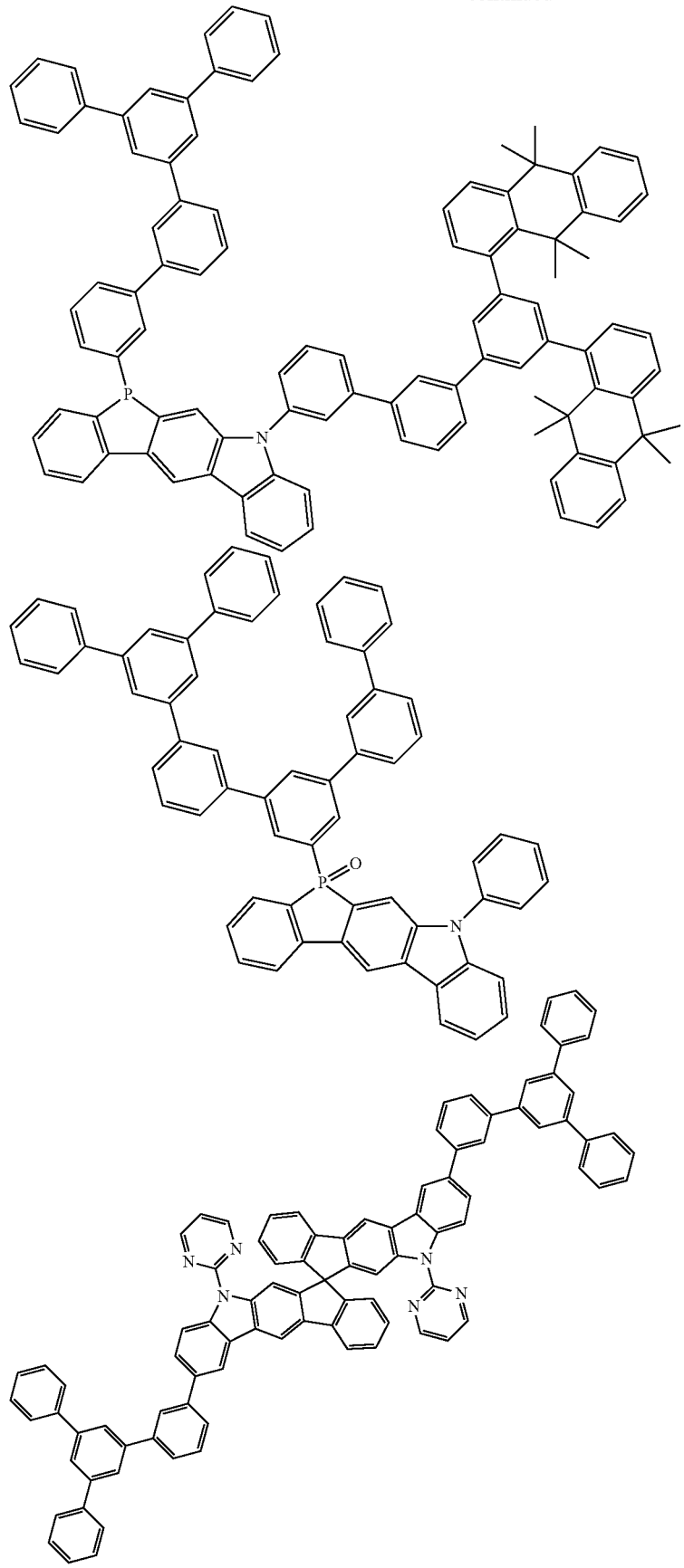

-continued
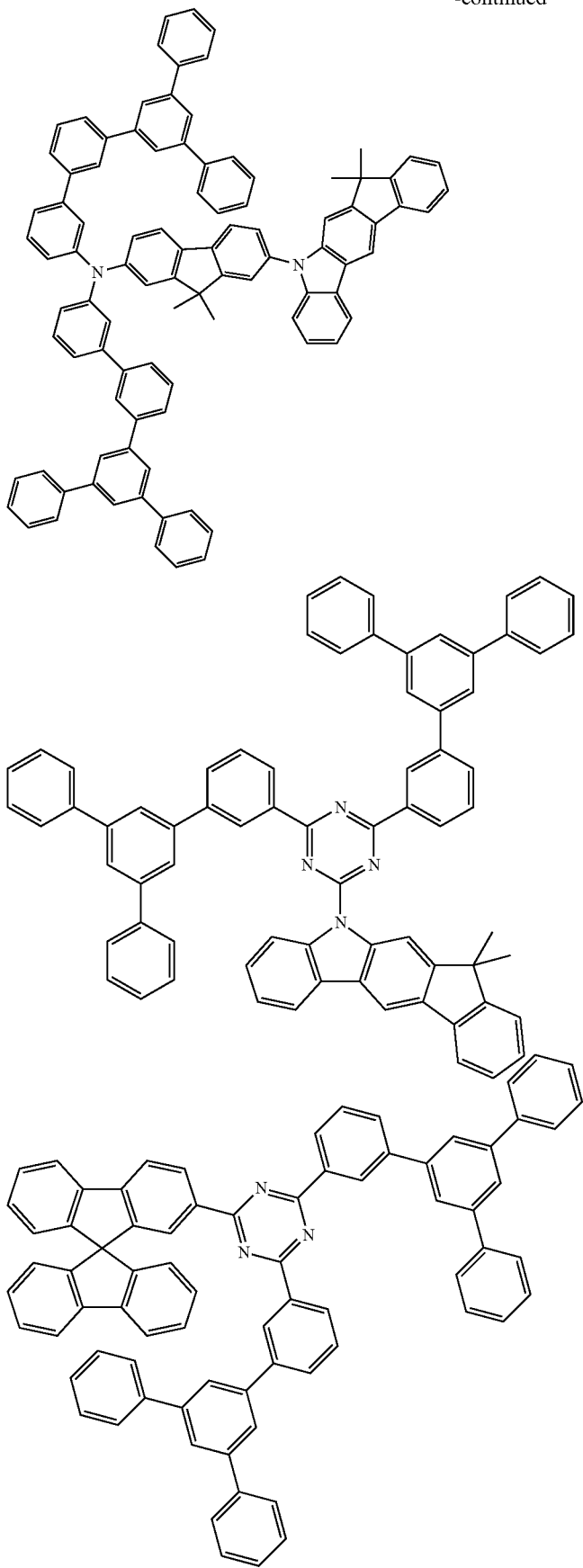

-continued
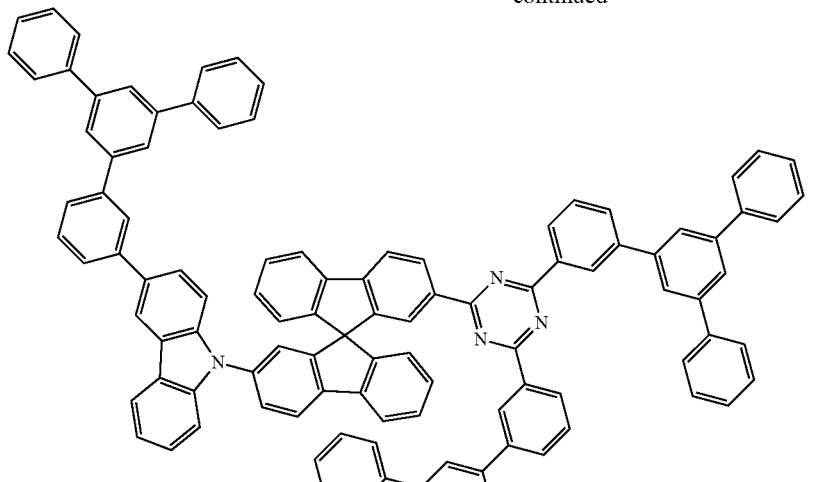
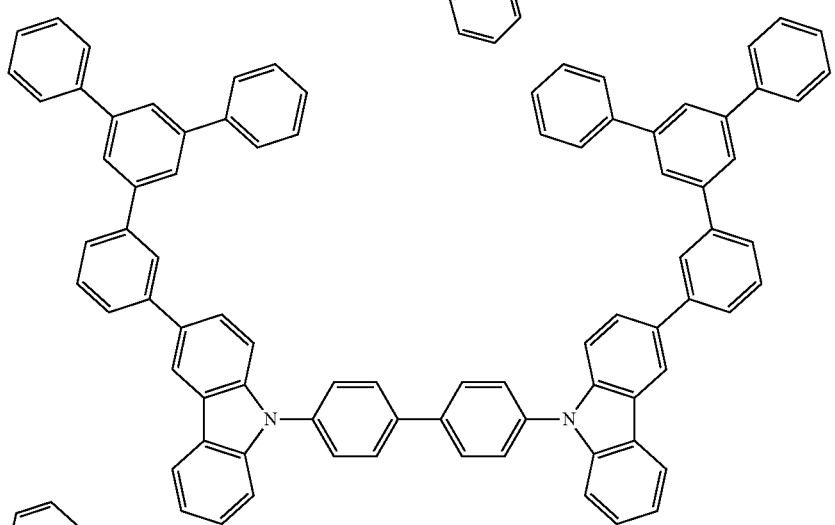
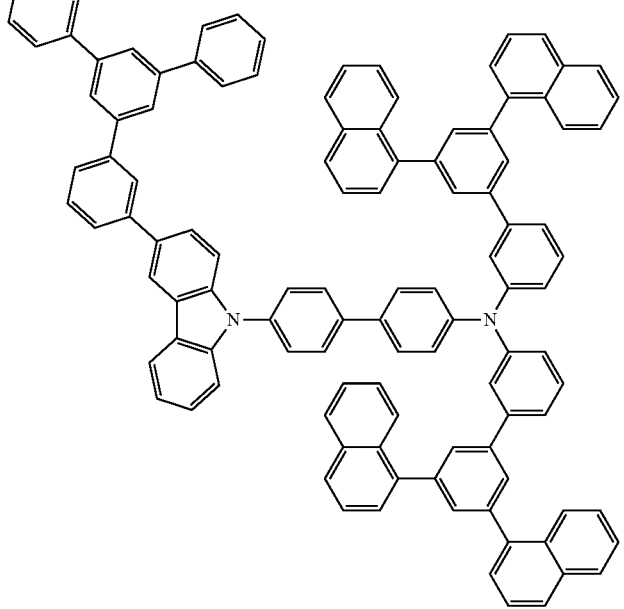

-continued
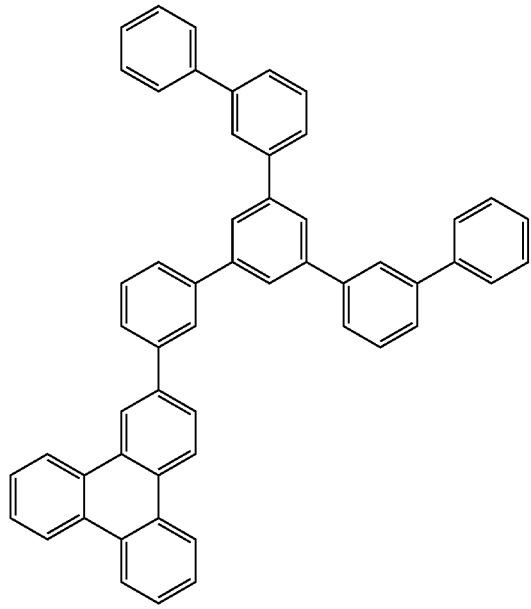
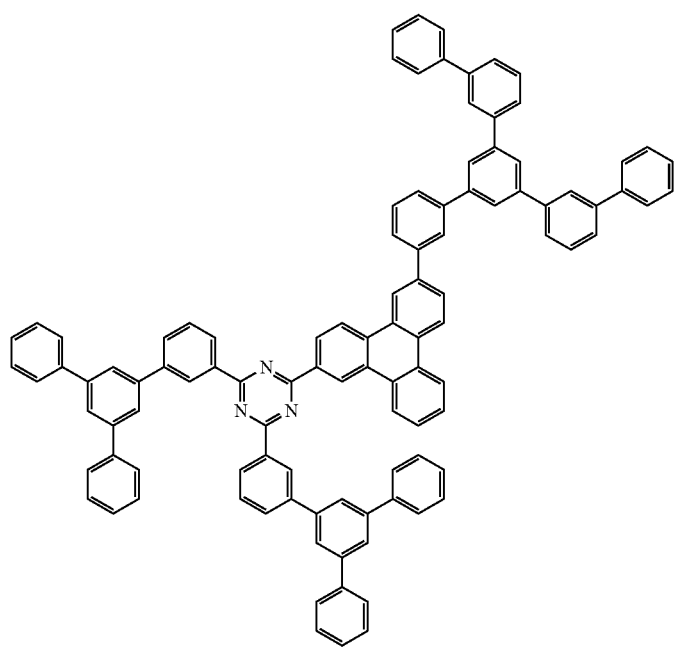

-continued
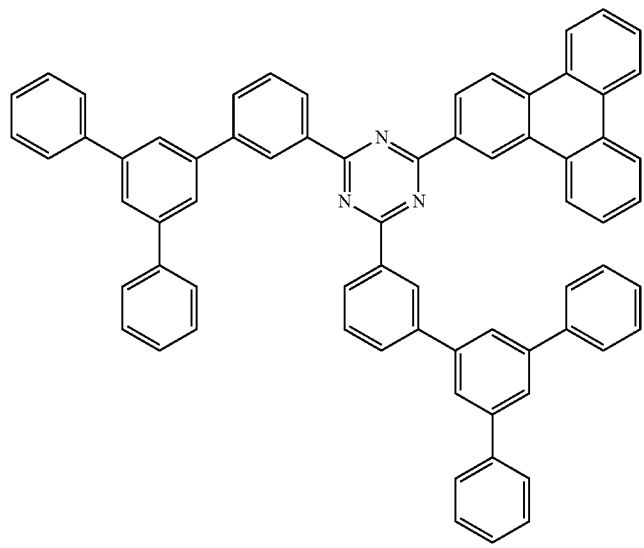
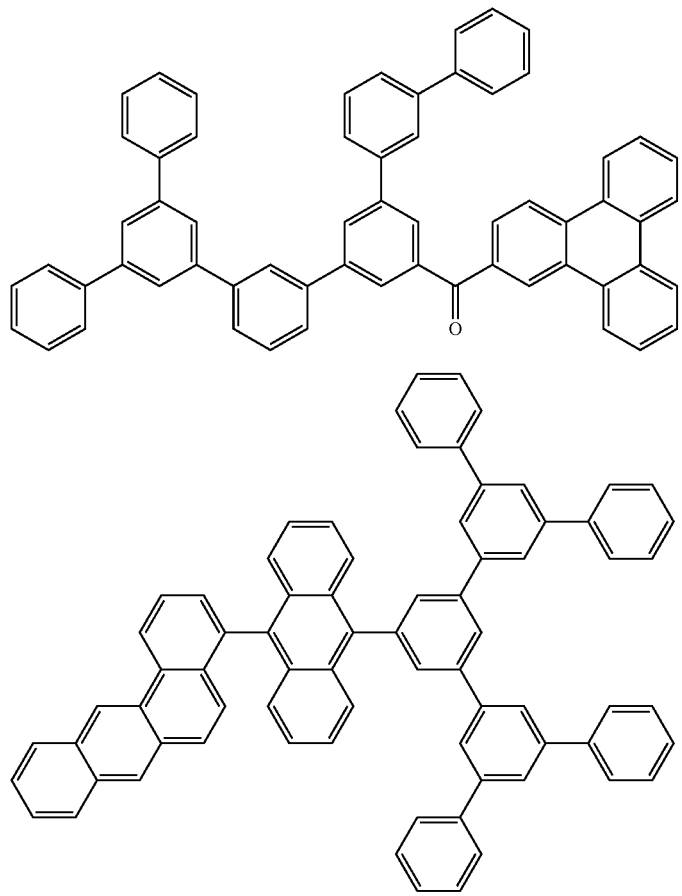

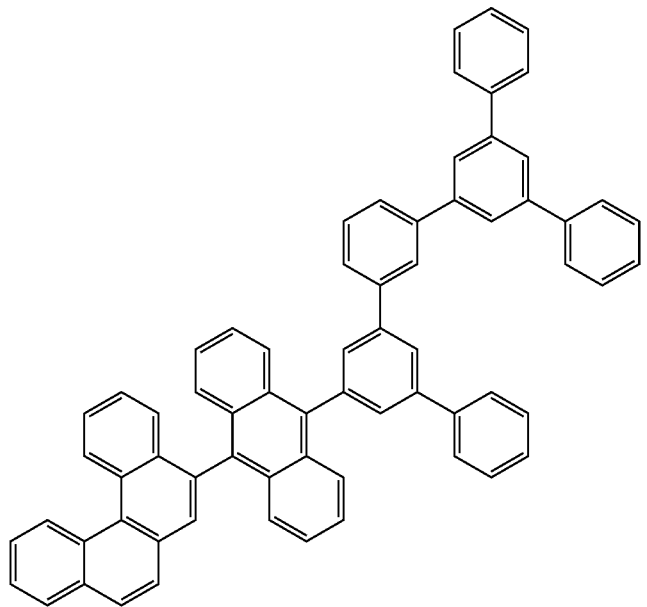
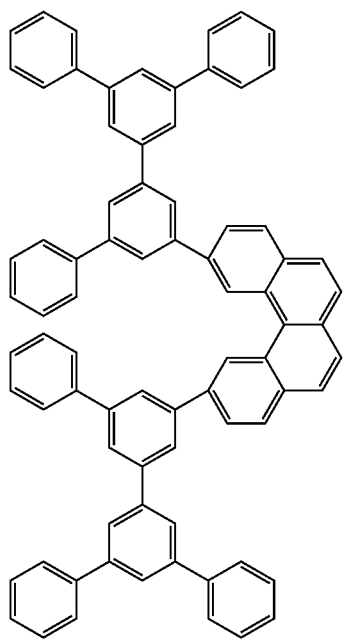
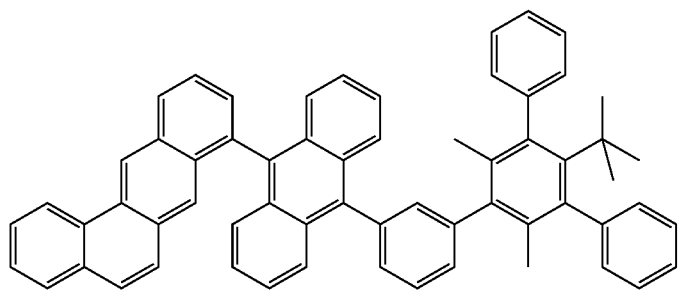

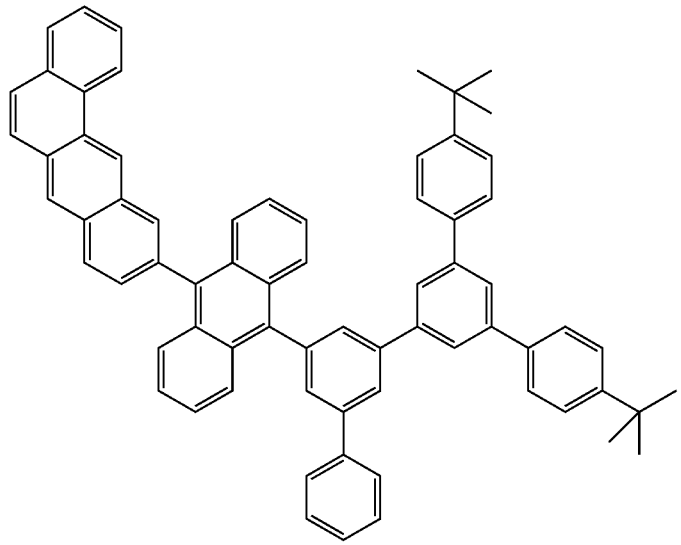
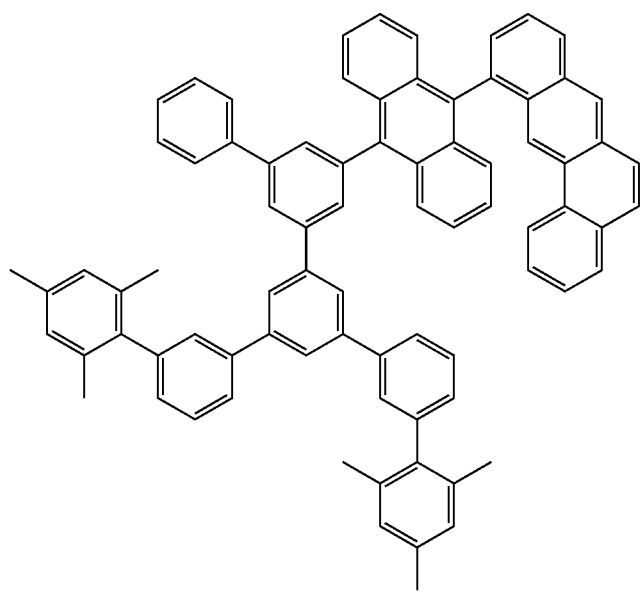

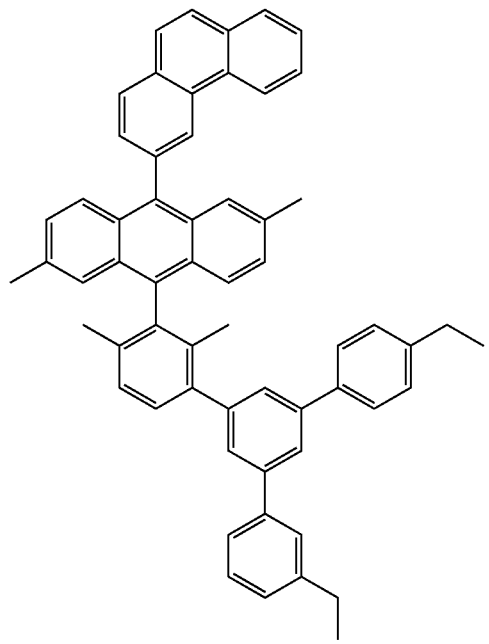
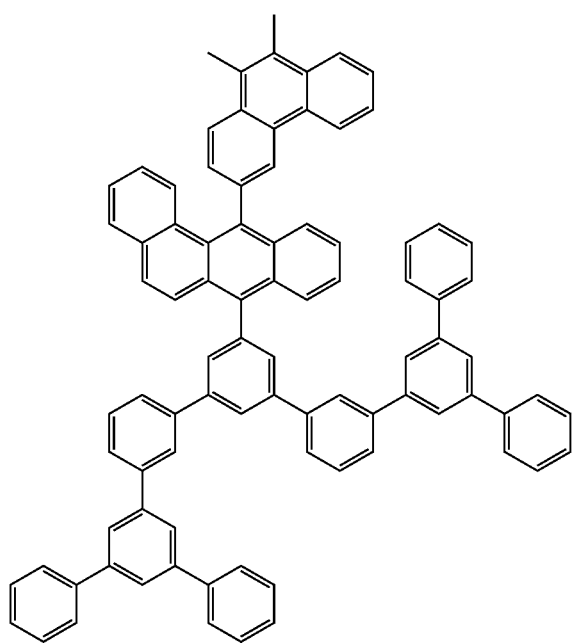

-continued
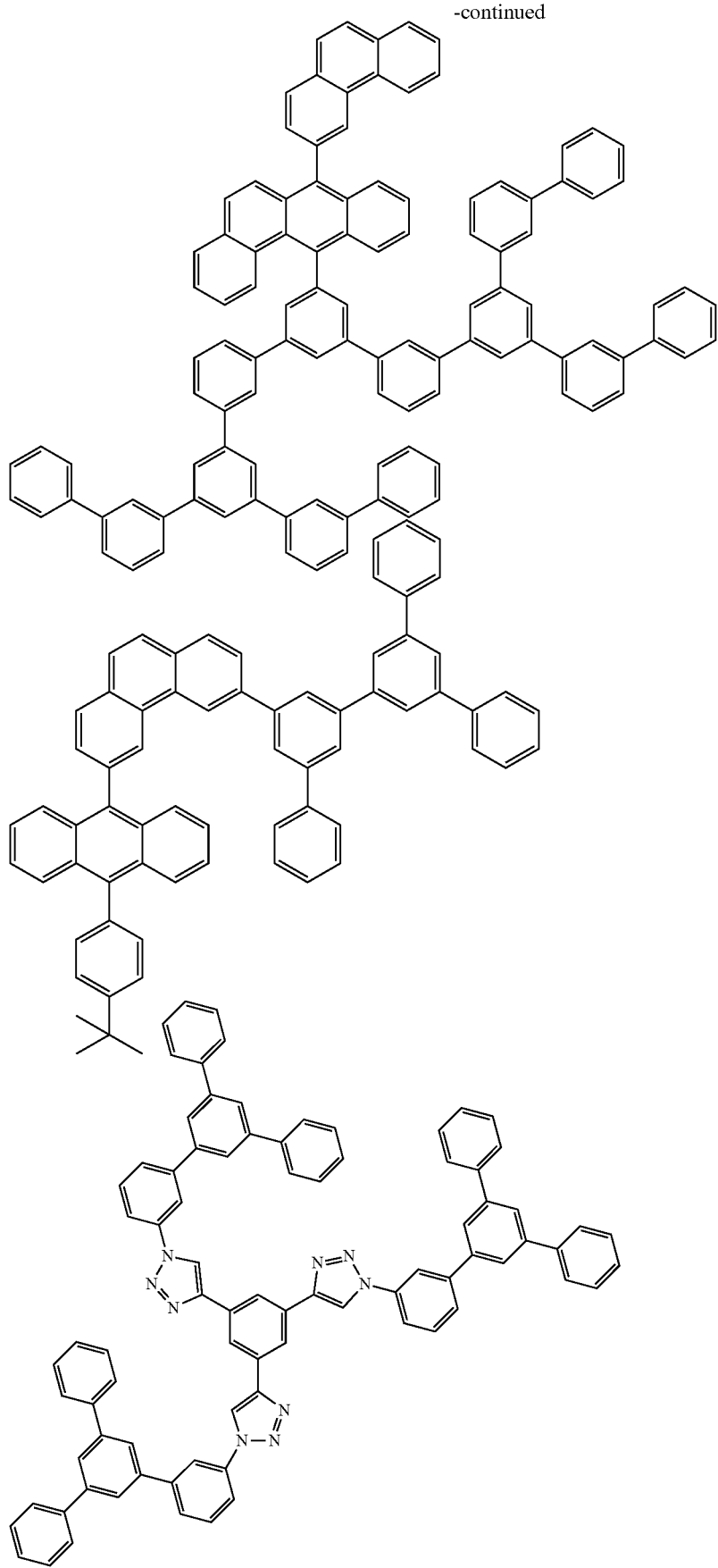

-continued
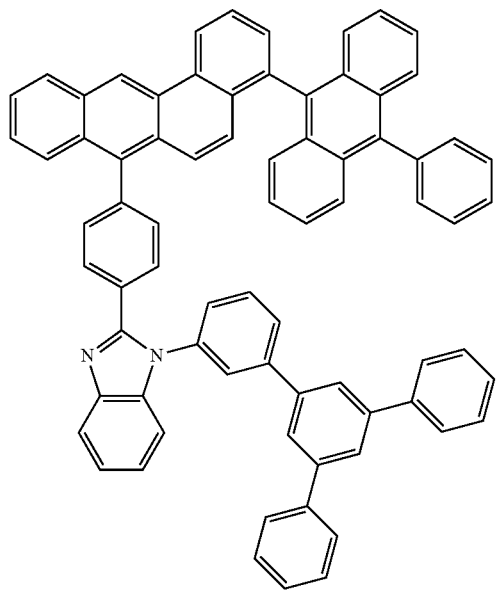
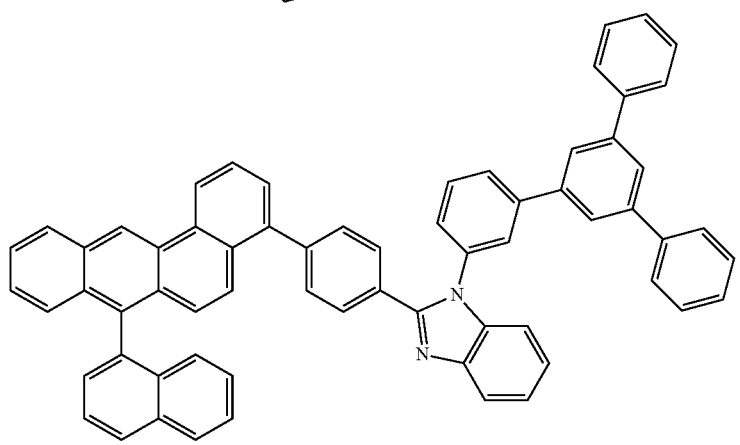
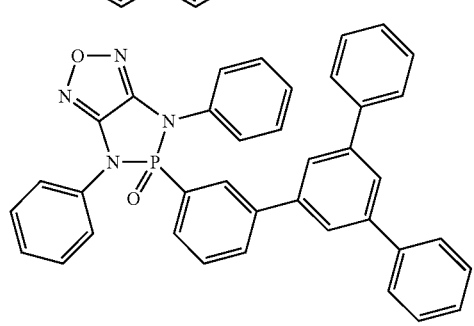
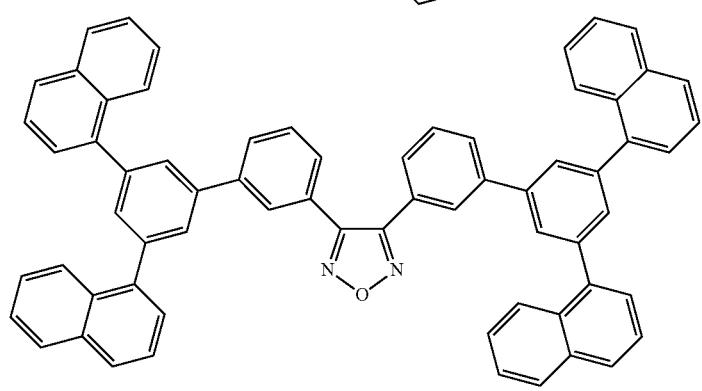

-continued
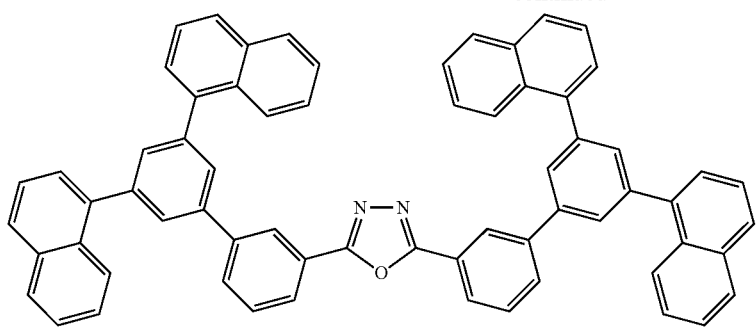
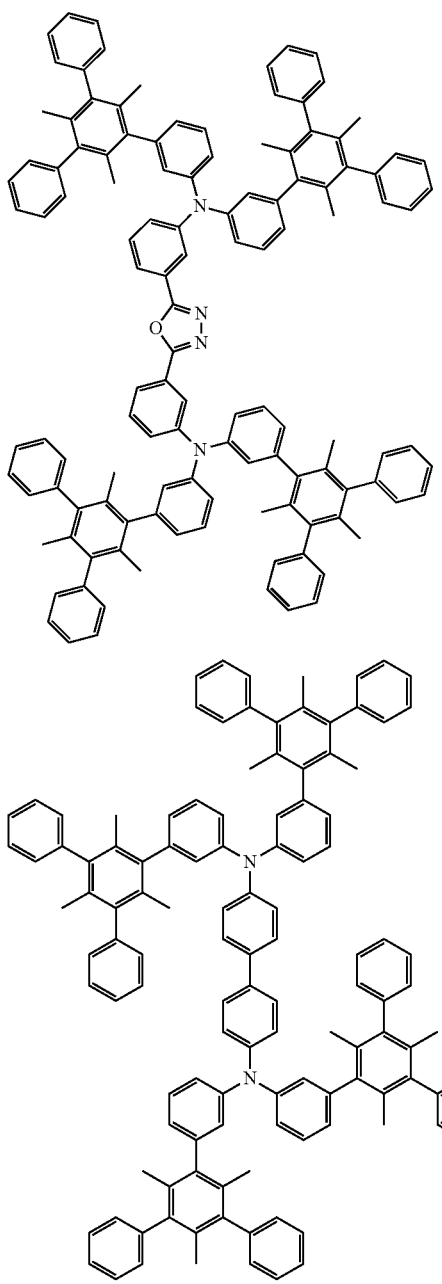

105
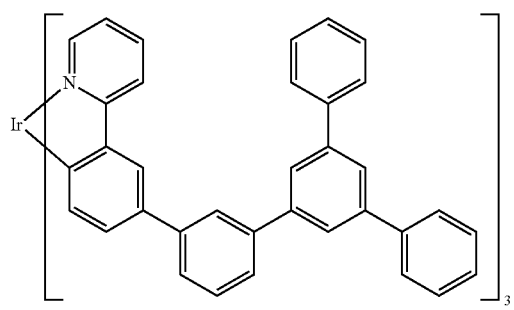
106
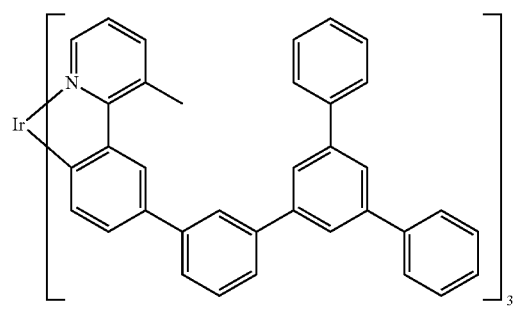
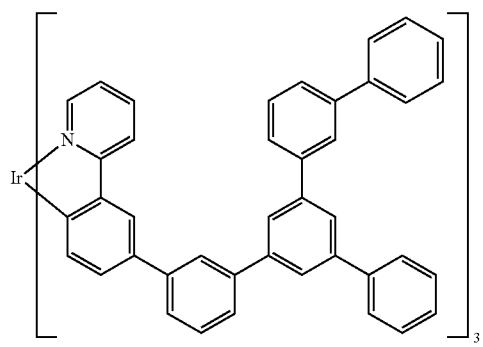
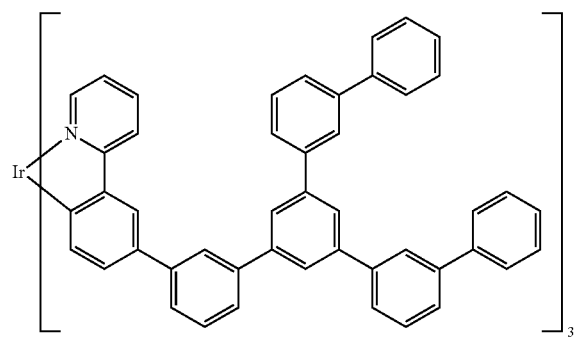
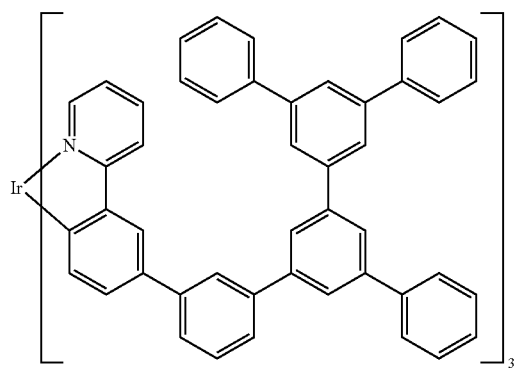
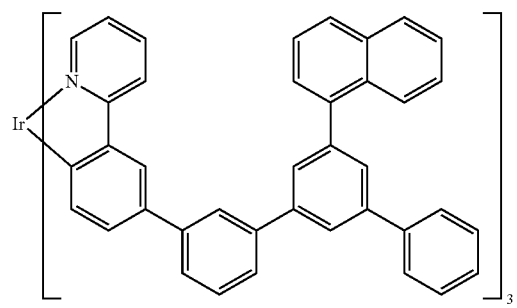
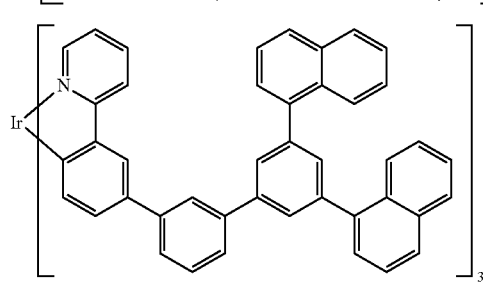
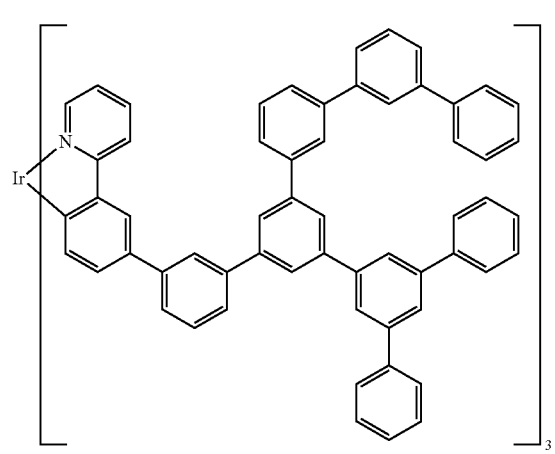

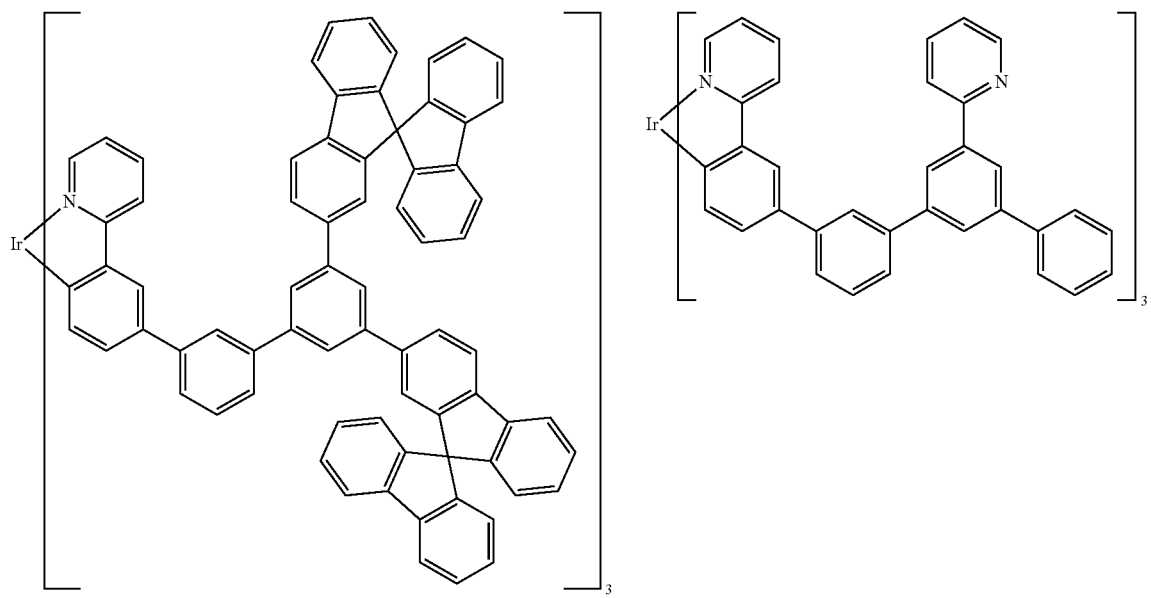
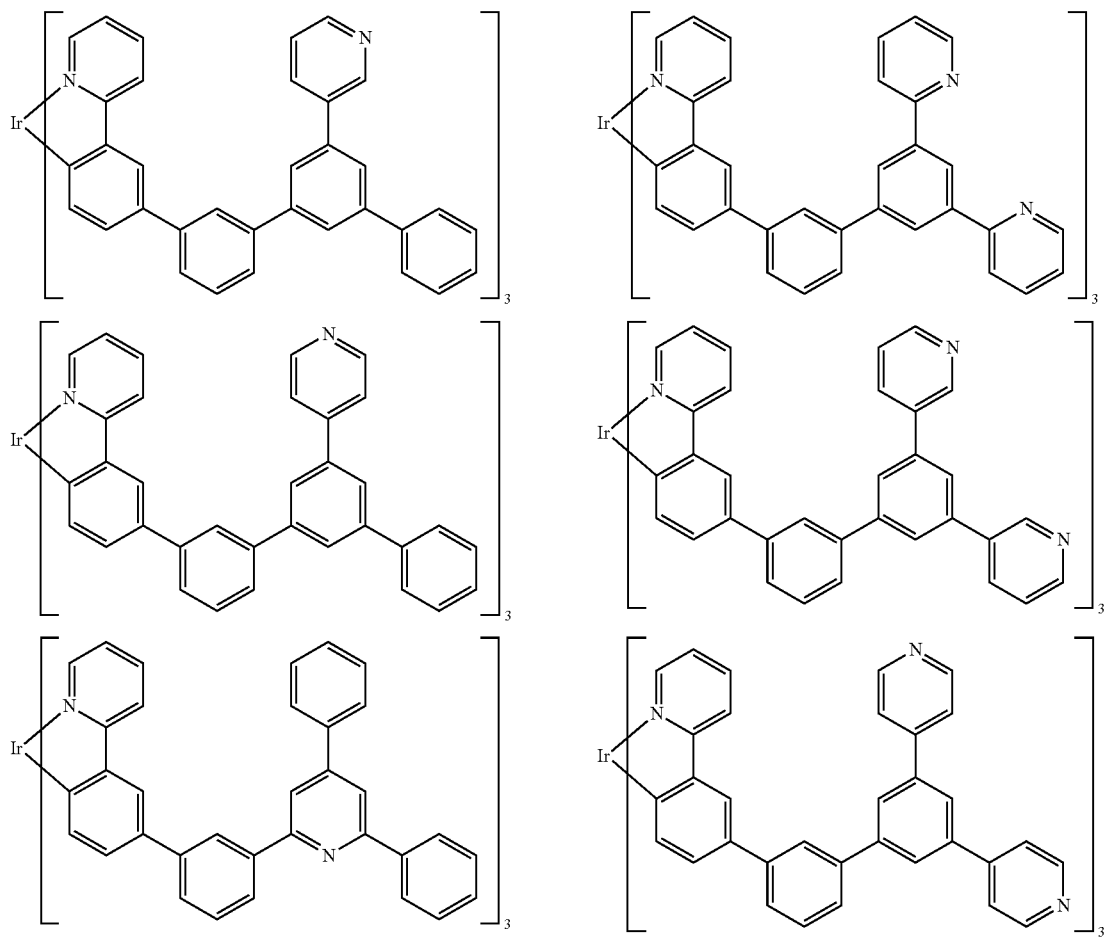

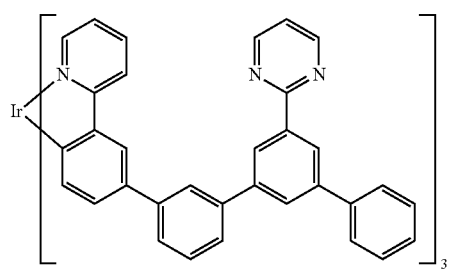
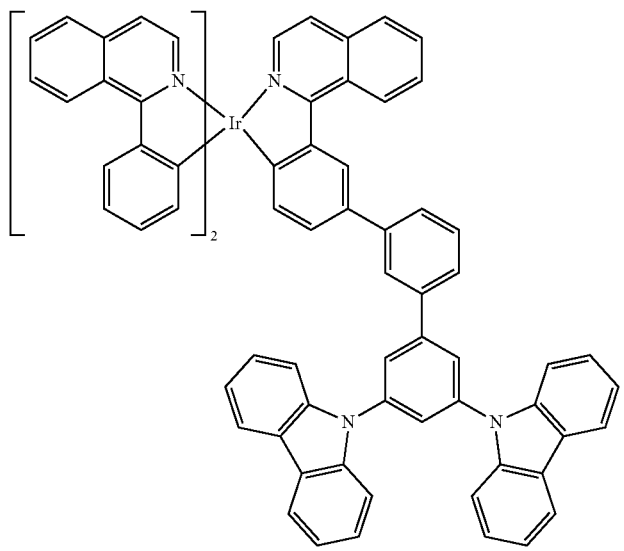
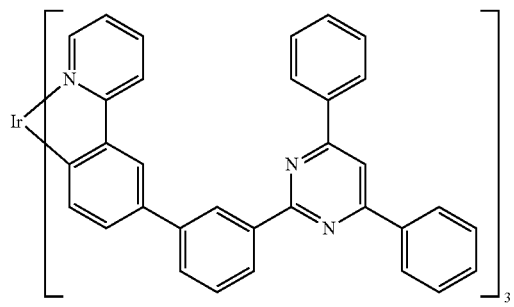
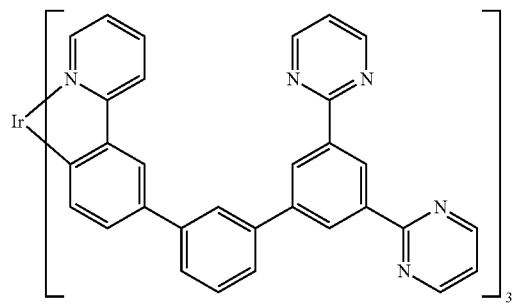
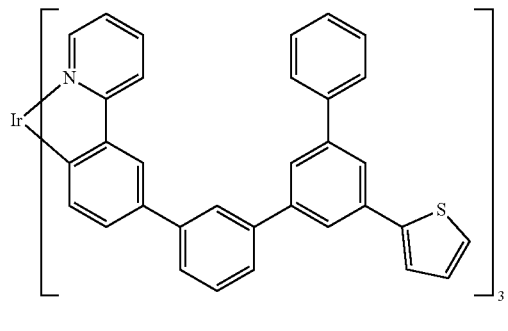
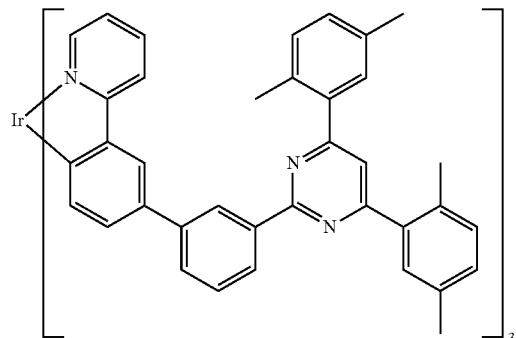

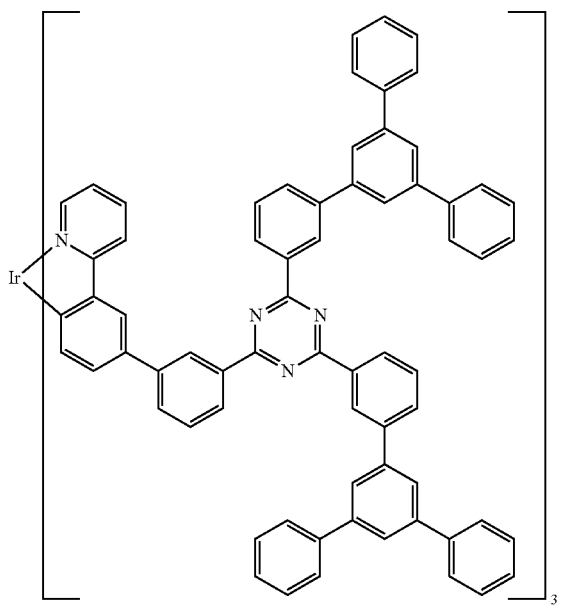
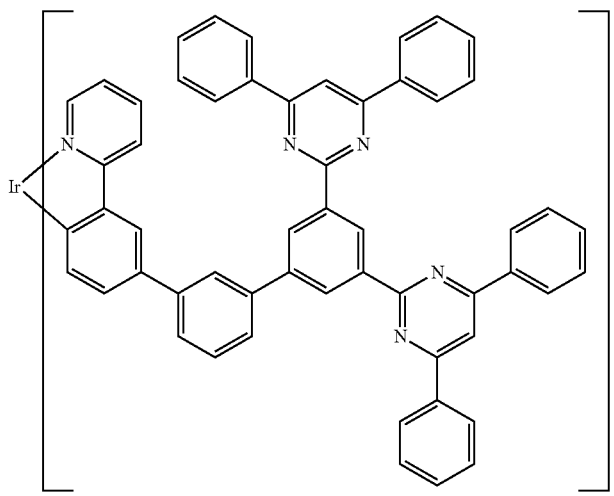
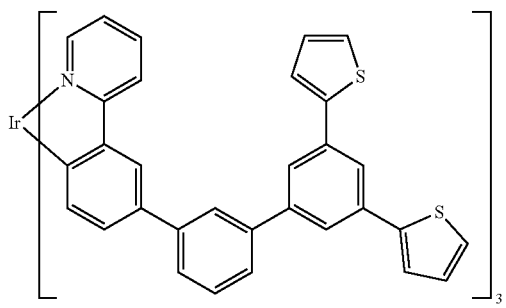
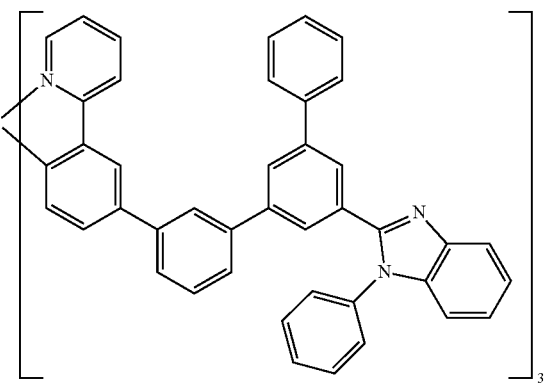

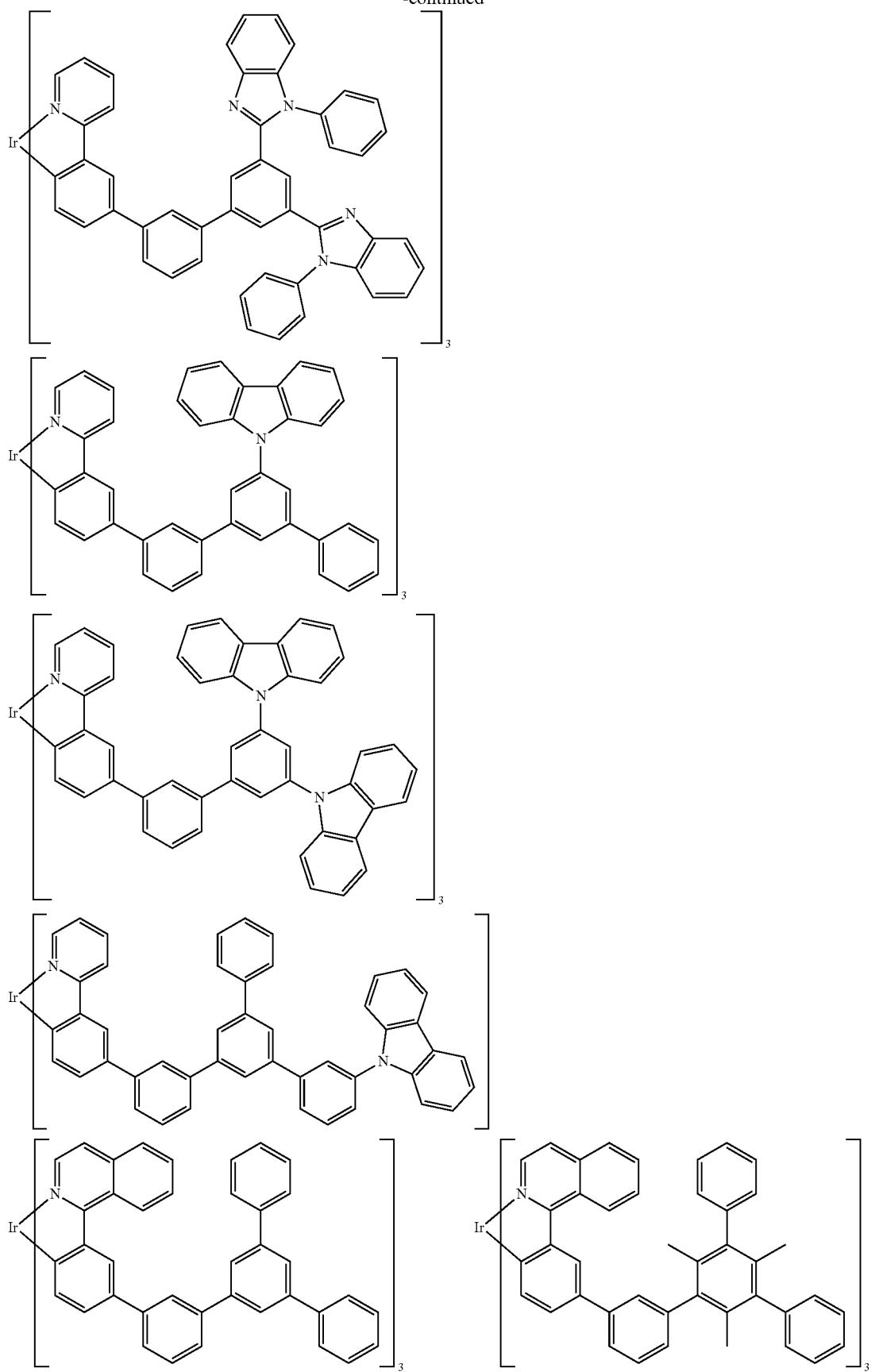

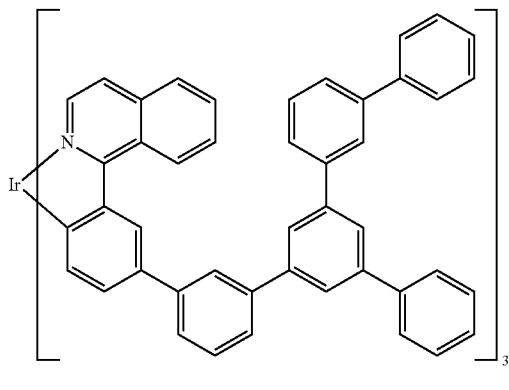
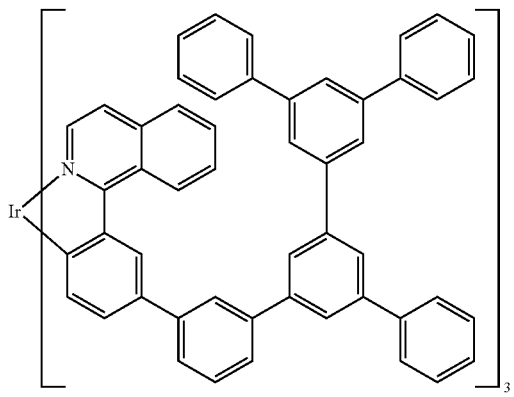
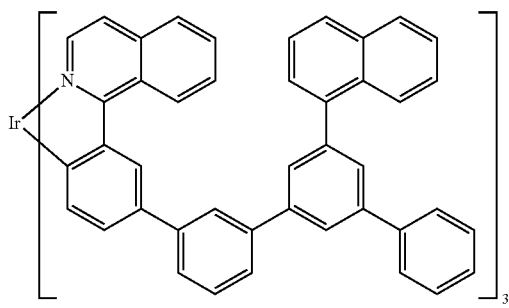
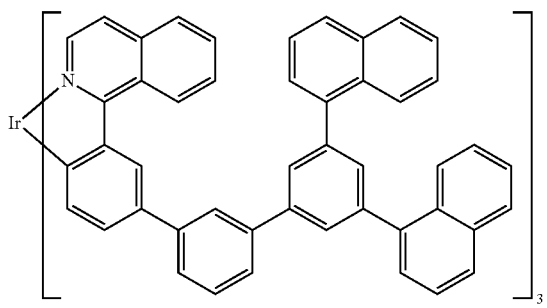
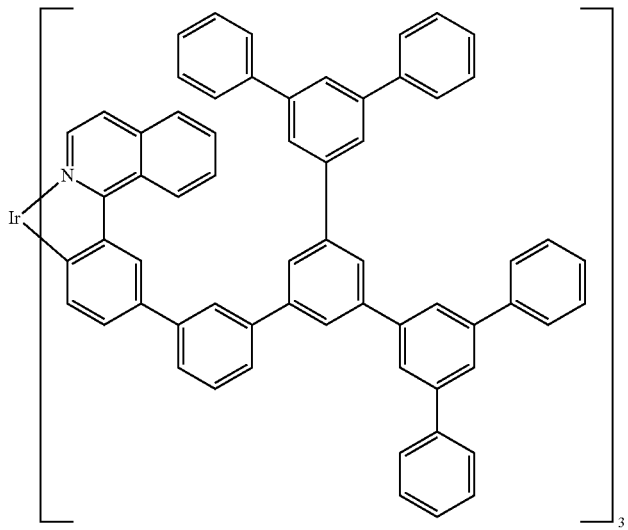
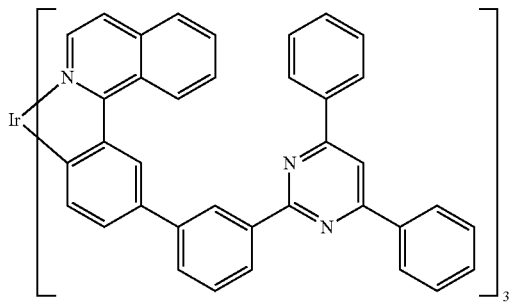

-continued
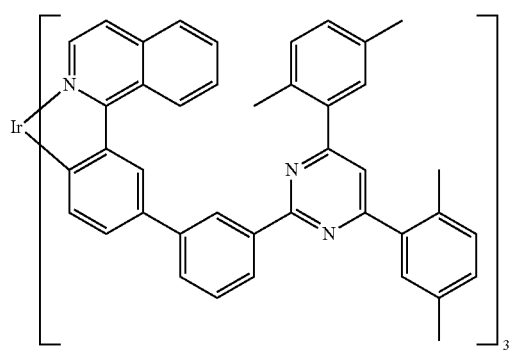
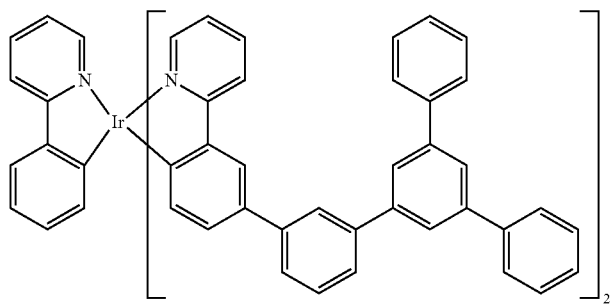
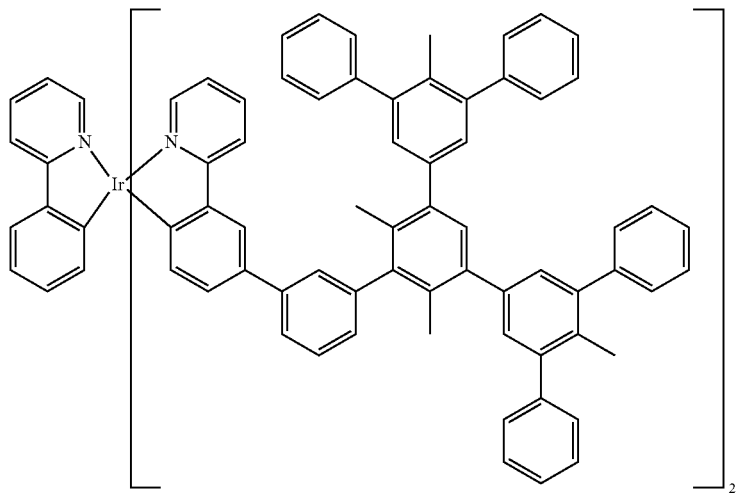
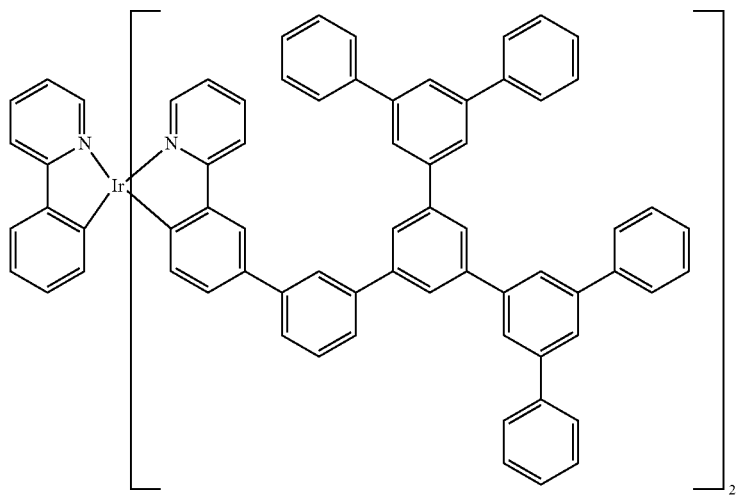

-continued
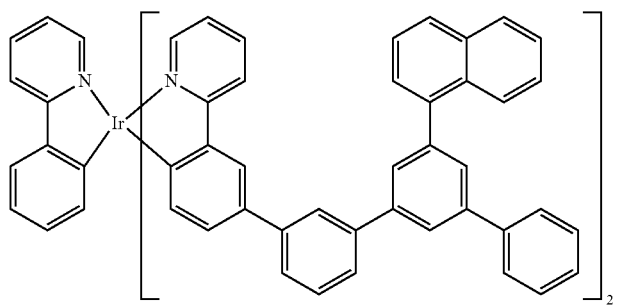
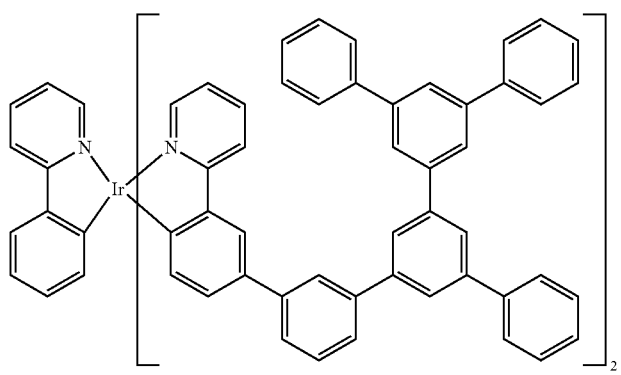
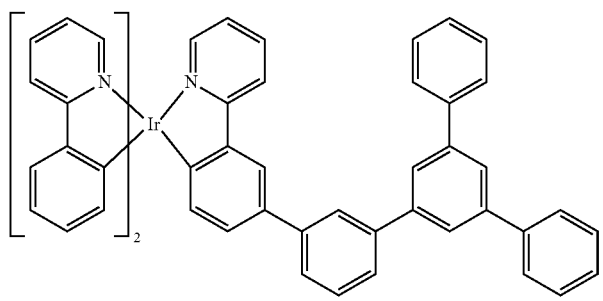
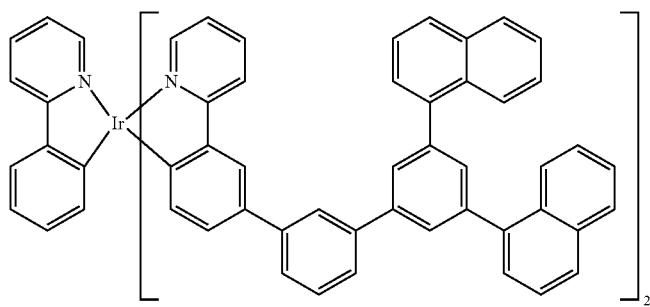

-continued
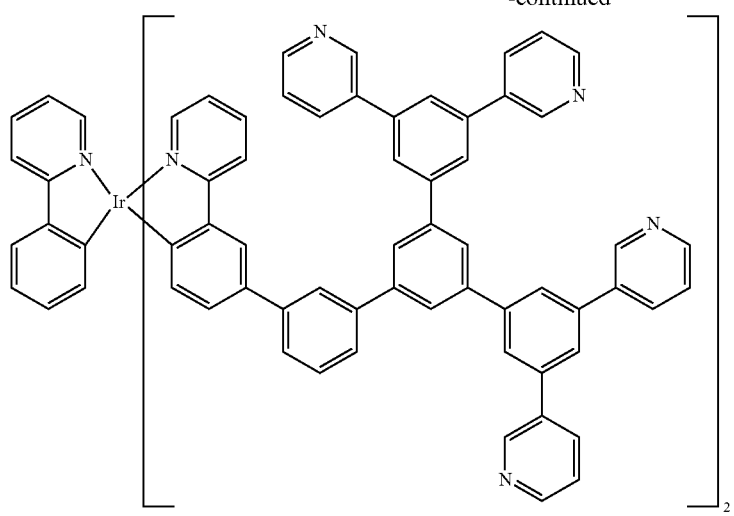
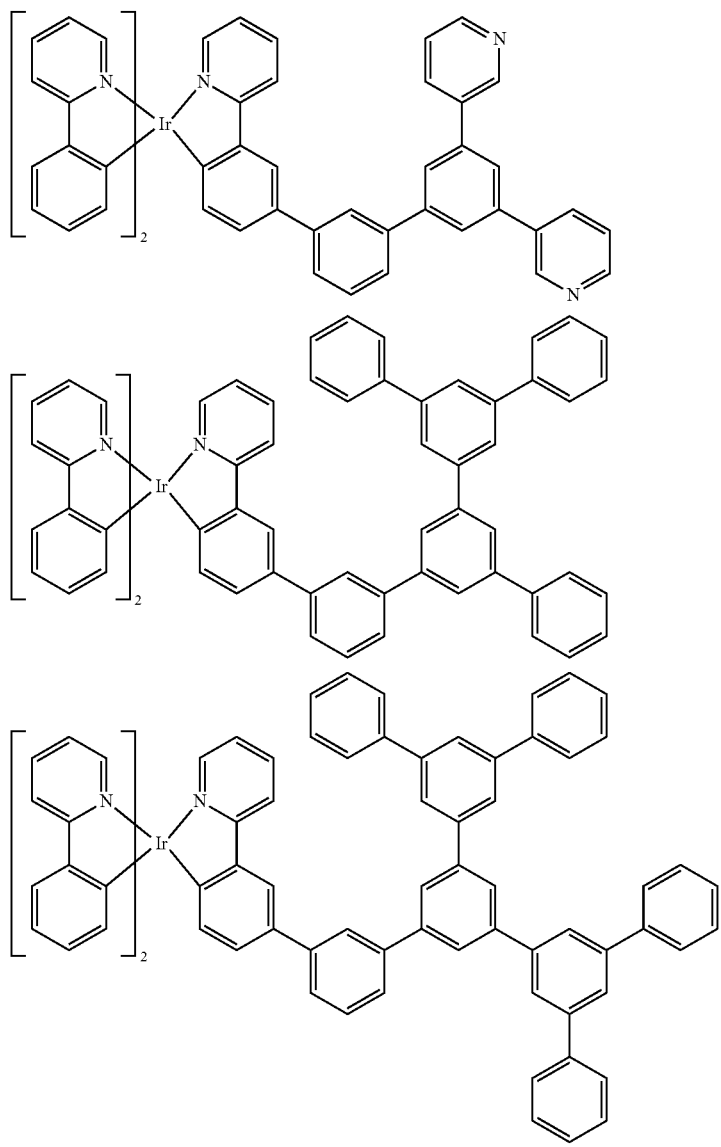

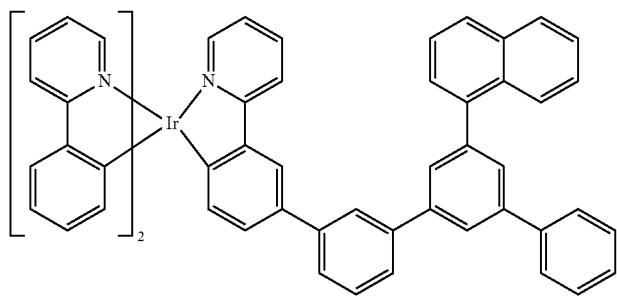
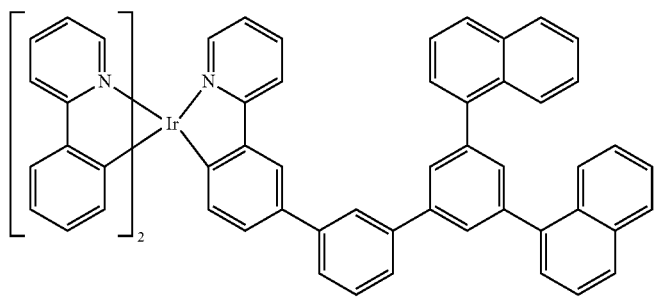
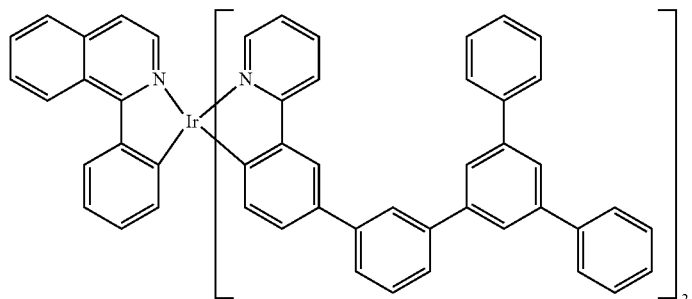
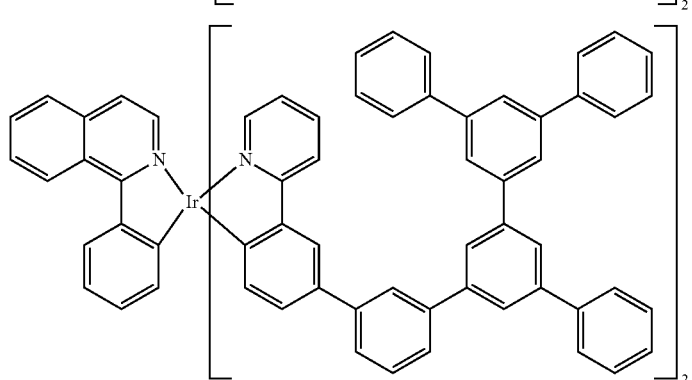
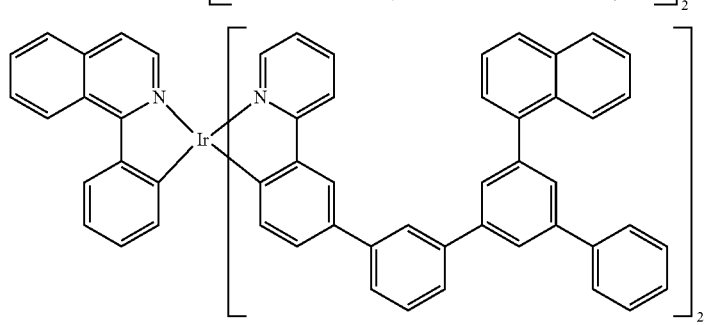

-continued
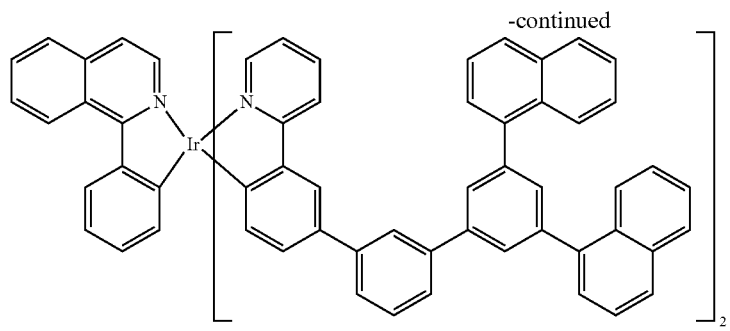
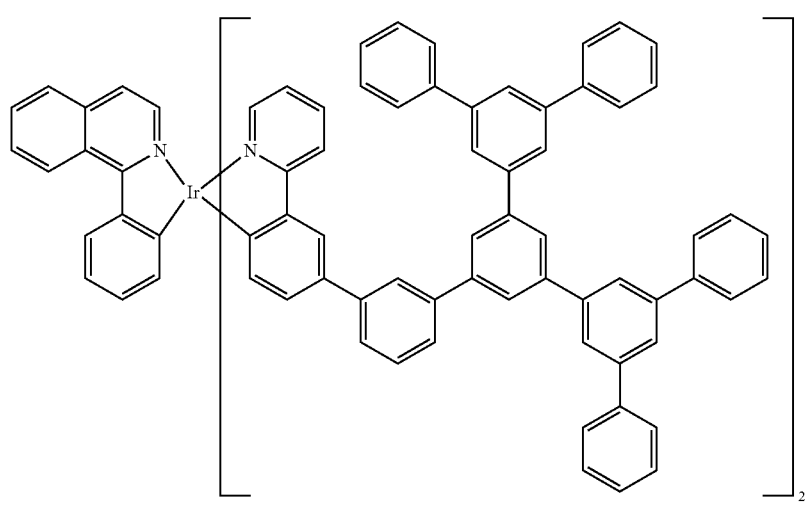
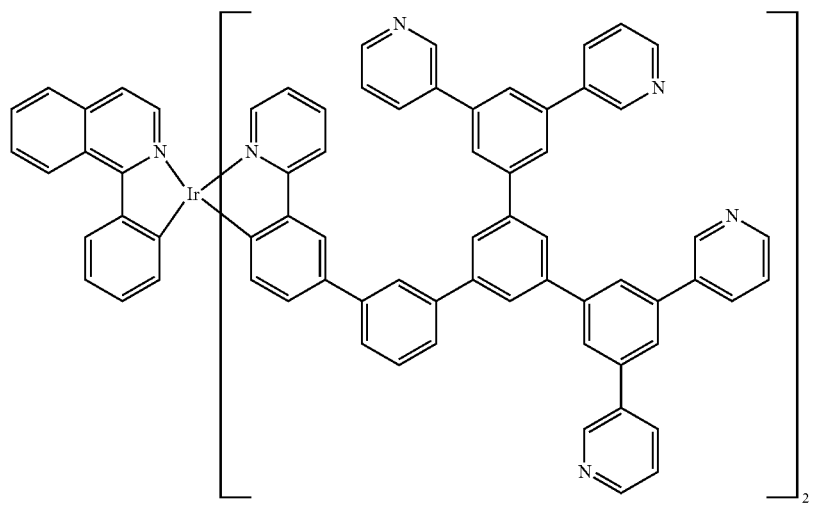
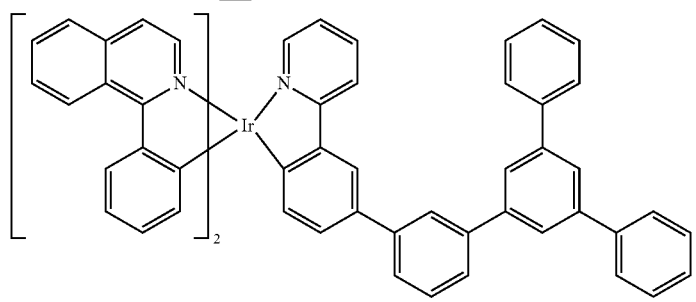

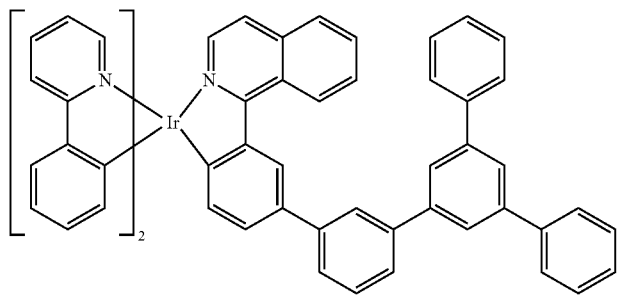
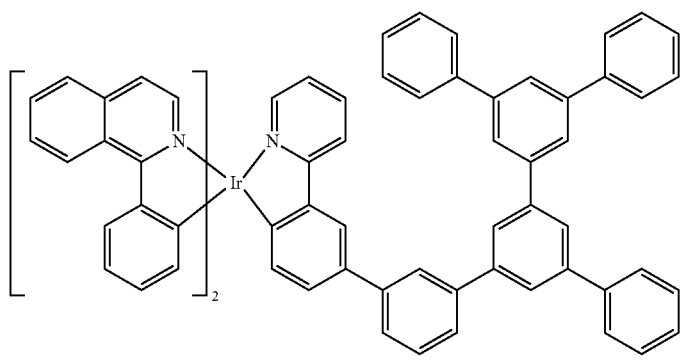
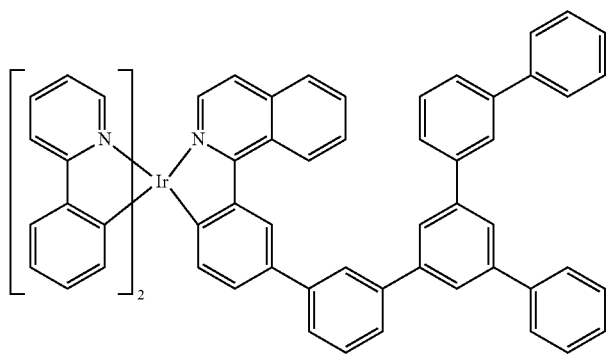
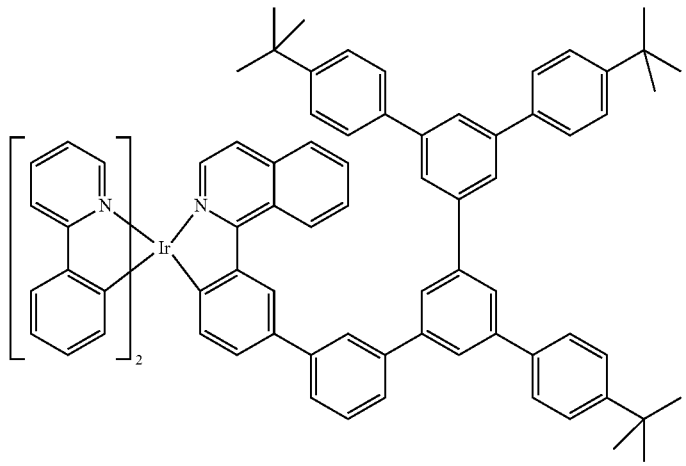

-continued
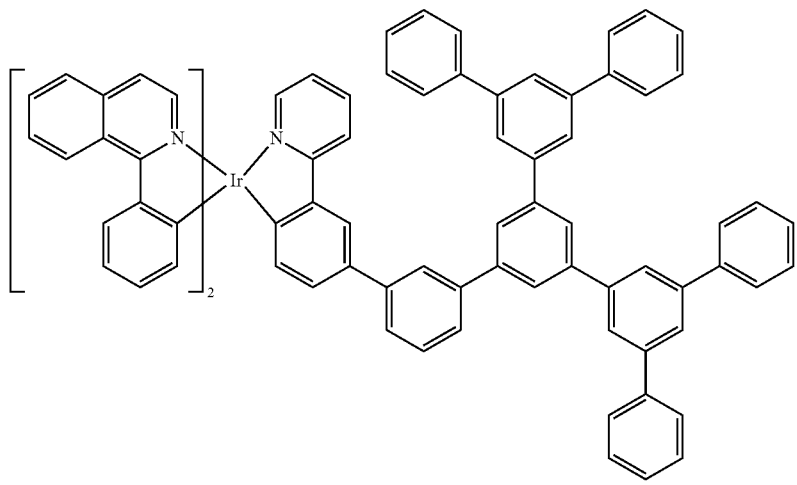
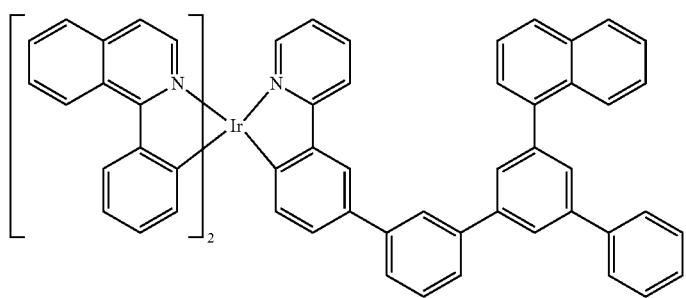
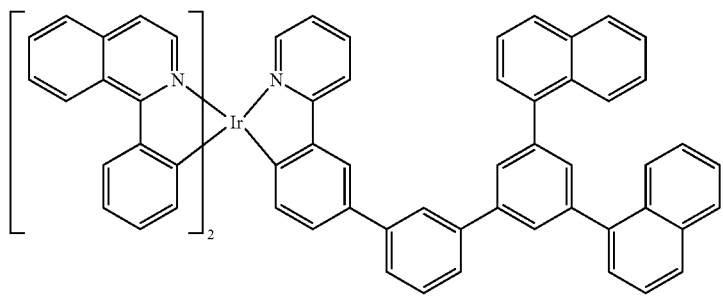
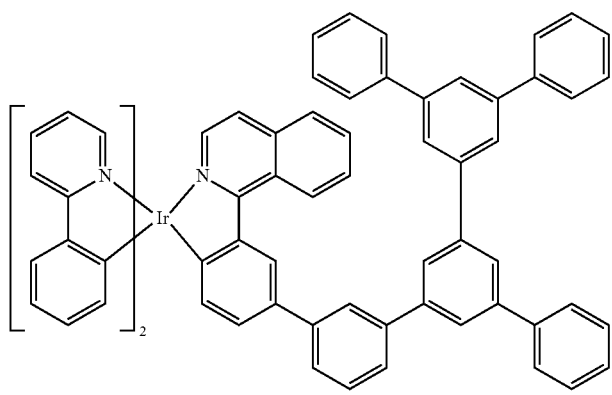

-continued
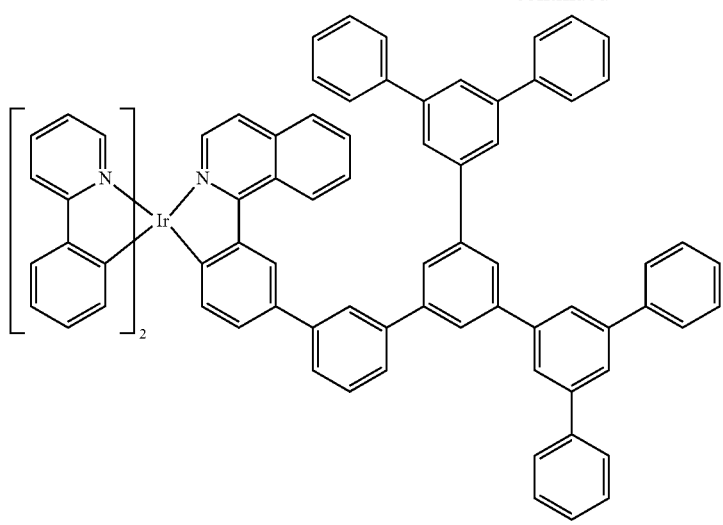
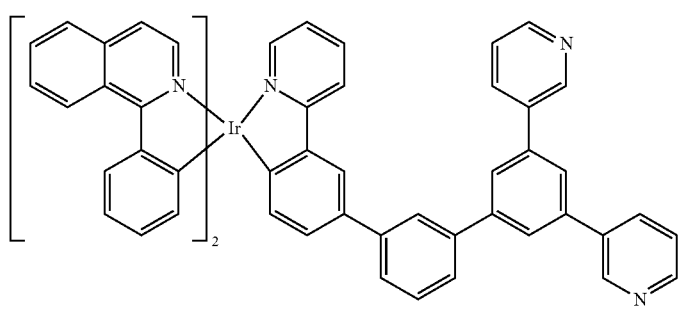
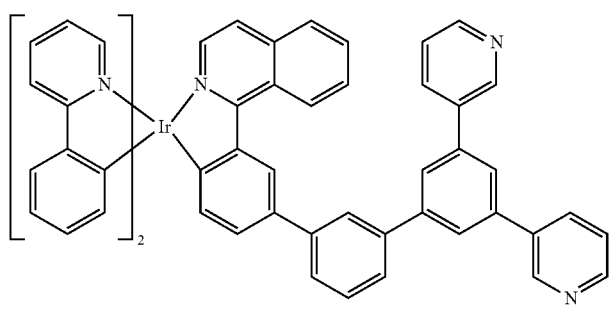
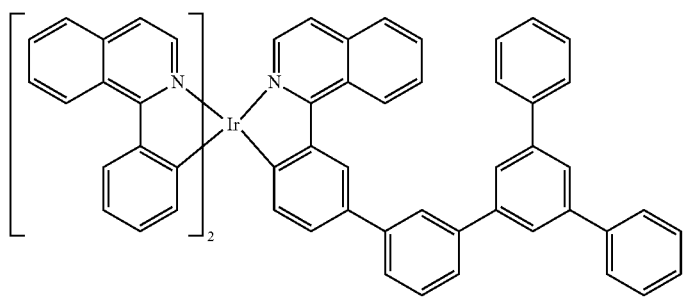

-continued
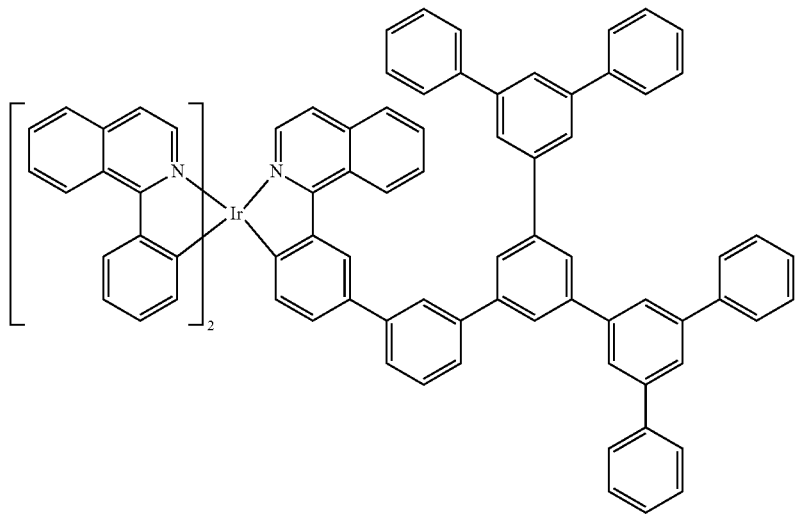
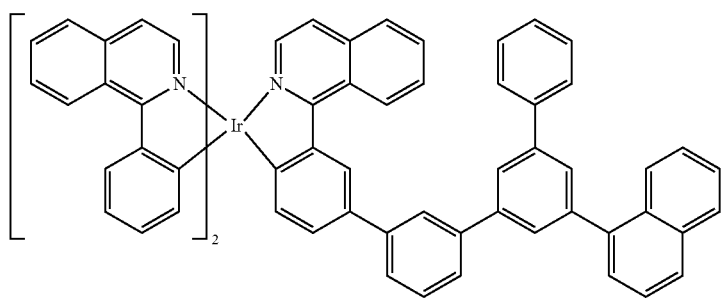
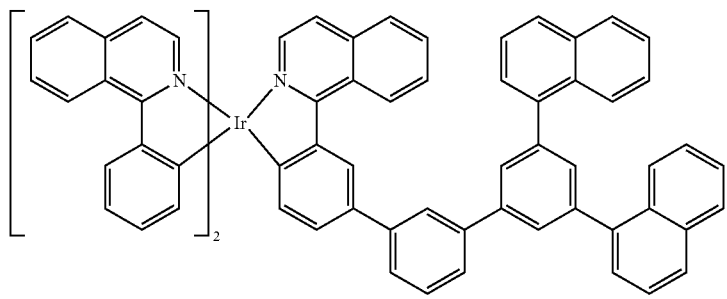
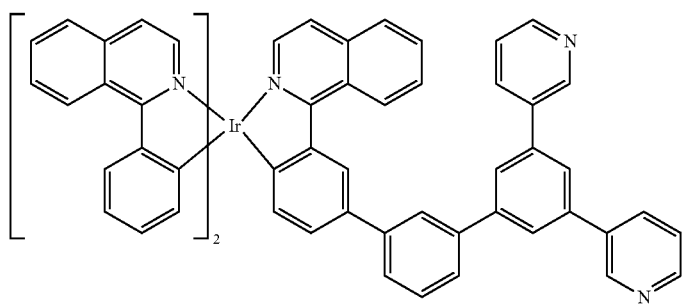

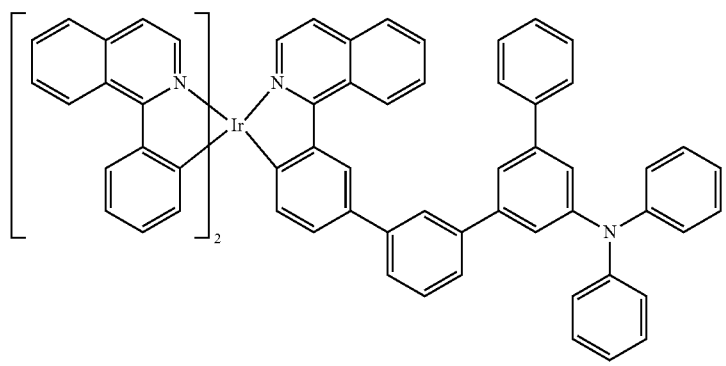
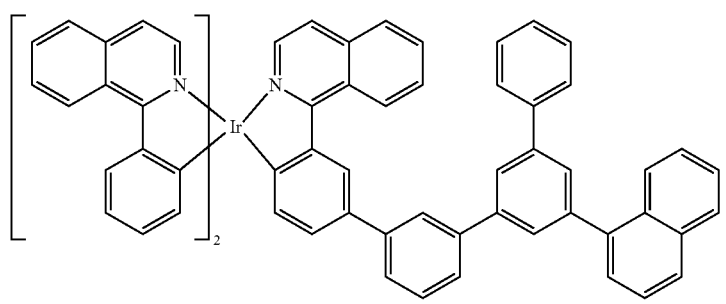
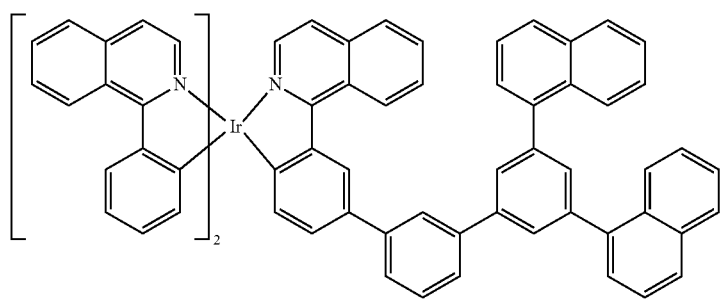
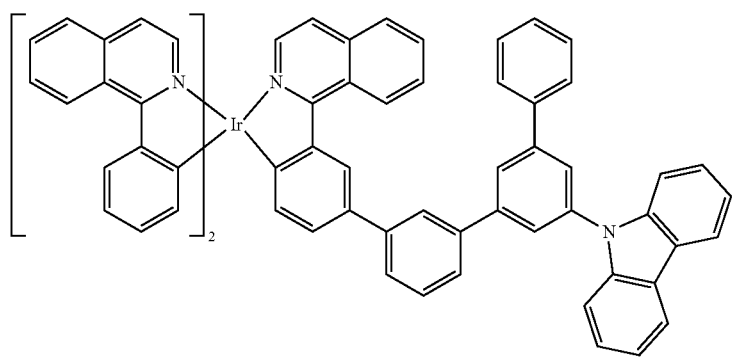

-continued
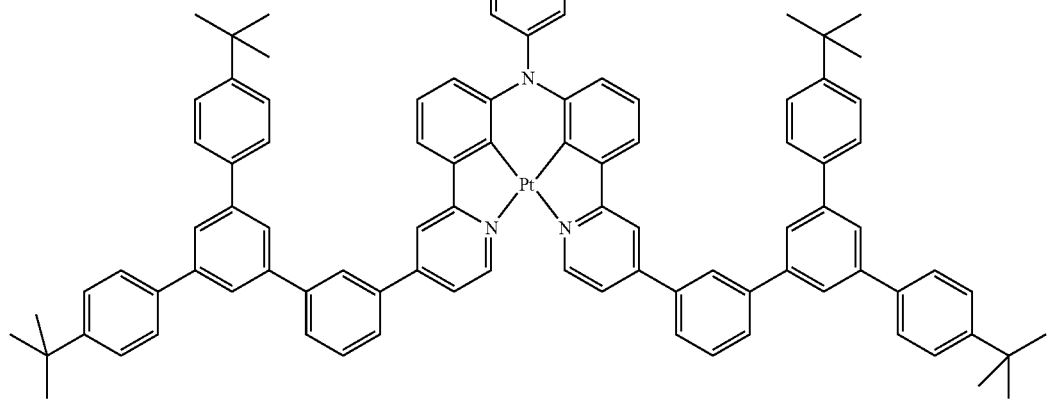
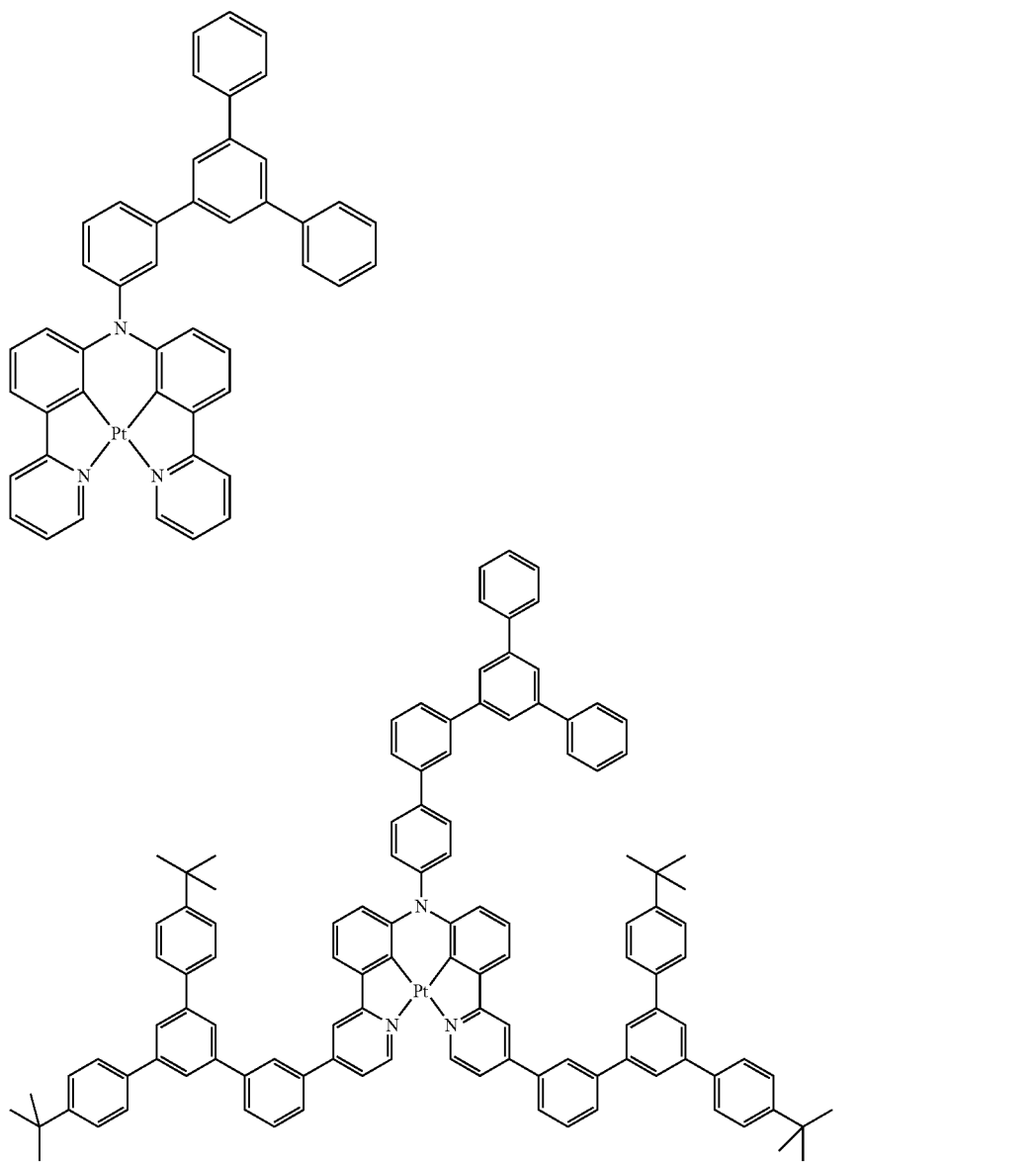

The formulation according to the invention is distinguished, in particular, by the presence of a mixture of at least two functional compounds of the formula (I).

The functional compounds here may comprise different functional structural elements A. For a first preferred embodiment, mention may be made by way of example of, in particular, mixtures which comprise at least one functional compound in which the functional structural element A in formula (I) is a unit which has light-emitting properties, and at least one functional compound in which the functional structural element A in formula (I) is a unit which can serve as host material.

In a second preferred embodiment, the mixture comprises at least one functional compound in which the functional structural element A in formula (I) is a unit which has light-emitting properties, and at least one functional compound in which the functional structural element A in formula (I) is a unit which can serve as hole-transport material.

In a third preferred embodiment, the mixture comprises at least one functional compound in which the functional structural element A in formula (I) is a unit which has light-emitting properties, and at least one functional compound in which the functional structural element A in formula (I) is a unit which can serve as electron-transport material.

In this connection, it may be explained that the compounds to be employed as host material may in some cases also serve as electron-transport material or as hole-transport material.

In a fourth preferred embodiment, the mixture comprises at least one functional compound in which the functional structural element A in formula (I) is a unit which has light-emitting properties, at least one functional compound in which the functional structural element A in formula (I) is a unit which can serve as hole-transport material, and at least one functional compound in which the functional structural element A in formula (I) is a unit which can serve as electron-transport material.

In a fifth preferred embodiment, the mixture comprises at least one functional compound in which the functional structural element A in formula (I) is a unit which can serve as hole-transport material, and at least one functional compound in which the functional structural element A in formula (I) is a unit which can serve as electron-transport material.

In a preferred embodiment, the proportion by weight of functional compound in which the functional structural element A in formula (I) is a unit which has light-emitting properties, based on all functional compounds in the formulation, is preferably in the range from 2 to 40% by weight, particularly preferably in the range from 3 to 30% by weight and in particular in the range from 5 to 25% by weight. Correspondingly, the proportion by weight of the at least one functional compound in which the functional structural element A in formula (I) is a unit which can serve as host material, based on all functional compounds in the formulation, is preferably in the range from 60 to 98% by weight, particularly preferably in the range from 70 to 97% by weight and in particular in the range from 75 to 95% by weight.

In a further preferred embodiment, the proportion by weight of functional compound in which the functional structural element A in formula (I) is a unit which has light-emitting properties, based on all functional compounds in the formulation, may, however, also preferably be in the range from 0.01 to 5% by weight, particularly preferably in the range from 0.05 to 3% by weight and in particular in the range from 0.1 to 2% by weight. Correspondingly, in this embodiment, the proportion by weight of the at least one functional compound in which the functional structural element A in formula (I) is a unit which can serve as host material, based on all functional compounds in the formulation, may preferably be in the range from 95 to 99.95% by weight, particularly preferably in the range from 97 to 99.9% by weight and in particular in the range from 98 to 99.9% by weight.

In addition, it is also possible to employ mixtures whose structural elements A exhibit the same functionalities. The preferred mixtures of this type include, in particular, formulation having at least two functional compounds in which the functional structural element A in formula (I) is a unit which can serve as host material.

Particular preference is given here to mixtures which comprise at least three functional compounds of the formula (I), where at least two functional compounds exhibit identical functionalities and at least one functional compound comprises a functionality which is different from the first. Particular preference is given, in particular, to a mixture having at least two functional compounds in which the functional structural element A in formula (I) is a unit which can serve as host material, and at least one functional compound in which the functional structural element A in formula (I) is a unit which has light-emitting properties The formulation according to the invention may also comprise functional compounds contain no solubility-promoting structural elements. However, these formulations frequently exhibit a lower performance profile than formulations which comprise exclusively functional compounds of the formula (I) as functionally active components. Accordingly, surprising advantages can be achieved, in particular, by formulations whose proportion of functional compounds which comprise no solubility-promoting structural element B of the general formula (L-I) is preferably at most 80% by weight, particularly preferably at most 50% by weight and very particularly preferably at most 10% by weight, based on the total weight of the functional compounds. According to a particular embodiment, the formulation according to the invention may comprise no functional compound which contains no solubility-promoting structural element, so that the formulation essentially consists of solvents, functional compounds of the formula (I) and additives.

According to a particular aspect of the present invention, formulations which comprise

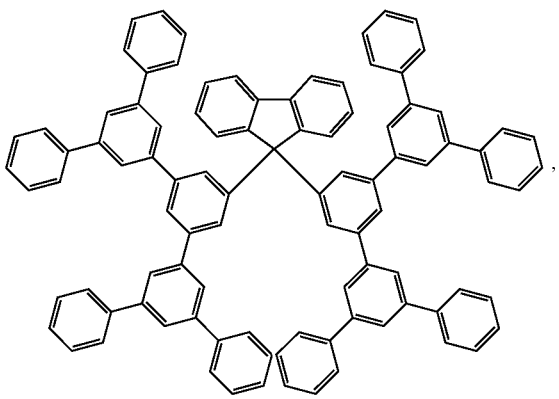

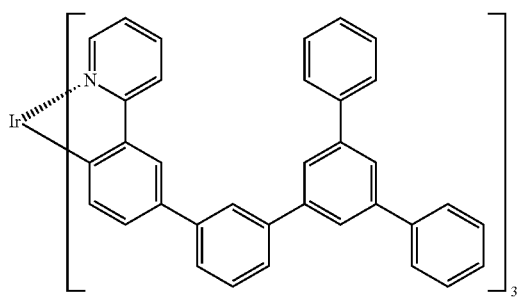

and

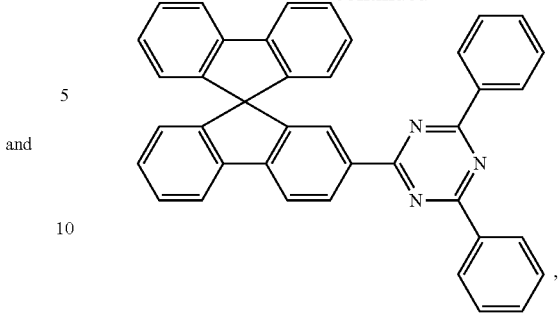

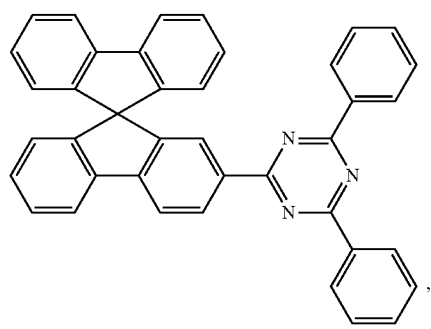

in particular, may be excluded.

Furthermore, formulations which comprise

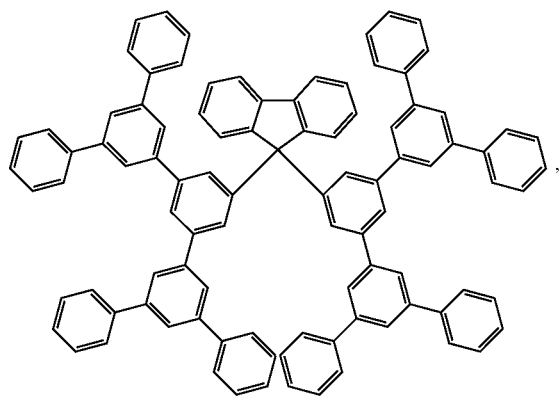,

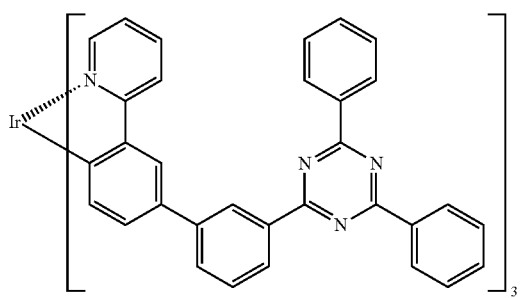

in particular, may be excluded from the present invention.

Furthermore, according to a particularly preferred point of view of the present invention, formulations which comprise

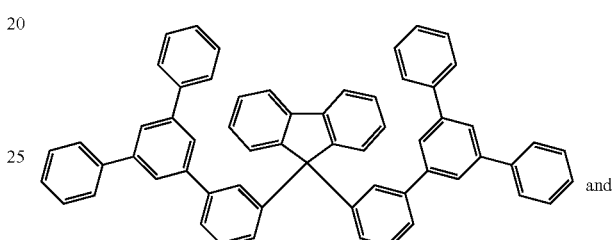

and

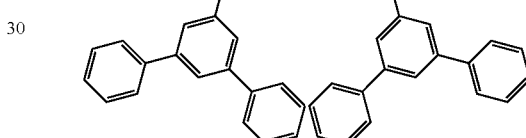

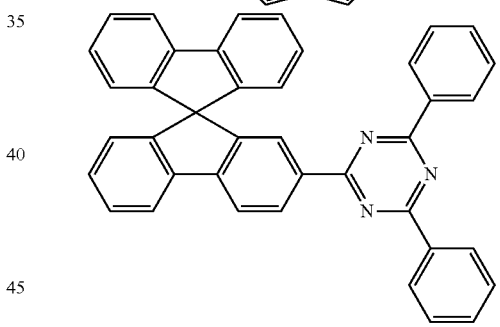

may be excluded.

Besides the said components, the formulation according to the invention may comprise further additives and processing assistants. These include, inter alia, surface-active substances, surfactants, lubricants and greases, additives which increase the conductivity, dispersants, hydrophobicising agents, adhesion promoters, flow improvers, antifoams, deaerating agents, diluents, which may be reactive or unreactive, fillers, assistants, processing assistants, dyes, pigments, stabilisers, sensitisers, nanoparticles and inhibitors.

Compounds which contain the structural units according to the invention are used, for example, for the production of OLEDs or other electronic devices, preferably as hole-transport, hole-injection, emitter, electron-transport, electron-injection, charge-blocking and/or charge-generation layer.

The functional layers can be produced, for example, by coating from solution, preferably spin coating, or using any desired printing process, such as, for example, screen printing, flexographic printing or offset printing, but particularly preferably LITI (light induced thermal imaging, thermal transfer printing) or ink-jet printing.

The present invention also relates to the use of the functional compound in an organic, electronic device.

The organic, electronic device is preferably an organic electroluminescent device (OLED), a polymeric electroluminescent device (PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser).

For the purposes of the present invention, it is preferred for the functional compound according to the invention to be in the form of a layer (or to be present in a layer) in the electronic device.

The present invention thus also relates to a layer, in particular an organic layer, comprising one or more compounds as defined above.

In a further embodiment of the present invention, the device comprises a plurality of layers. The compound according to the invention can preferably be present here in a hole-transport, hole-injection, electron-transport, electron-injection and/or emission layer. Particular preference is given to the use of the compounds according to the invention in the hole-transport and/or emission layer.

The present invention accordingly also relates to an electronic device which comprises at least three layers, but in a preferred embodiment all said layers, from hole-injection, hole-transport, emission, electron-transport, electron-injection, charge-blocking and/or charge-generation layer and in which at least one layer comprises a compound to be employed in accordance with the invention. The thickness of the layers, for example the hole-transport and/or hole-injection layer, can preferably be in the range from 1 to 500 nm, particularly preferably in the range from 2 to 200 nm.

The device may furthermore comprise layers built up from further low-molecular-weight compounds or polymers. These can also be produced by evaporation of low-molecular-weight compounds in a high vacuum.

It may additionally be preferred to use the compounds to be employed in accordance with the invention not as the pure substance, but instead as a mixture (blend) together with further polymeric, oligomeric, dendritic or low-molecular-weight substances of any desired type. These may, for example, improve the electronic properties or emit themselves. The present application therefore likewise relates to mixtures of this type.

In a preferred embodiment of the present invention, the compounds according to the invention are employed as host materials or matrix materials in an emitting layer. The organic electroluminescent device here may comprise one or more emitting layers, where at least one emitting layer comprises at least one compound according to the invention, as defined above. If a plurality of emission layers are present, these preferably have a plurality of emission maxima between 380 nm and 750 nm, resulting overall in white emission, i.e. various emitting compounds which are able to fluo-resce or phosphoresce are used in the emitting layers. Very particular preference is given to three-layer systems, where the three layers exhibit blue, green and orange or red emission (for the basic structure see, for example, WO 05/011013). White-emitting devices are suitable, for example, as back-lighting of LCD displays or for general lighting applications.

Apart from these layers, the organic electroluminescent device may also comprise further layers, for example in each case one or more hole-injection layers, hole-transport layers, hole-blocking layers, electron-transport layers, electron-injection layers, exciton-blocking layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). Likewise, interlayers which have, for example, an exciton-blocking function may be introduced between two emitting layers. However, it should be pointed out that each of these layers does not necessarily have to be present. These layers may likewise comprise the compounds according to the invention, as defined above. It is also possible for a plurality of OLEDs to be arranged one above the other, enabling a further increase in efficiency with respect to the light yield to be achieved. In order to improve the coupling-out of light, the final organic layer on the light-exit side in OLEDs can, for example, also be in the form of a nanofoam, resulting in a reduction in the proportion of total reflection.

Preference is furthermore given to an organic electroluminescent device in which one or more layers are applied by means of a sublimation process, in which the materials are applied by vapour deposition in vacuum-sublimation units at a pressure below $10^{-5}$ mbar, preferably below $10^{-6}$ mbar, particularly preferably below $10^{-7}$ mbar.

Preference is likewise given to an organic electroluminescent device which is characterised in that one or more layers are applied by means of the OVPD (organic vapour phase deposition) process or with the aid of carrier-gas sublimation, in which the materials are applied at a pressure between $10^{-5}$ mbar and 1 bar.

Preference is furthermore given to an organic electroluminescent device which is characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing.

The device usually comprises a cathode and an anode (electrodes). The electrodes (cathode, anode) are selected for the purposes of the present invention in such a way that their band energies correspond as closely as possible to those of the adjacent, organic layers in order to ensure highly efficient electron or hole injection.

The cathode preferably comprises metal complexes, metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali-metal or alkaline-earth metal fluorides, but also the corresponding oxides (for example LiF, $Li_2O$, $BaF_2$, MgO, NaF, etc.). The layer thickness of this layer is preferably between 1 and 10 nm, particularly preferably between 2 and 8 nm.

The anode preferably comprises materials having a high work function. The anode preferably has a potential greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent in order to facilitate either irradiation of the organic material (O-SCs) or the coupling-out of light (OLEDs/PLEDs, O-lasers). A preferred structure uses a transparent anode. Preferred anode materials here are conductive, mixed metal oxides. Particular preference is given to indium tin oxide (ITO) or indium zinc oxide (IZO). Preference is furthermore given to conductive, doped organic materials, in particular conductive, doped polymers, such as, for example, poly(ethylenedioxythiophene) (PEDOT) and polyaniline (PANI).

The present invention likewise relates to a process for the production of an electronic device in which a formulation according to the invention is applied to a substrate and dried.

The solvent can preferably be removed at a temperature in the range from −50° C. to 300° C., particularly preferably in the range from 20° C. to 250° C.

The drying here can be carried out at a pressure in the range from 10$^{-3}$ mbar to 1 bar, particularly preferably in the range from 10$^{-2}$ mbar to 100 mbar.

The device is correspondingly structured, provided with contacts and finally hermetically sealed in a manner known per se, depending on the application, since the lifetime of such devices is drastically shortened in the presence of water and/or air.

The invention is explained in greater detail below with reference to working examples, but without being restricted thereby.

WORKING EXAMPLES

Example 1: Synthesis of Compounds 3 and 4

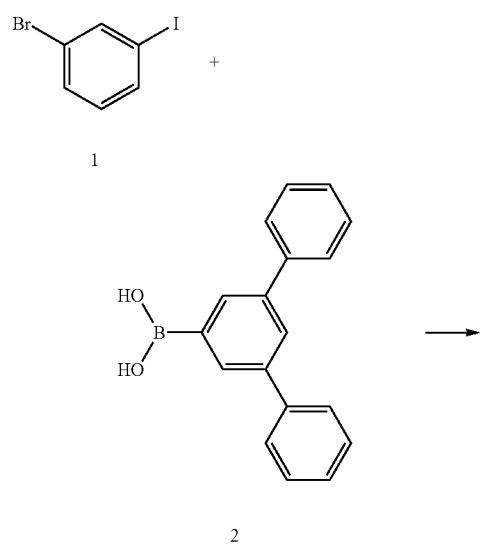

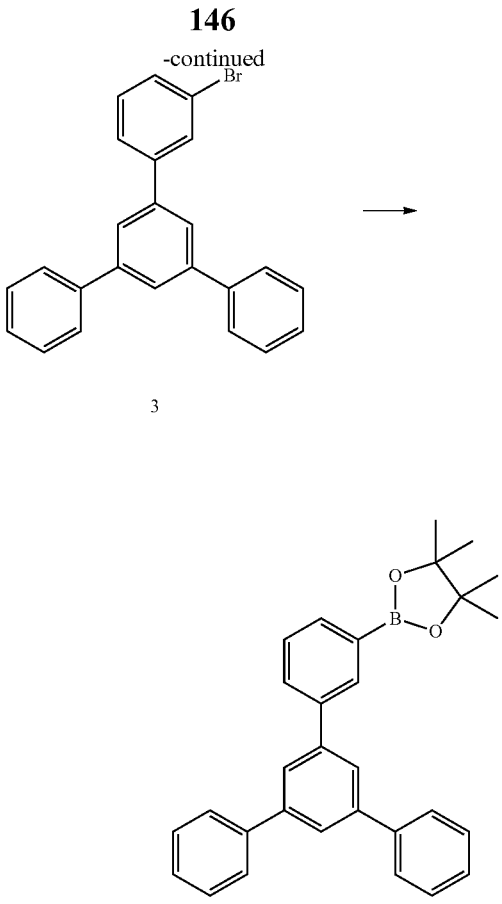

Synthesis of Compound 3

40.0 g (146 mmol) of 3-borono-[3,1';5,1"]terphenyl 2, 18.8 g (146 mmol) of 1-iodo-3-bromophenyl (1) and 109.3 g (730 mmol) of potassium carbonate are suspended in 1350 ml of toluene and 1150 ml of water. 844 mg (0.73 mmol) of tetrakis(triphenylphosphine)palladium(0) are added to this suspension, and the reaction mixture is heated under reflux for 16 hours. After cooling, the organic phase is separated off, washed three times with 200 ml of water, dried using sodium sulfate and subsequently evaporated to dryness. The residue is washed with ethanol and recrystallised from ethyl acetate and finally dried under reduced pressure. The yield is 47.6 g (123 mmol), corresponding to 84.5% of theory.

Synthesis of Compound 4

40.0 g (104 mmol) of 1-bromo-3-([3,1';5,1"]terphen-1-yl)phenyl 3, 29.0 g (114 mmol) of bispinacolatodiboron, 29.5 g (301 mmol) of potassium acetate are suspended in 800 ml of dimethyl sulfoxide. 4.24 g (5.2 mmol) of 1,1-bis(diphenylphosphino)ferrocenepalladium(II) dichloride DCM are added to this suspension, and the reaction mixture is heated under reflux for 16 hours. After cooling, 600 ml of ethyl acetate and 400 ml of water are added, and the organic phase is separated off, washed three times with 200 ml of water, dried using sodium sulfate and subsequently evaporated to dryness. The crude product is recrystallised from heptane and finally dried under reduced pressure. The yield is 34.5 g (80 mmol), corresponding to 46.1% of theory.

Example 2

Synthesis of Compound 5

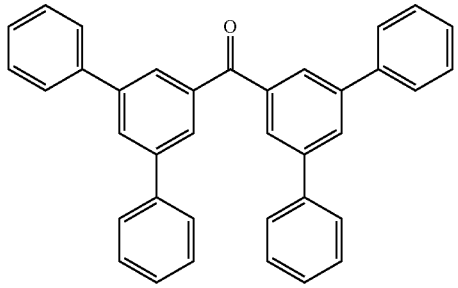

74.7 g (150 mmol) of bis(3,5-dibromophenyl) ketone, 109.7 g (900 mmol) of phenylboronic acid, 267.5 g (1162 mmol) of tripotassium phosphate mono-hydrate, 5.5 g (18 mmol) of tri-o-tolylphosphine and 673.5 mg (3 mmol) of palladium(II) acetate are suspended in a mixture of 600 ml of toluene, 300 ml of dioxane and 750 ml of water and heated under reflux for 72 hours. After cooling, the organic phase is separated off, washed three times with water and dried over sodium sulfate. The mixture is subsequently filtered through aluminium oxide, evaporated to about 200 ml, and 500 ml of ethanol are added, whereupon the crude product precipitates. The solid is filtered off with suction and washed with 100 ml of ethanol, then dissolved in boiling toluene and re-precipitated by addition of hot ethanol. The yield is 44.0 g (90 mmol), corresponding to 60.2% of theory.

Example 3: Synthesis of Compound 6

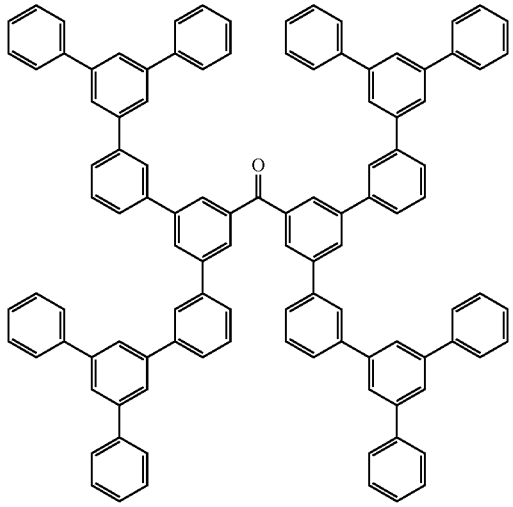

The synthesis is carried out analogously to compound 5, with phenylboronic acid being replaced by 1-bromo-3-([3,1';5,1"]-terphen-1-yl)phenyl 3. The yield is 123.2 g (88 mmol), corresponding to 58.7% of theory.

Example 4: Synthesis of Compound 7

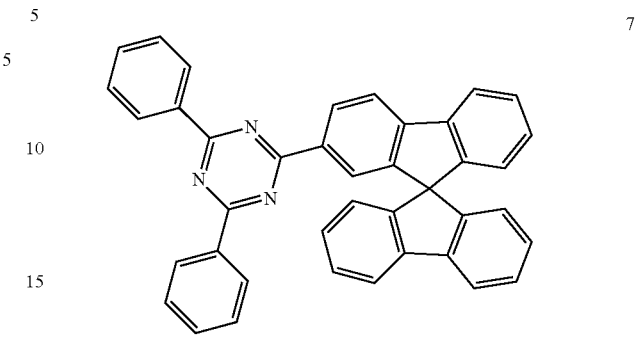

28.0 g (50.0 mmol) of spiro-9,9'-bifluorene-2-boronic acid, 14.7 g (55.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 hours. After cooling, the organic phase is separated off, filtered through silica gel, washed three times with 200 ml of water and subsequently evaporated to dryness. The residue is recrystallised from toluene and finally sublimed in high vacuum. The yield is 38 g (41.5 mmol), corresponding to 95.0% of theory.

Example 5: Synthesis of Compound 8

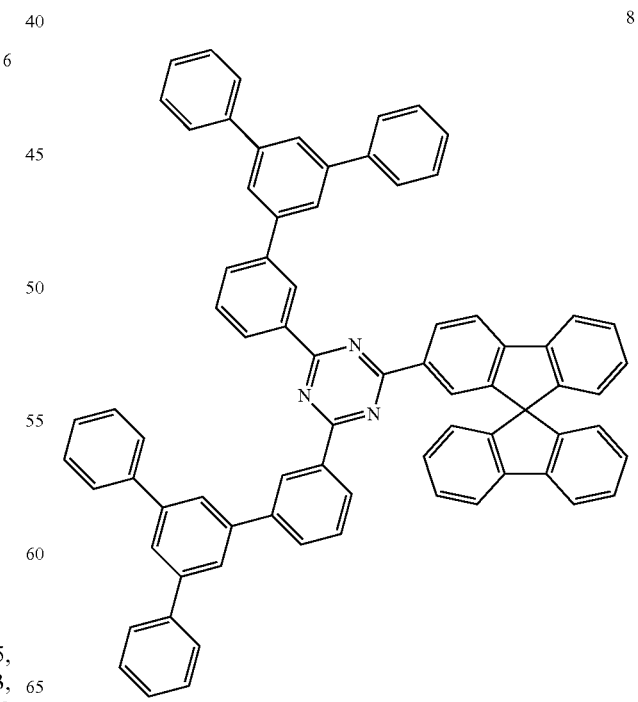

a) Synthesis of 2-chloro-4,6-bis(3-([3,1';5,1"]ter-phen-1-yl)phen-1-yl)-1,3,5-triazine 80.2 ml of a 2.0 molar solution of n-butyllithium in hexane were slowly added dropwise to a solution, cooled to −78° C., of 43.88 g (143 mmol) of 1-bromo-3-([3,1';5,1"]terphen-1-yl)phenyl in 250 ml of abs. tetrahydrofuran, and the mixture is stirred for 15 minutes. The reaction solution is slowly added dropwise to a solution, cooled to −78° C., of 10.0 g (45 mmol) of cyanuric chloride in 400 ml of abs. tetrahydrofuran, and the cooling is removed. When room temperature has been reached, the precipitated product is filtered off. The yield is 6.3 g (9.0 mmol), corresponding to 23.3% of theory.

b) Synthesis of 2-(4,6-bis(3-([3,1';5,1"]terphen-1-yl)phen-1-yl)-1,3,5-triazin-2-yl)spiro-9,9'-bifluorene The synthesis is carried out analogously to compound 7 with 4.07 g (11.3 mmol) of spiro-9,9'-bifluorene-2-boronic acid, with 2-chloro-4,6-diphenyl-1,3,5-triazine being replaced by 6.3 g (9.0 mmol) of 2-chloro-4,6-bis-(3-([3,1';5,1"]-terphen-1-yl)phen-1-yl)-1,3,5-triazine. The yield is 4.9 g (4.8 mmol), corresponding to 56.3% of theory.

Example 6: Synthesis of Compound 9

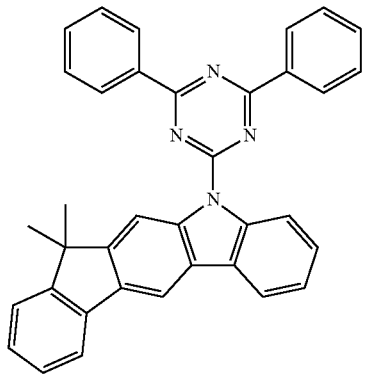

9

8 g (28.2 mmol) of 12,12-dimethyl-10,12-dihydro-10-azaindeno[2,1-b]fluorene are dissolved in 225 ml of dimethylformamide under a protective-gas atmosphere, and 1.5 g of NaH, 60% in mineral oil (37.5 mmol), are added. After 1 hour at room temperature, a solution of 2-chloro-4,6-diphenyl-1,3,5-triazine (8.5 g, 31.75 mmol) in 75 ml of dimethylformamide is added dropwise. The reaction mixture is then stirred at room temperature for 12 hours. After this time, the reaction mixture is poured onto ice and extracted three times with dichloromethane. The combined organic phases are dried over Na$_2$SO$_4$ and evaporated. The residue is extracted with hot toluene. The yield is 12 g (23 mmol), corresponding to 83% of theory.

Example 7: Synthesis of Compound 10

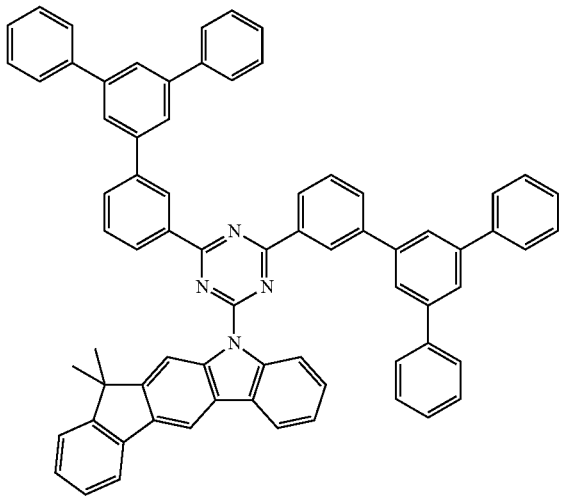

10

8.0 g (28 mmol) of 12,12-dimethyl-10,12-dihydro-10-azaindeno[2,1-b]fluorene are dissolved in 210 ml of dimethylformamide under a protective-gas atmosphere, and 1.4 g of NaH 60% in mineral oil (35 mmol), are added. After 1 hour at room temperature, a solution of 2-chloro-[4,6-bis-5'-(3-bromophenyl)-[1,1';3',1" ]terphenyl-5'-yl]-1,3,5-triazine (22.5 g, 31 mmol) in 250 ml of dimethylformamide is added dropwise. The reaction mixture is stirred at room temperature for 12 hours. After this time, the reaction mixture is poured onto ice and extracted three times with dichloromethane. The combined organic phases are dried over Na$_2$SO$_4$ and evaporated. The residue is recrystallised from heptane/toluene. The yield is 12.2 g (13 mmol), corresponding to 44% of theory.

Example 8: Synthesis of Compound 11

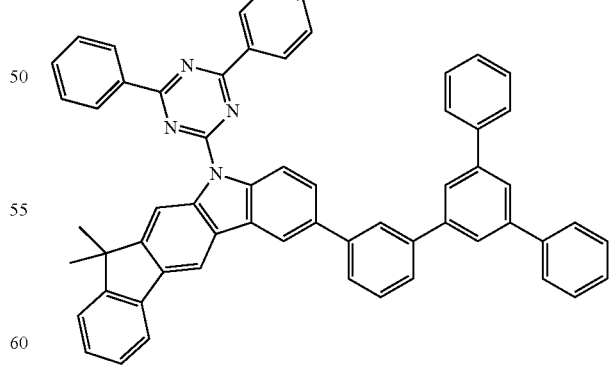

11

25.0 g (42.1 mmol) of 7-bromo-10-(4,6-diphenyl-1,3,5-triazin-2-yl)-12,12-dimethyl-10,12-dihydro-10-azaindeno[2,1-b]fluorene and 19.9 g of 1-pinacolylboronato-3-([3,1';5,1"]terphen-1-yl)phenyl (46.3 mmol) are dissolved in 80 ml of toluene and degassed. 281 ml of degassed 2 M K$_2$CO$_3$ and 2.4 g (2.1 mmol) of Pd(PPh$_3$)$_4$ are added. The reaction mixture is subsequently stirred at 80° C. for 48 hours under a protective-gas atmosphere. Toluene is added to the cooled solution, and the mixture is washed a number of times with water, dried and evaporated. The residue is recrystallised from heptane/toluene. The yield is 21.8 g (26.6 mmol), corresponding to 63.2% of theory.

Example 9: Synthesis of Compound 12

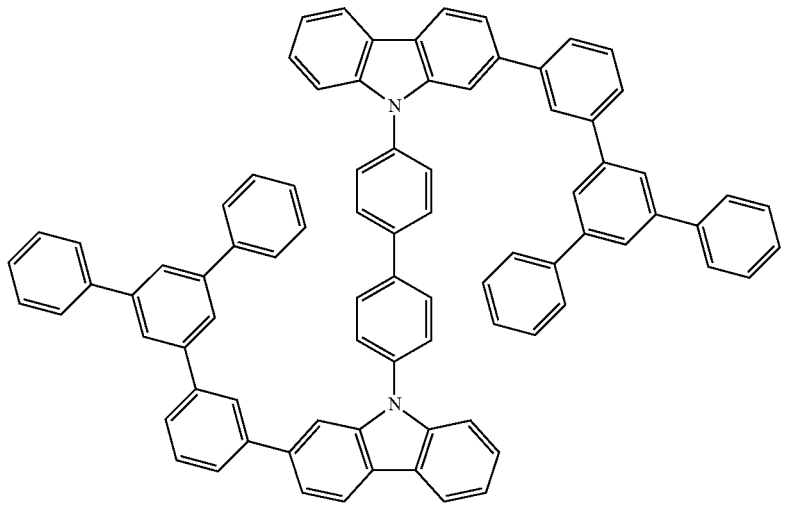

12

Compound 12 is prepared as described in WO 2008/086851 A1.

Example 10: Synthesis of Compound

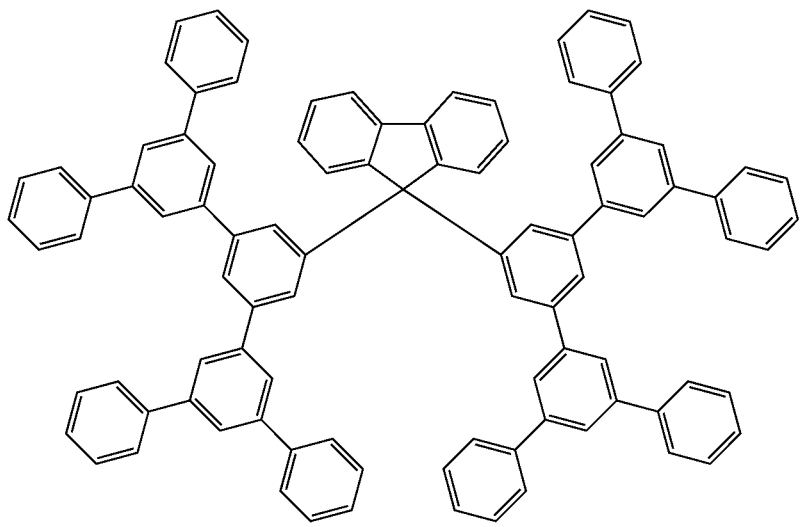

13

Compound 13 is prepared as described in WO 2009/124627.

Example 11: Synthesis of Compound 14

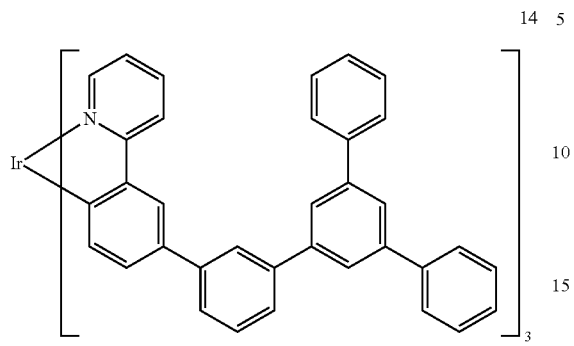

1.7 g (2.0 mmol) of fac-tris[2-(2-pyridinyl-κN)(5-bromophenyl)-κC]-iridium(III), 7.42 g (17 mmol) of 1-pinacolylboronato-3-([3,1';5,1"]terphen-1-yl)benzene, 2.51 g (12 mmol) of potassium phosphate are suspended in 100 ml of toluene, 100 ml of dioxane and 111 ml of water. 4 mg (0.1 mmol) of palladium(II) acetate and 35 mg (0.2 mmol) of tri-o-tolylphosphine are added to this suspension, and the reaction mixture is heated under reflux for 24 hours. After cooling, the organic phase is separated off, washed three times with 200 ml of water, filtered through silica gel, dried using sodium sulfate and subsequently evaporated to dryness. The residue is recrystallised from dioxane/ethanol and finally dried under reduced pressure. The yield is 2.42 g (1.6 mmol), corresponding to 80.9% of theory.

Example 12: Synthesis of Compound 15

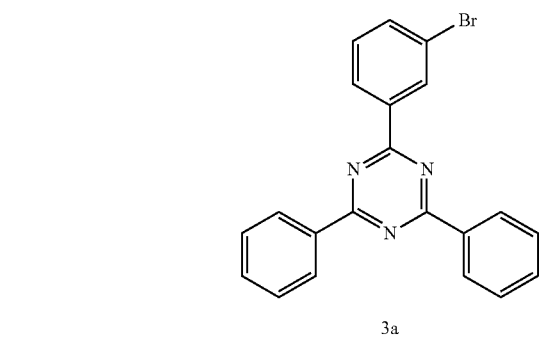

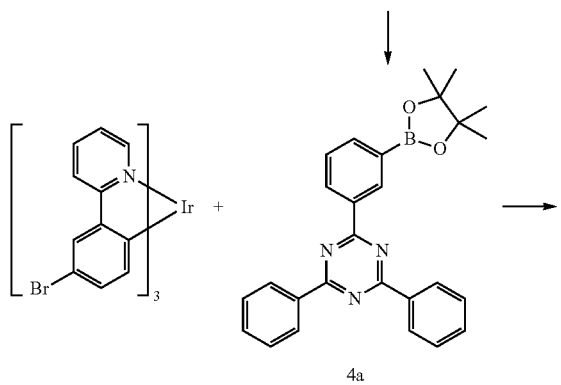

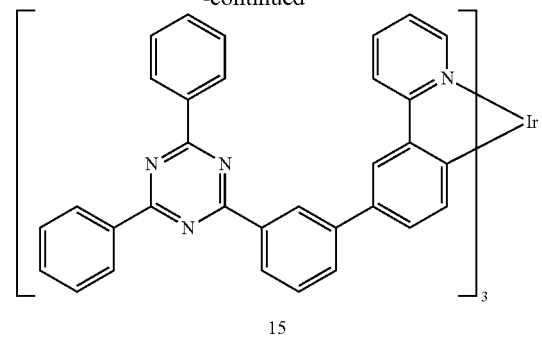

a) Synthesis of 2-(3-pinacolylboronatophenyl)-4,6-diphenyl-1,3,5-triazine (compound 4a)

The synthesis is carried out analogously to the synthesis of compound 4. The yield is 31.9 g (73 mmol), corresponding to 81.3% of theory.

b) Synthesis of fac-tris[2-(2-pyridinyl-κN)(5-(3-phenyl (4,6-diphenyl-1,3,5-triazine)phenyl)-κC] iridium(III) (compound 15)

The synthesis is carried out analogously to the synthesis of compound 14. The yield is 1.5 g (0.95 mmol), corresponding to 55.6% of theory.

Example 13: Synthesis of Compound 16 fac-Tris[2-(1-isoquinolinyl-κN)(5-(3-([3,1';5,1"]terphen-1-yl)-phenyl)phenyl)-κC]iridium(III)

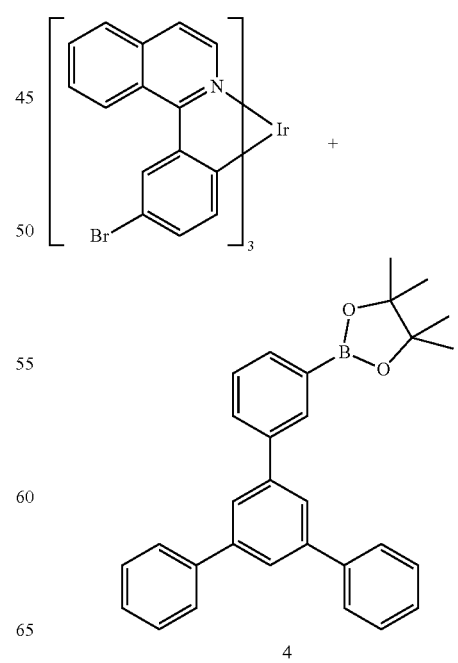

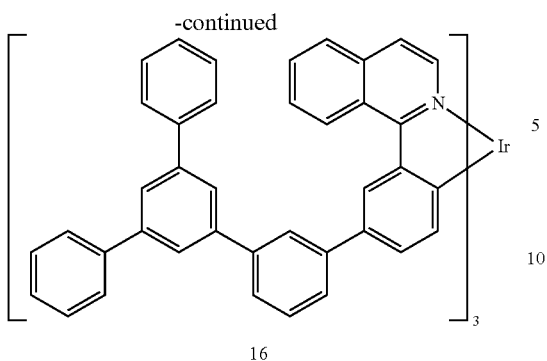
The synthesis is carried out analogously to the synthesis of compound 14. The yield is 6.52 g (3.8 mmol), corresponding to 65.6% of theory.
Example 14: Synthesis of Compound 22
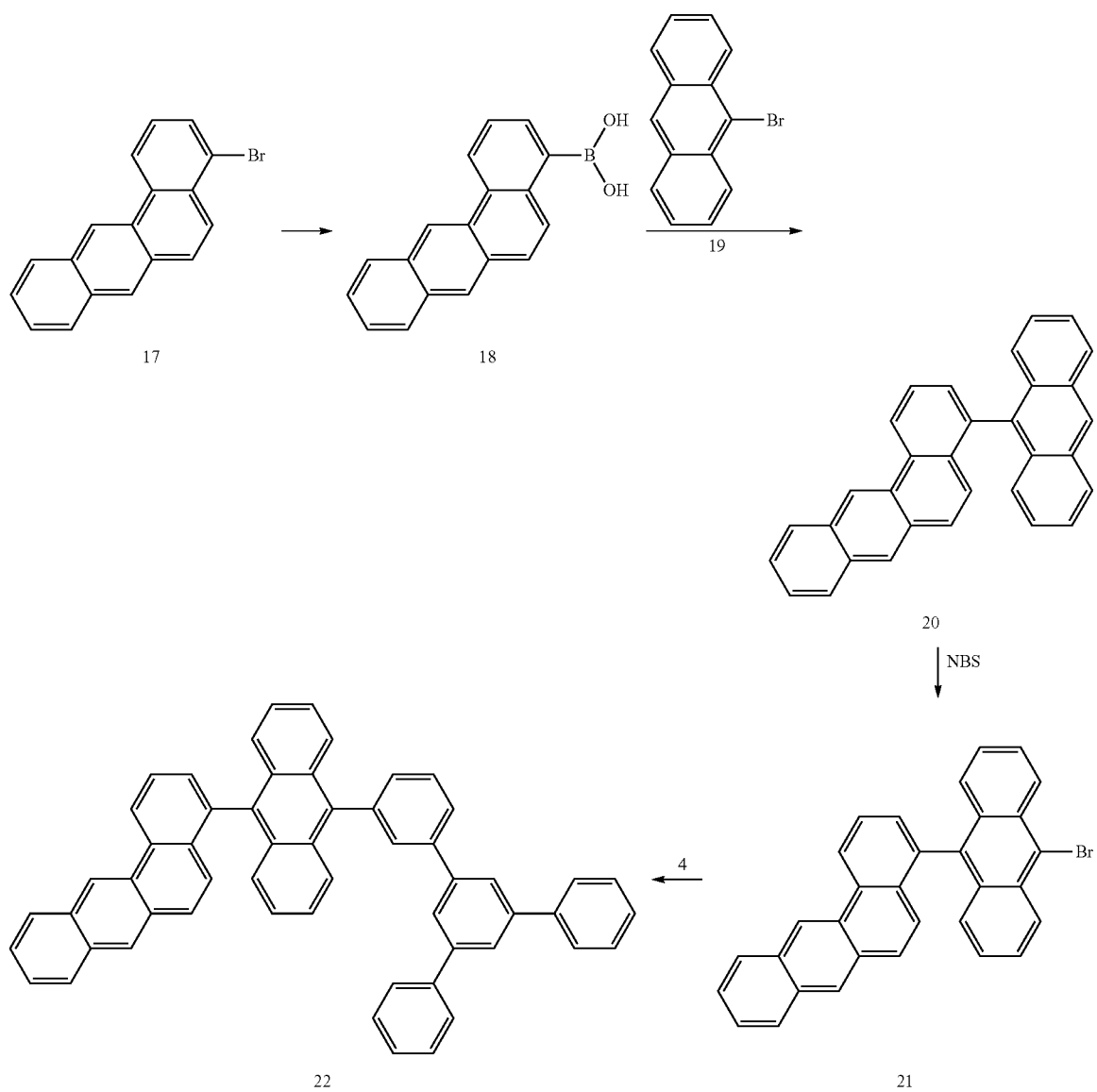

a) Synthesis of Compound 18

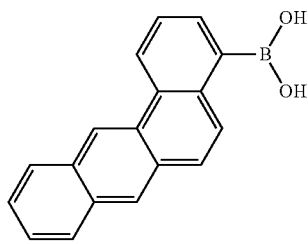

52 ml (130 mmol) of n-butyllithium (2.5 M in n-hexane) are added dropwise to a suspension of 30.7 g (100 mmol) of 4-bromobenz[a]anthracene (17) in 1000 ml of THF at −78° C. with vigorous stirring, and the mixture is stirred for a further 2 hours. 16.7 ml (150 mmol) of trimethyl borate are added in one portion to the red solution with vigorous stirring, the mixture is stirred at −78° C. for a further 30 minutes and then warmed to room temperature over the course of 3 hours, 300 ml of water are added, and the mixture is stirred for 30 minutes. The organic phase is separated off and evaporated to dryness in vacuo. The solid is taken up in 100 ml of n-hexane, filtered off with suction, washed once with 100 ml of n-hexane and dried in vacuo. Yield: 23.7 g (87.0 mmol), 87.0%, purity about 90.0% (NMR) of the boronic acid, with varying amounts of the boronic anhydride and borinic acid. The boronic acid can be used in this form without further purification.

b) Synthesis of Compound 20

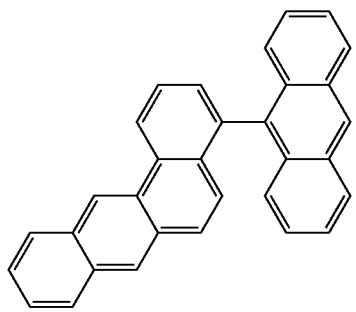

25.0 g (97.2 mmol) of 9-bromoanthracene (19), 27.0 g (99.2 mmol) of benz[a]anthracene-4-boronic acid (18) and 44.5 g (210 mmol) of tripotassium phosphate are suspended in 500 ml of toluene, 600 ml of water and 100 ml of dioxane. 1.83 g (6.01 mmol) of tri-o-tolylphosphine and then 225 mg (1.00 mmol) of palladium(II) acetate are added to this suspension, and the mixture is subsequently heated under reflux for 16 hours. After cooling, the organic phase is separated off, washed three times with 500 ml of water, dried using sodium sulfate and subsequently evaporated to dryness. The solid is recrystallised from 300 ml of toluene and finally dried under reduced pressure. The yield is 26.2 g (64.8 mmol), corresponding to 64.8% of theory.

c) Synthesis of Compound 21

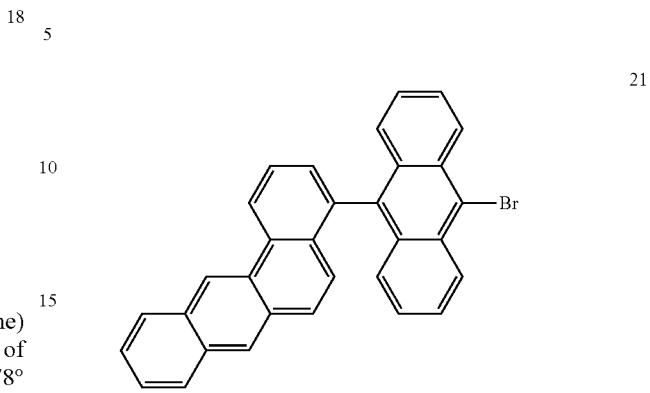

1.30 g (8.02 mmol) of iron(III) chloride and then 13.3 g (74.7 mmol) of N-bromosuccinimide are added to a suspension, cooled to 0° C., of 26.0 g (64.3 mmol) of of compound (20) in 600 ml of chloroform, and the mixture is stirred at 0° C. for 4 hours. After the mixture has warmed to room temperature, 400 ml of water are added, and the organic phase is separated off, washed three times with 300 ml of water, dried using sodium sulfate and subsequently evaporated to dryness. The orange solid obtained is recrystallised from toluene and finally dried under reduced pressure. The yield is 23.7 g (49.0 mmol), corresponding to 76.6% of theory.

d) Synthesis of Compound 22

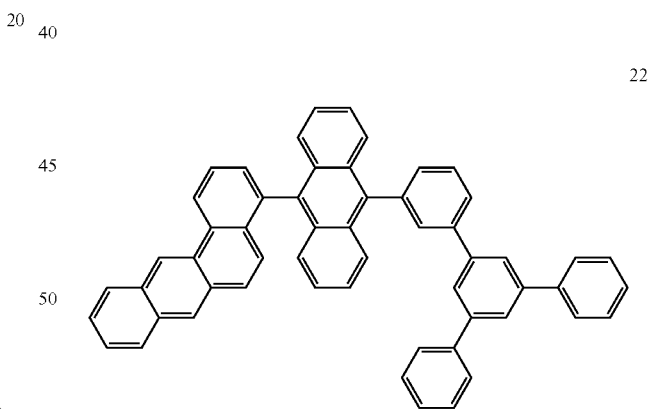

2.0 g (4.14 mmol) of compound (21), 2.00 g (4.63 mmol) of 1-boronyl-3-([3,1';5,1"]terphen-1-yl)phenyl (4) and 1.70 g (16.0 mmol) of sodium carbonate are suspended in 30 ml of toluene, 7 ml of water and 30 ml of ethanol. 70 mg (0.061 mmol) of tetrakis(triphenylphosphine)palladium(0) are added to this suspension, and the mixture is subsequently heated under reflux for 16 hours. After cooling, the precipitated solid is filtered off with suction, extracted twice with 250 ml of hot toluene and subsequently sublimed. The yield is 2.72 g (3.84 mmol), corresponding to 93.8% of theory.

Example 15: Synthesis of Compound
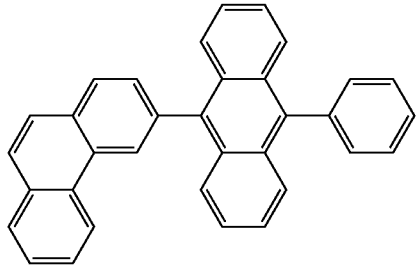
23
Compound 23 is prepared as described in WO 2009/100925.
Example 16: Synthesis of Compound 28
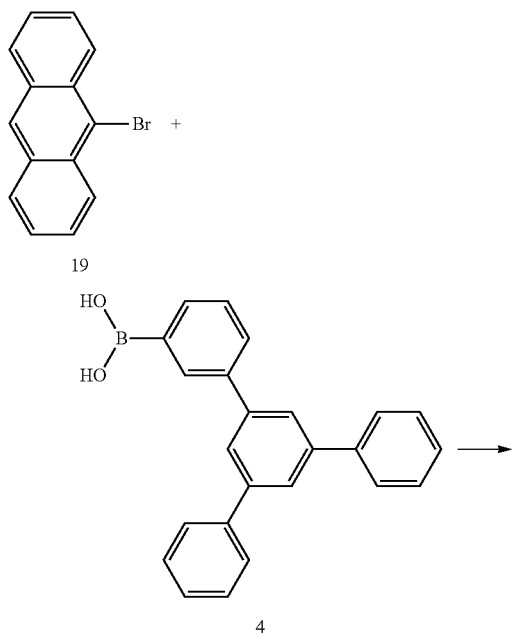
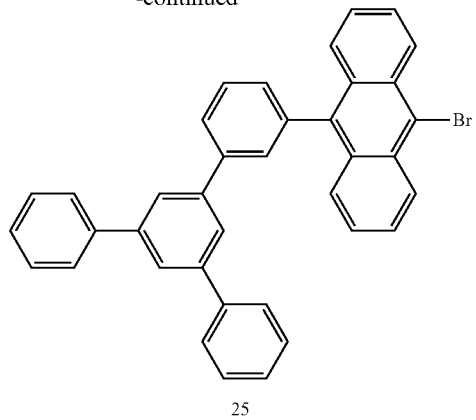
25
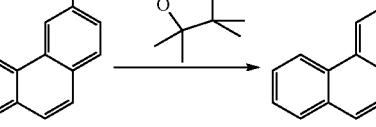
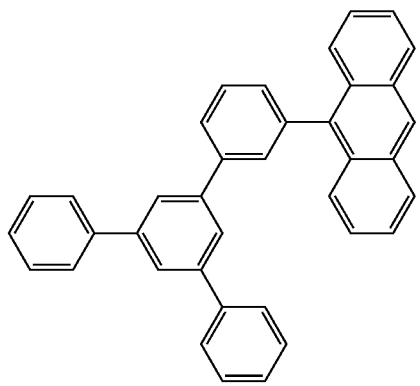
28
a) Synthesis of Compound 24
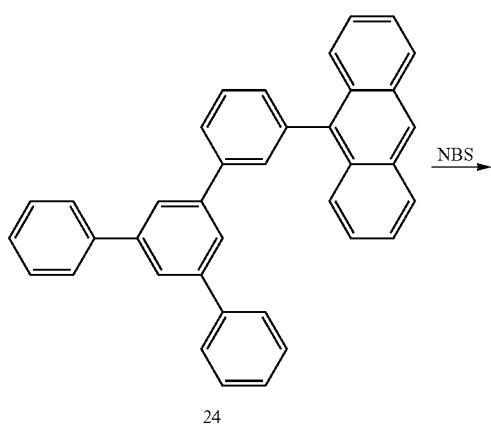
40.0 g (156 mmol) of 9-bromoanthracene (19), 74.0 g (171 mmol) of compound (4) and 58.0 g (547 mmol) of sodium carbonate are suspended in 900 ml of toluene, 900 ml of ethanol and 210 ml of water. 1.80 g (1.56 mmol) of tetrakis(triphenylphosphine)palladium(0) are added to this suspension, and the mixture is subsequently heated under reflux for 16 hours. After cooling, the solid is filtered off with suction, taken up in 500 ml of dichloromethane, the organic phase is washed three times with 100 ml of water each time, dried using sodium sulfate and subsequently evaporated to dryness. The yield is 70.2 g (145 mmol), corresponding to 92.9% of theory.

b) Synthesis of Compound 25

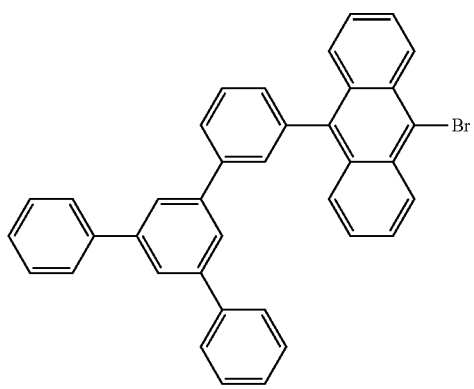

25

2.5 g (15.4 mmol) of iron(III) chloride and then 31.0 g (174 mmol) of N-bromosuccinimide are added to a suspension, cooled to 0° C., of 70.0 g (145 mmol) of compound (24) in 1.4 l of chloroform, and the mixture is stirred at 0° C. for 2 hours. After warming to room temperature, 1000 ml of water are added, the organic phase is separated off, washed three times with 500 ml of water, dried using sodium sulfate and subsequently evaporated to dryness. The solid obtained is recrystallised from a heptane/ethyl acetate mixture and finally dried under reduced pressure. The yield is 56.7 g (101 mmol), corresponding to 69.7% of theory.

c) Synthesis of Compound 27

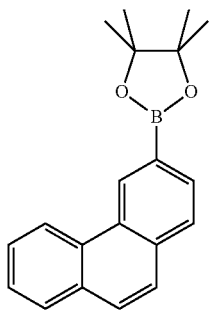

27

35.6 g (138 mmol) of 3-bromophenanthrene (26), 42.0 g (165 mmol) of bispinacolatodiboron and 46.0 g (469 mmol) of potassium acetate are suspended in 500 ml of dimethyl sulfoxide. 3.50 g (4.29 mmol) of 1,1-bis(diphenylphosphino)ferrocenedichloropalladium(II)*DCM are added to this suspension, and the reaction mixture is stirred at 80° C. for 6 hours. After cooling, 1000 ml of ethyl acetate and 1000 ml of water are added, the organic phase is separated off, washed three times with 300 ml of water each time, dried using sodium sulfate and subsequently evaporated to dryness. The crude product is passed through silica gel in a column with a heptane/ethyl acetate mixture (10:1), corresponding fractions are evaporated and finally dried under reduced pressure. The yield is 38.5 g (127 mmol), corresponding to 92.0% of theory.

d) Synthesis of Compound 28

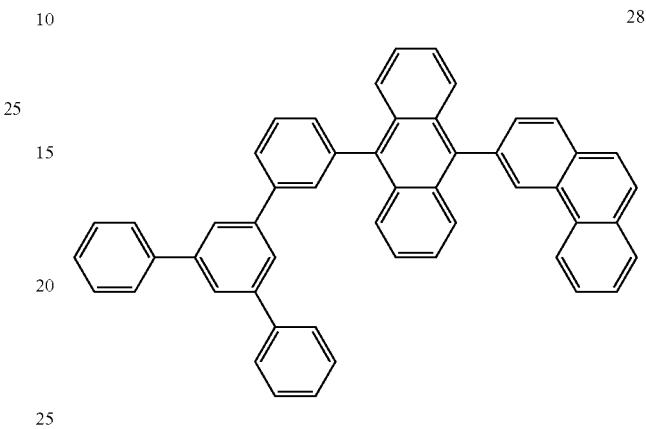

28

13.3 g (23.7 mmol) of compound (25), 7.80 g (25.6 mmol) of compound (27) and 8.80 g (83.0 mmol) of sodium carbonate are suspended in 140 ml of toluene, 140 ml of ethanol and 35 ml of water. 300 mg (260 µmol) of tetrakis (triphenylphosphine)palladium(0) are added to this suspension, and the mixture is subsequently heated under reflux for 16 hours. After cooling, the solid is filtered off with suction and extracted with 500 ml of hot toluene. The residue is recrystallised three times from heptane/toluene and sublimed. The yield is 13.1 g (19.9 mmol), corresponding to 84.0% of theory.

Compound 29

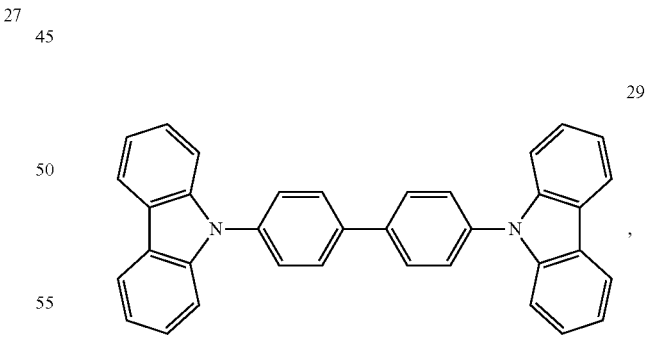

29 compound 30

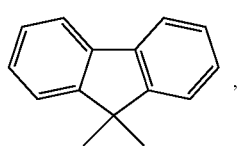

compound 31

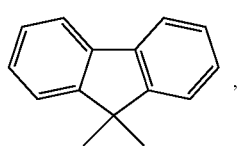

30

-continued

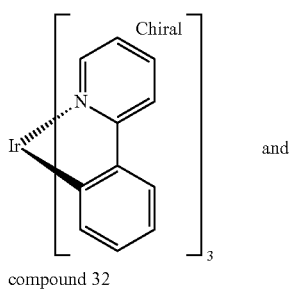

compound 32

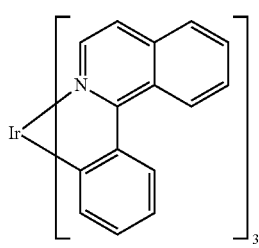

are commercially available and comprise no solubility-promoting structural elements of the formula (I).

Compound 33

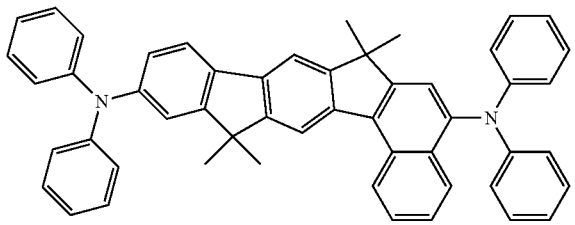

is prepared as described in WO 2008/006449.

Production and Characterisation of Organic Electroluminescent Devices

Materials to be employed in accordance with the invention are used from solution, where they result in simple devices having surprisingly good properties. The production of such components is based on the production of polymeric light-emitting diodes (PLEDs), which has already been described many times in the literature (for example in WO 2004/037887 A2). In the present case, the compounds according to the invention are dissolved in toluene or chlorobenzene. The concentration employed in the examples given here is 20% by weight of the emitter (compounds 14, 15, 16, 19 and 20) and 80% by weight of the matrix materials (compounds 5 to 13, 17 and 18). The typical solids content of such solutions is between 16 and 25 g/l if, as here, the typical layer thickness of 80 nm for a device is to be achieved by means of spin coating.

FIG. 1 shows the typical structure of a device of this type. The EML comprises the jointly dissolved matrix materials and the emitter in the form of an amorphous layer. Structured ITO substrates and the material for the so-called buffer layer (PEDOT, actually PEDOT:PSS) are commercially available (ITO from Technoprint and others, PEDOT:PPS as Clevios P aqueous dispersion from H.C. Starck). The Interlayer used (HIL-012 from Merck) serves for hole injection. The emission layer is applied by spin coating in an inert-gas atmosphere, in the present case argon, and dried by heating at 160° C. or 180° C. for 10 minutes. Finally, a cathode comprising barium and aluminium is applied by vacuum vapour deposition. The HBL and ETL layers used in the above-mentioned examples can also be applied by vapour deposition between the EML and the cathode, the interlayer can also be replaced by one or more layers, which merely have to satisfy the condition of not being detached again by the subsequent processing step of EML deposition from solution.

The devices processed from solution were characterised by standard methods, the OLED examples given were not optimised. Table 1 shows the results.

TABLE 1

Results of the device configuration in accordance with FIG. 1

| Ex. | EML 80 nm | Max. eff. [cd/A] | Voltage [V] at 1000 cd/m$^2$ | CIE (x, y) | Lifetime [h], initial luminance 1000 cd/m$^2$ |
|---|---|---|---|---|---|
| Cmpn. | Cpd. 5: cpd. 31 | 27 | 5.0 | 0.35/0.61 | 3200 |
| | Cpd. 6: cpd. 14 | 40 | 4.9 | 0.34/0.62 | 10500 |
| | Cpd. 6: cpd. 15 | 36 | 4.9 | 0.34/0.62 | 8500 |
| Cmpn. | Cpd. 5: cpd. 29: cpd. 31 | 33 | 4.7 | 0.34/0.62 | 12000 |
| | Cpd. 6: cpd. 12: cpd. 31 | 38 | 4.7 | 0.34/0.62 | 18000 |
| | Cpd. 6: cpd. 29: cpd. 14 | 40 | 4.7 | 0.34/0.62 | 20000 |
| | Cpd. 6: cpd. 29: cpd. 15 | 41 | 4.7 | 0.34/0.62 | 23000 |
| | Cpd. 5: cpd. 12: cpd. 14 | 38 | 4.7 | 0.34/0.62 | 21000 |
| | Cpd. 5: cpd. 12: cpd. 15 | 39 | 4.7 | 0.34/0.62 | 25000 |
| | Cpd. 6: cpd. 12: cpd. 14 | 41 | 4.7 | 0.34/0.62 | 22000 |
| | Cpd. 6: cpd. 12: cpd. 15 | 41 | 4.7 | 0.34/0.62 | 25000 |
| Cmpn. | Cpd. 5: cpd. 30: cpd. 31 | 25 | 6.5 | 0.33/0.63 | 6000 |
| | Cpd. 6: cpd. 13: cpd. 31 | 32 | 6.7 | 0.33/0.63 | 13000 |
| | Cpd. 6: cpd. 30: cpd. 14 | 30 | 6.7 | 0.33/0.63 | 18000 |
| | Cpd. 6: cpd. 30: cpd. 15 | 29 | 6.7 | 0.33/0.63 | 19000 |
| | Cpd. 5: cpd. 13: cpd. 14 | 30 | 6.7 | 0.33/0.63 | 14000 |
| | Cpd. 5: cpd. 13: cpd. 15 | 32 | 6.7 | 0.33/0.63 | 15000 |
| | Cpd. 6: cpd. 13: cpd. 14 | 35 | 6.7 | 0.33/0.63 | 24000 |
| | Cpd. 6: cpd. 13: cpd. 15 | 34 | 6.7 | 0.33/0.63 | 25000 |
| Cmpn. | Cpd. 7: cpd. 29: cpd. 31 | 24 | 5.3 | 0.34/0.62 | 12000 |
| | Cpd. 8: cpd. 12: cpd. 31 | 30 | 5.3 | 0.34/0.62 | 38000 |
| | Cpd. 8: cpd. 29: cpd. 14 | 33 | 5.2 | 0.34/0.62 | 45000 |

TABLE 1-continued

Results of the device configuration in accordance with FIG. 1

| Ex. | EML 80 nm | Max. eff. [cd/A] | Voltage [V] at 1000 cd/m² | CIE (x, y) | Lifetime [h], initial luminance 1000 cd/m² |
|---|---|---|---|---|---|
|  | Cpd. 8: cpd. 29: cpd. 15 | 34 | 5.1 | 0.34/0.62 | 43000 |
|  | Cpd. 7: cpd. 12: cpd. 14 | 32 | 5.2 | 0.34/0.62 | 35000 |
|  | Cpd. 7: cpd. 12: cpd. 15 | 31 | 5.2 | 0.34/0.62 | 32000 |
|  | Cpd. 8: cpd. 12: cpd. 14 | 37 | 5.1 | 0.34/0.62 | 48000 |
|  | Cpd. 8: cpd. 12: cpd. 15 | 35 | 5.1 | 0.34/0.62 | 46000 |
| Cmpn. | Cpd. 7: cpd. 30: cpd. 31 | 20 | 4.8 | 0.33/0.63 | 9000 |
|  | Cpd. 8: cpd. 13: cpd. 31 | 34 | 5.1 | 0.34/0.62 | 20000 |
|  | Cpd. 8: cpd. 30: cpd. 14 | 28 | 5.1 | 0.33/0.62 | 16000 |
|  | Cpd. 8: cpd. 30: cpd. 15 | 30 | 5.0 | 0.33/0.62 | 17000 |
|  | Cpd. 7: cpd. 13: cpd. 14 | 23 | 3.6 | 0.33/0.63 | 17000 |
|  | Cpd. 7: cpd. 13: cpd. 15 | 31 | 5.0 | 0.33/0.63 | 22000 |
|  | Cpd. 8: cpd. 13: cpd. 14 | 29 | 5.3 | 0.33/0.62 | 34000 |
|  | Cpd. 8: cpd. 13: cpd. 15 | 30 | 5.2 | 0.33/0.62 | 36000 |
| Cmpn. | Cpd. 9: cpd. 29: cpd. 31 | 21 | 6.0 | 0.34/0.62 | 6000 |
|  | Cpd. 11: cpd. 12: cpd. 31 | 35 | 5.8 | 0.34/0.62 | 24000 |
|  | Cpd. 10: cpd. 12: cpd. 31 | 36 | 5.9 | 0.34/0.62 | 28000 |
|  | Cpd. 11: cpd. 29: cpd. 14 | 38 | 5.7 | 0.34/0.62 | 26000 |
|  | Cpd. 10: cpd. 29: cpd. 14 | 39 | 5.8 | 0.34/0.62 | 25000 |
|  | Cpd. 11: cpd. 29: cpd. 15 | 39 | 5.9 | 0.34/0.62 | 24000 |
|  | Cpd. 10: cpd. 29: cpd. 15 | 40 | 5.8 | 0.34/0.62 | 25000 |
|  | Cpd. 9: cpd. 12: cpd. 14 | 33 | 5.7 | 0.34/0.62 | 28000 |
|  | Cpd. 9: cpd. 12: cpd. 15 | 34 | 5.8 | 0.34/0.62 | 29000 |
|  | Cpd. 11: cpd. 12: cpd. 14 | 40 | 5.8 | 0.33/0.63 | 50000 |
|  | Cpd. 10: cpd. 12: cpd. 14 | 41 | 5.9 | 0.34/0.62 | 53000 |
|  | Cpd. 11: cpd. 12: cpd. 15 | 39 | 5.7 | 0.34/0.62 | 48000 |
|  | Cpd. 10: cpd. 12: cpd. 15 | 40 | 5.8 | 0.34/0.62 | 49000 |
| Cmpn. | Cpd. 9: cpd. 30: cpd. 31 | 23 | 5.9 | 0.34/0.62 | 12000 |
|  | Cpd. 11: cpd. 13: cpd. 31 | 32 | 5.2 | 0.33/0.62 | 24000 |
|  | Cpd. 10: cpd. 13: cpd. 31 | 32 | 6.0 | 0.34/0.62 | 24000 |
|  | Cpd. 11: cpd. 30: cpd. 14 | 33 | 6.1 | 0.34/0.62 | 22000 |
|  | Cpd. 10: cpd. 30: cpd. 14 | 34 | 6.2 | 0.34/0.62 | 21000 |
|  | Cpd. 11: cpd. 30: cpd. 15 | 32 | 6.0 | 0.34/0.62 | 22000 |
|  | Cpd. 10: cpd. 30: cpd. 15 | 34 | 6.1 | 0.34/0.62 | 23000 |
|  | Cpd. 9: cpd. 13: cpd. 14 | 35 | 6.0 | 0.34/0.62 | 25000 |
|  | Cpd. 9: cpd. 13: cpd. 15 | 34 | 6.1 | 0.34/0.62 | 24000 |
|  | Cpd. 11: cpd. 13: cpd. 14 | 38 | 6.1 | 0.34/0.62 | 33000 |
|  | Cpd. 10: cpd. 13: cpd. 14 | 37 | 6.0 | 0.34/0.62 | 32000 |
|  | Cpd. 11: cpd. 13: cpd. 15 | 39 | 6.1 | 0.33/0.62 | 31000 |
|  | Cpd. 10: cpd. 13: cpd. 15 | 40 | 6.1 | 0.33/0.62 | 34000 |
| Cmpn. | Cpd. 5: cpd. 29: cpd. 31: cpd. 32 | 6 | 6.4 | 0.65/0.35 | 4000 |
|  | Cpd. 6: cpd. 12: cpd. 31: cpd. 32 | 9 | 6.5 | 0.65/0.35 | 16000 |
|  | Cpd. 6: cpd. 12: cpd. 31: cpd. 16 | 10 | 6.3 | 0.65/0.35 | 22000 |
|  | Cpd. 5: cpd. 12: cpd. 31: cpd. 16 | 8 | 6.3 | 0.65/0.35 | 18000 |
|  | Cpd. 6: cpd. 29: cpd. 31: cpd. 16 | 9 | 6.5 | 0.65/0.35 | 20000 |

As can be seen from the results, the formulations according to the invention represent a significant improvement over the comparable compositions in accordance with the prior art with respect to operating voltage, lifetime and efficiency of the electronic devices obtained therefrom.

Production and Characterisation of Organic Electroluminescent Devices Comprising Compounds 22 and 28 According to the Invention The materials to be employed in accordance with the invention are, as described above, dissolved in toluene or chlorobenzene. However, the concentration employed in the examples given here is 5% by weight of the emitter (cpd. 33) and 95% by weight of the matrix materials. The typical solids content of such solutions is between 10 and 15 g/l if, as here, the typical layer thickness of 50 nm for a device is to be achieved by means of spin coating.

The devices are characterised by standard methods, the OLED examples given have not yet been optimised. Table 2 summarises the data obtained.

TABLE 2

Results with materials processed from solution in the device configuration of FIG. 1.

| Ex. | EML 50 nm | Max. eff. [cd/A] | Voltage [V] at 1000 cd/m² | CIE (x, y) | Lifetime [h], initial luminance 1000 cd/m² |
|---|---|---|---|---|---|
| Cmpn. | Cpd. 23: cpd. 33 | 4.8 | 5.0 | 0.14, 0.17 | 400 |
| Cmpn. | Cpd. 28: cpd. 33 | 5.3 | 4.9 | 0.14, 0.17 | 300 |
| Cmpn. | Cpd. 23: cpd. 33 | 6.1 | 4.9 | 0.14, 0.17 | 500 |
| Cmpn. | Cpd. 23: cpd. 28: cpd. 33 | 6.1 | 4.8 | 0.14, 0.17 | 800 |
| Cmpn. | Cpd. 23: cpd. 22: cpd. 33 | 6.1 | 4.8 | 0.14, 0.17 | 700 |
|  | Cpd. 28: cpd. 22: cpd. 33 | 6.2 | 4.8 | 0.14, 0.17 | 1000 |

The invention claimed is:
1. A formulation comprising at least one solvent and at least two different functional compounds of formula (I)

$$A\text{---}[B]_k \quad (I)$$

wherein

A is a functional structural element, the structural element serving as a host material, as a unit that has hole-injection and/or hole-transport properties, as a unit that has electron-injection and/or electron-transport properties, as a unit which has light-emitting properties, or as a unit which improves the transfer from the singlet state to the triplet state of light-emitting compounds;

B is a solubility-promoting structural element; and k is an integer in the range from 1 to 20;

the molecular weight of the functional compound is at least 550 g/mol, and the solubility-promoting structural element B conforms to the general formula (L-I)

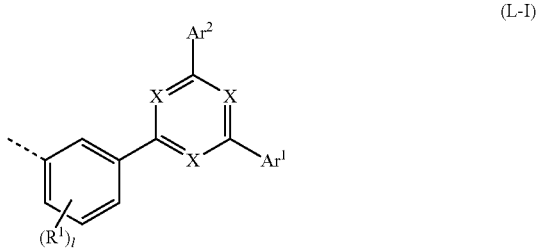

(L-I)

wherein $Ar^1$ and $Ar^2$ are each, independently of one another, an optionally substituted aryl or heteroaryl group;

X is, in each case, independently of one another, N or $CR^2$; with the proviso that in each case at least one X is N;

$R^1$ and $R^2$ are each, independently of one another, hydrogen, a straight-chain alkyl, alkoxy or thioalkoxy group having 1 to 40 C atoms or a branched or cyclic alkyl, alkoxy or thioalkoxy group having 3 to 40 C atoms or is a silyl group or a substituted keto group having 1 to 40 C atoms, an alkoxycarbonyl group having 2 to 40 C atoms, an aryloxycarbonyl group having 7 to 40 C atoms, a cyano group —CN, a carbamoyl group —C(=O)NH$_2$, a haloformyl group —C(=O)—X, wherein X is a halogen atom, a formyl group —C(=O)—H, an isocyano group, an isocyanate group, a thiocyanate group or a thioisocyanate group, a hydroxyl group, a nitro group, a CF$_3$ group, Cl, Br, F, a crosslinkable group or an optionally substituted aromatic or heteroaromatic ring system having 5 to 60 ring atoms, or an aryloxy or heteroaryloxy group having 5 to 60 ring atoms, or a combination of these systems, wherein one or more of the groups $R^1$ and/or $R^2$ optionally define a mono- or polycyclic, aliphatic or aromatic ring system with one another and/or with the ring to which the group $R^1$ is bonded; and l is 0, 1, 2, 3 or 4;

the dashed bond indicates the bond to the functional structural element A.

2. The formulation of claim 1, wherein the functional structural element A in formula (I) serves as host material.

3. The formulation of claim 1, wherein the functional structural element A in formula (I) is a unit that has hole-injection and/or hole-transport properties.

4. The formulation of claim 1, wherein the functional structural element A in formula (I) is a unit that has electron-injection and/or electron-transport properties.

5. The formulation of claim 1, wherein the functional structural element A in formula (I) is a unit which has light-emitting properties.

6. The formulation of claim 1, wherein the formulation comprises at least one functional compound in which the functional structural element A in formula (I) is a unit having phosphorescent properties.

7. The formulation of claim 6, wherein the formulation comprises at least one functional compound in which the functional structural element A in formula (I) is a unit which includes at least one heavy atom having an atomic number of greater than 36.

8. The formulation of claim 1, wherein the functional structural element A in formula (I) is a unit which improves the transfer from the singlet state to the triplet state of light-emitting compounds.

9. The formulation of claim 1, wherein the formulation comprises at least one functional compound in which the functional structural element A in formula (I) is a unit which has light-emitting properties, and at least one functional compound in which the functional structural element A in formula (I) is a unit which can serve as host material.

10. The formulation of claim 1, wherein the formulation comprises at least two functional compounds in which the functional structural element A in formula (I) is a unit which can serve as host material.

11. The formulation of claim 1, wherein the formulation comprises at least one functional compound in which the functional structural element A in formula (I) is a unit which can serve as host material, where the functional structural element A has at least one nitrogen atom.

12. The formulation of claim 1, wherein the formulation comprises at least one functional compound which comprises no solubility-promoting structural element B of the general formula (L-I).

13. The formulation of claim 1, wherein the proportion of functional compounds in the formulation which comprise no solubility-promoting structural element B of the general formula (L-I) is at most 50% by weight, based on the total weight of the functional compounds.

14. The formulation of claim 1, wherein the formulation comprises at least 80% by weight of aromatic or heteroaromatic solvent.

15. The formulation of claim 1, wherein the index k in formula (I) is an integer greater than or equal to 2.

16. The formulation of claim 1, wherein the molecular weight of the functional compound of the general formula (I) is at least 800 g/mol.

17. The formulation of claim 1, wherein the functional compound of the general formula (I) has a glass-transition temperature of at least 70° C.

18. The formulation of claim 1, wherein the weight ratio of structural element A to structural element B in formula (I) is in the range from 2:1 to 1:20.

19. An electronic device produced from the formulation of claim 1.

20. The electronic device of claim 19, wherein the at least two functional compounds of the general formula (I) is present in the device as hole-transport, hole-injection, emitter, electron-transport, electron-injection, charge-blocking and/or charge-generation layer.

21. The electronic device of claim 19, wherein the electronic device is an organic electroluminescent device, a polymeric electroluminescent device, an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell, or an organic laser diode.

22. A process for producing an electronic device comprising (1) applying the formulation of claim 1 to a substrate and (2) drying the applied formulation.

23. The formulation of claim 1, wherein X is, in each case, N.

* * * * *